(12) United States Patent
Thompson et al.

(10) Patent No.: US 11,464,713 B2
(45) Date of Patent: Oct. 11, 2022

(54) DOCKING STATION FOR AN ENTERAL FEEDING DEVICE

(71) Applicant: ROCKFIELD MEDICAL DEVICES LIMITED, Galway (IE)

(72) Inventors: Tomas Martin Thompson, Athenry (IE); Donal Mayne, Celbridge (IE); Damian Kelly, Galway (IE)

(73) Assignee: ROCKFIELD MEDICAL DEVICES LIMITED, Galway (IE)

( * ) Notice: Subject to any disclaimer, the term of this patent is extended or adjusted under 35 U.S.C. 154(b) by 317 days.

(21) Appl. No.: 16/071,250

(22) PCT Filed: Feb. 15, 2017

(86) PCT No.: PCT/EP2017/053408
§ 371 (c)(1),
(2) Date: Jul. 19, 2018

(87) PCT Pub. No.: WO2017/140731
PCT Pub. Date: Aug. 24, 2017

(65) Prior Publication Data
US 2019/0314249 A1    Oct. 17, 2019

(30) Foreign Application Priority Data

Feb. 15, 2016  (EP) .................................... 16155762
Feb. 15, 2016  (EP) .................................... 16155765
Dec. 16, 2016  (EP) .................................... 16204889

(51) Int. Cl.
*A61J 15/00*    (2006.01)
*G16H 40/63*    (2018.01)
*G01G 19/00*    (2006.01)

(52) U.S. Cl.
CPC ............. *A61J 15/008* (2015.05); *G01G 19/00* (2013.01); *G16H 40/63* (2018.01); *A61M 2202/0482* (2013.01); *A61M 2205/50* (2013.01)

(58) Field of Classification Search
CPC ................ A61J 15/088; A61J 15/0076; A61M 2202/0482; A61M 5/145; A61M 5/2425;
(Continued)

(56) References Cited

U.S. PATENT DOCUMENTS 5,135,485 A * 8/1992 Cohen ................. A61M 5/1684
                                                324/606
8,021,322 B1 * 9/2011 Francis ................... A61J 15/00
                                                604/66
(Continued)

FOREIGN PATENT DOCUMENTS

WO    2014/043499 A1    3/2014
WO    2014/179594 A2    11/2014
WO    2014/179594 A3    11/2014

OTHER PUBLICATIONS

International Search Report issued in PCT/EP2017/053408; dated Apr. 6, 2017.
(Continued)

*Primary Examiner* — Tiffany Legette
*Assistant Examiner* — Antarius S Daniel
(74) *Attorney, Agent, or Firm* — Studebaker & Brackett PC

(57) ABSTRACT

A docking station receives an enteral feeding pump or food pod into a cradle with a scales platform. The docking station is calibrated to determine nutritional data consumption and remaining available food on the basis of remaining food weight and nutritional data read from a tag using NFC. The station has a sealing sleeve with a sealing rim to confine any
(Continued)

spillages in a manner which does not affect weight of the device on a weighting platform.

11 Claims, 68 Drawing Sheets

(58) Field of Classification Search
CPC ............ A61M 5/14586; A61M 5/1413; A61M 5/152; A61M 2205/3379; A61M 2205/3327; A61M 2205/3389; A61M 2209/086; A61M 5/16845; A61M 5/16895; A61M 1/0023; A61M 1/28; G16H 40/60; G16H 40/63; G16H 40/67; G01G 19/00; B65D 83/0061
See application file for complete search history.

(56) References Cited

U.S. PATENT DOCUMENTS

| | | | | |
|---|---|---|---|---|
| 8,177,740 | B1* | 5/2012 | McGlothlin | A61M 5/152 604/82 |
| 9,699,816 | B2* | 7/2017 | Harr | H02J 50/10 |
| 2002/0169412 | A1* | 11/2002 | Haar | A61M 5/30 604/70 |
| 2011/0160649 | A1* | 6/2011 | Pan | A61M 1/1643 177/1 |
| 2013/0184676 | A1* | 7/2013 | Kamen | G16H 20/17 604/506 |
| 2013/0281965 | A1* | 10/2013 | Kamen | G16H 40/63 604/500 |
| 2014/0025039 | A1* | 1/2014 | Rajendran | A61M 19/00 604/512 |
| 2014/0207068 | A1* | 7/2014 | Silver | F04B 43/073 604/153 |
| 2015/0061876 | A1* | 3/2015 | Chang | A61M 5/16845 340/613 |
| 2017/0035974 | A1* | 2/2017 | Berry | A61M 5/2425 |
| 2018/0200427 | A1* | 7/2018 | Cho | A61M 5/148 |

OTHER PUBLICATIONS

Written Opinion issued in PCT/EP2017/053408; dated Apr. 6, 2017.
European Search Report issued by the European Patent Office dated Jul. 25, 2016, which corresponds to European Patent Application No. 16 15 5763.2-1557.

* cited by examiner

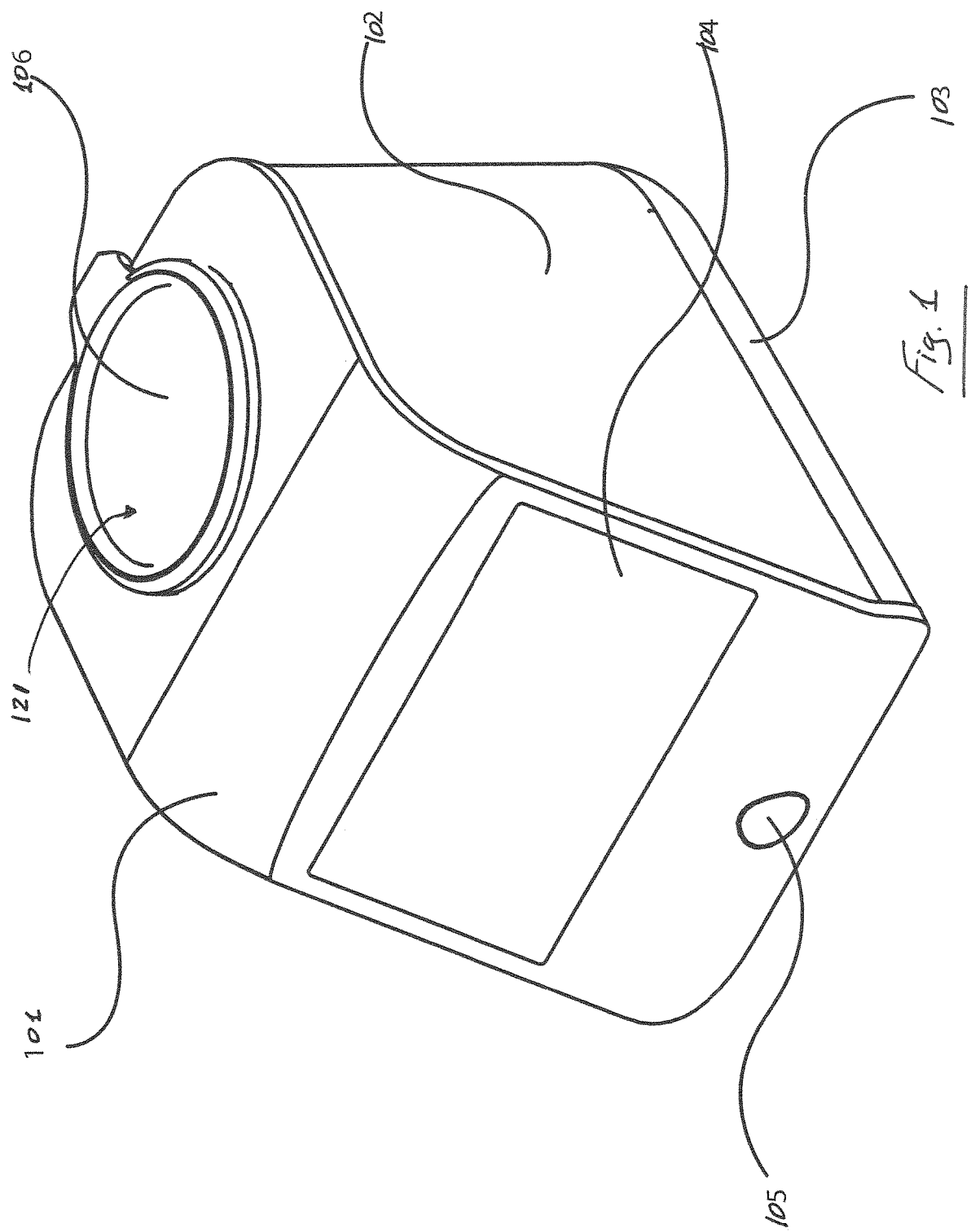

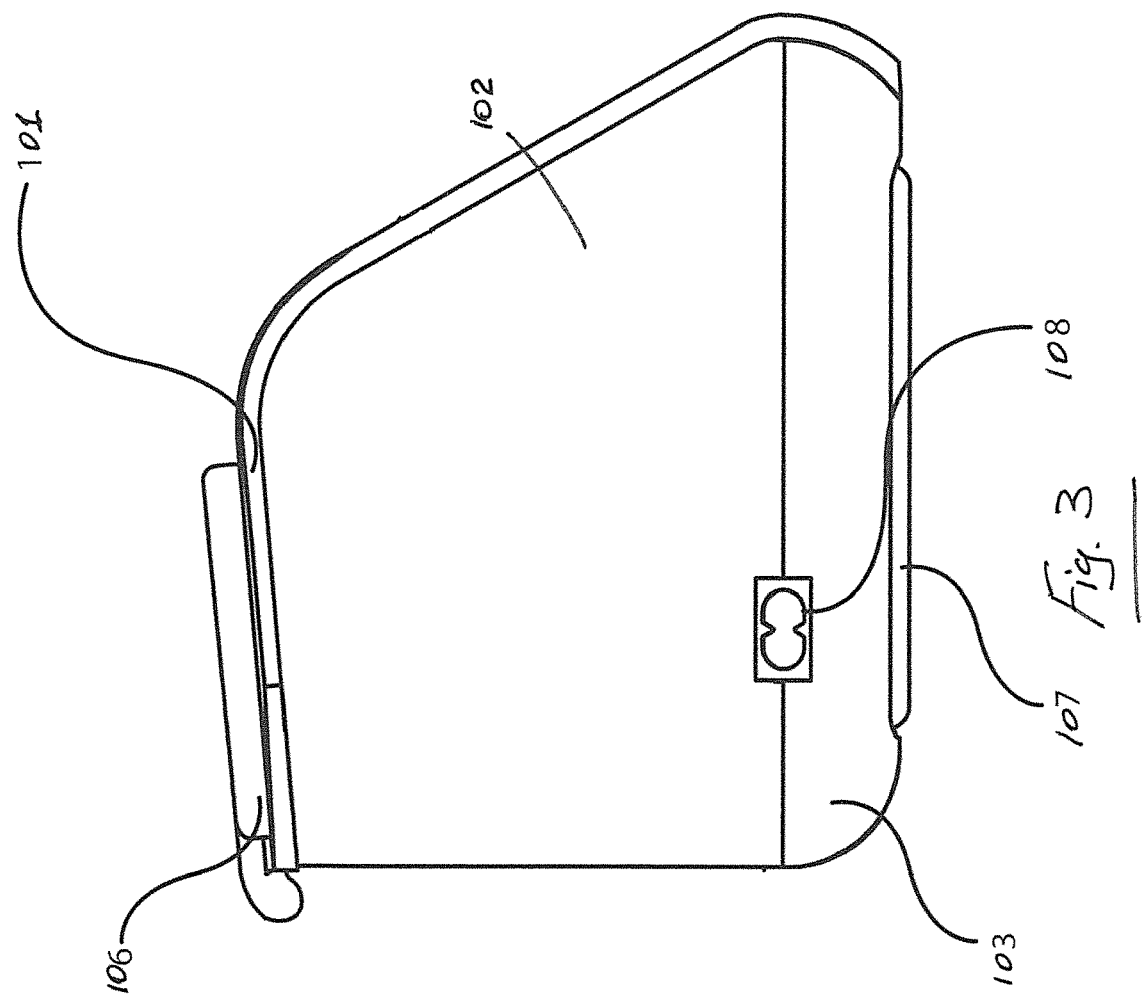
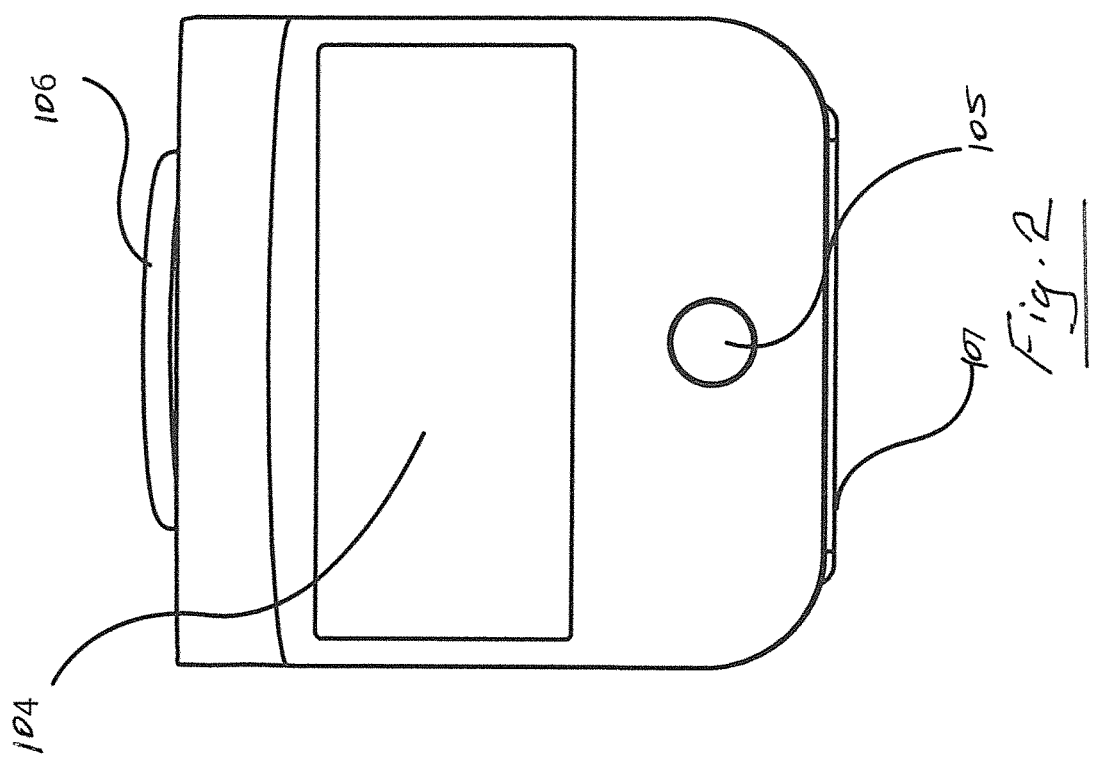

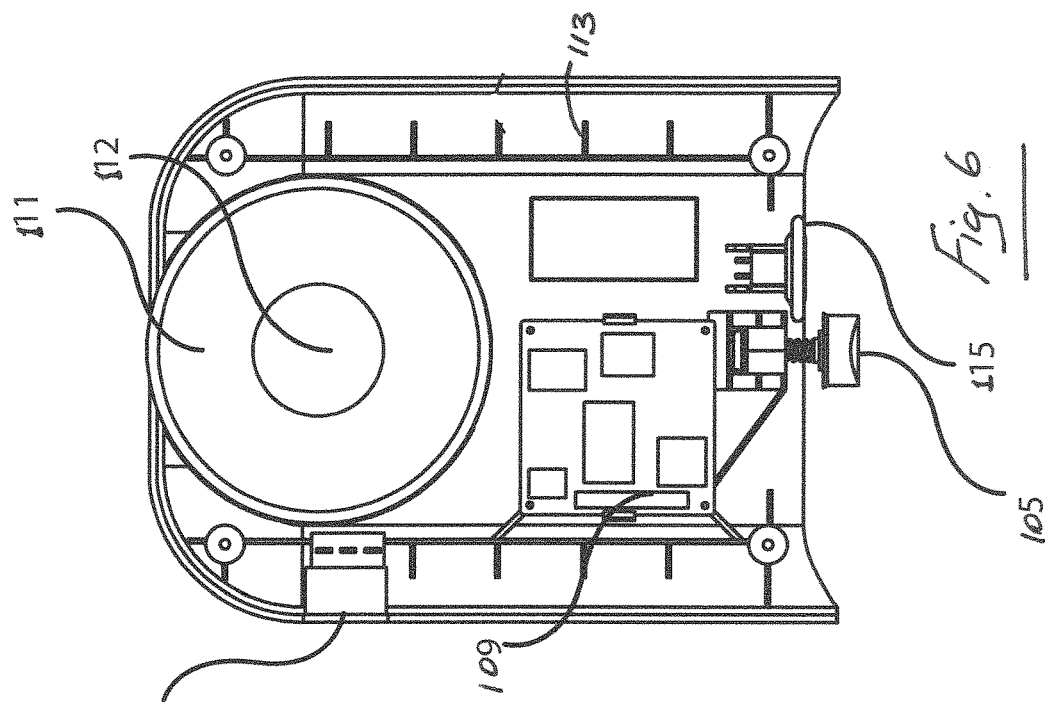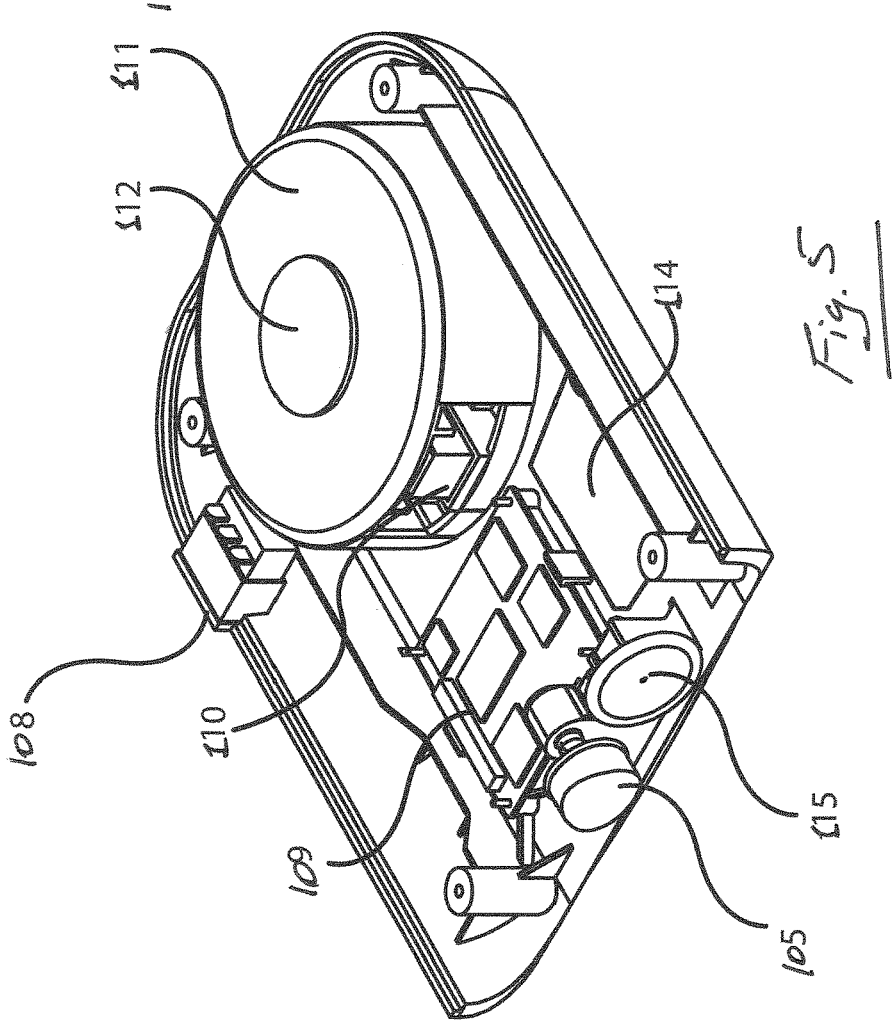

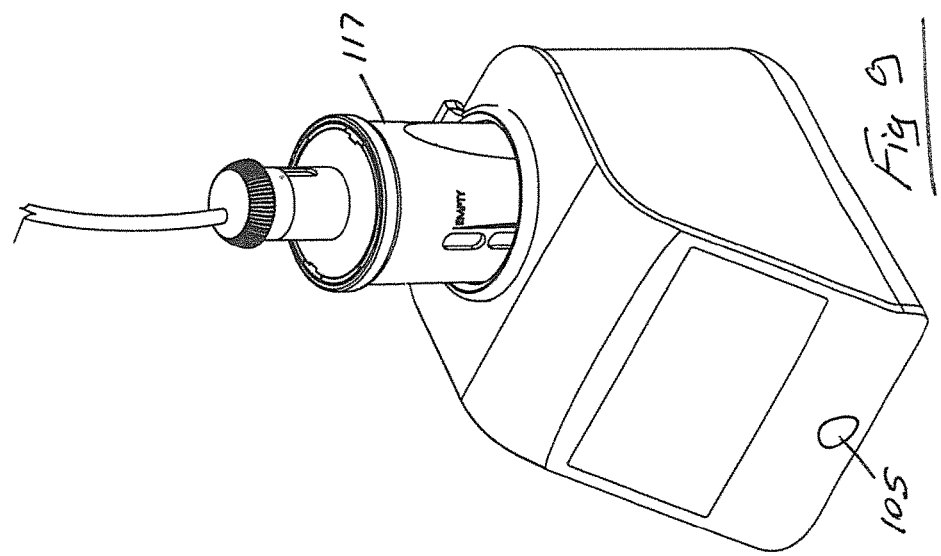
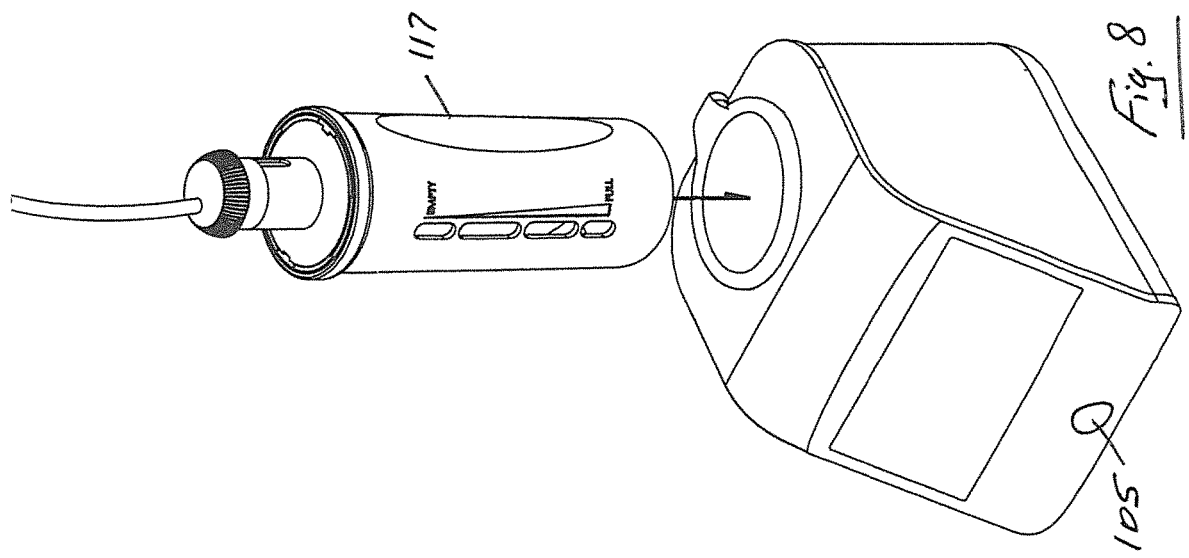

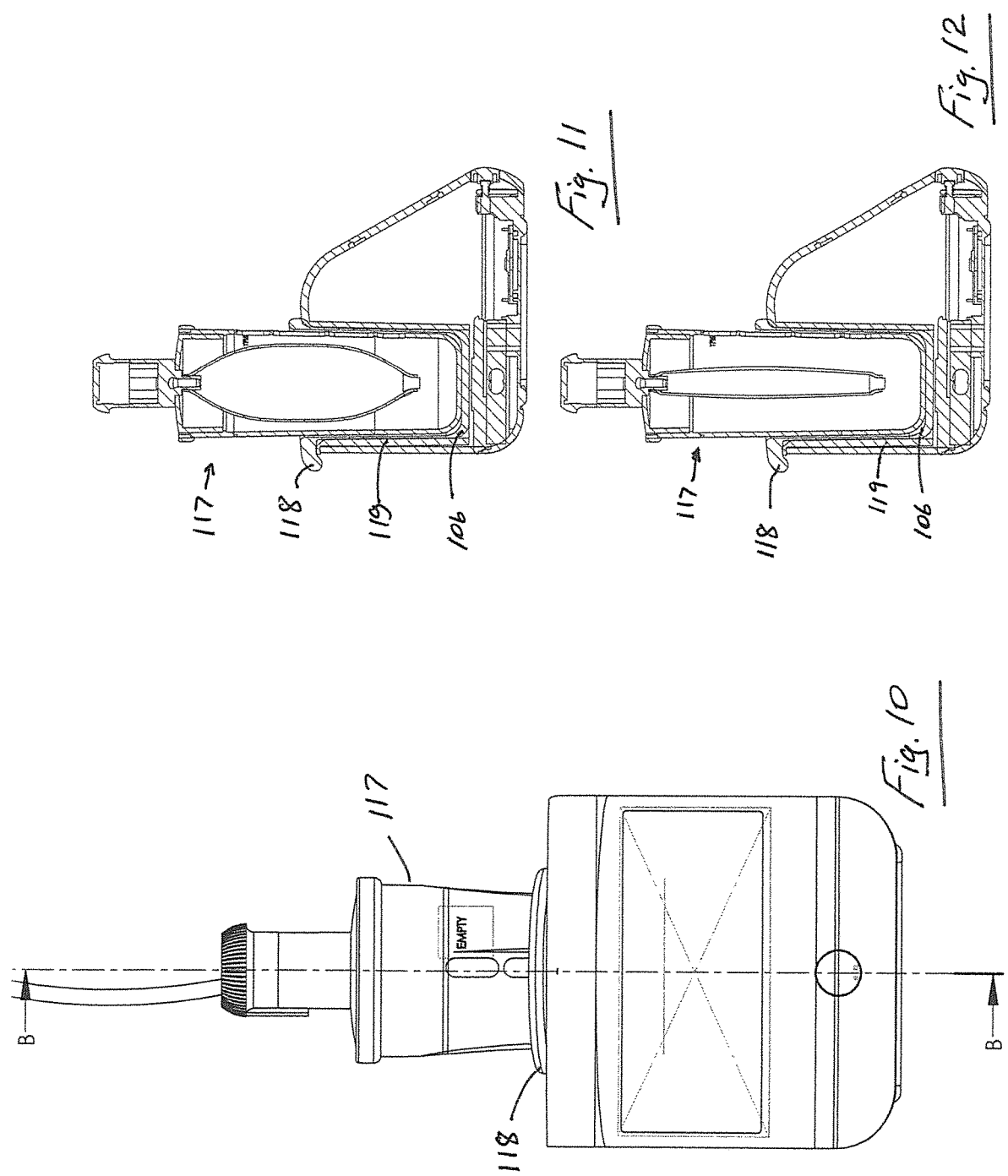

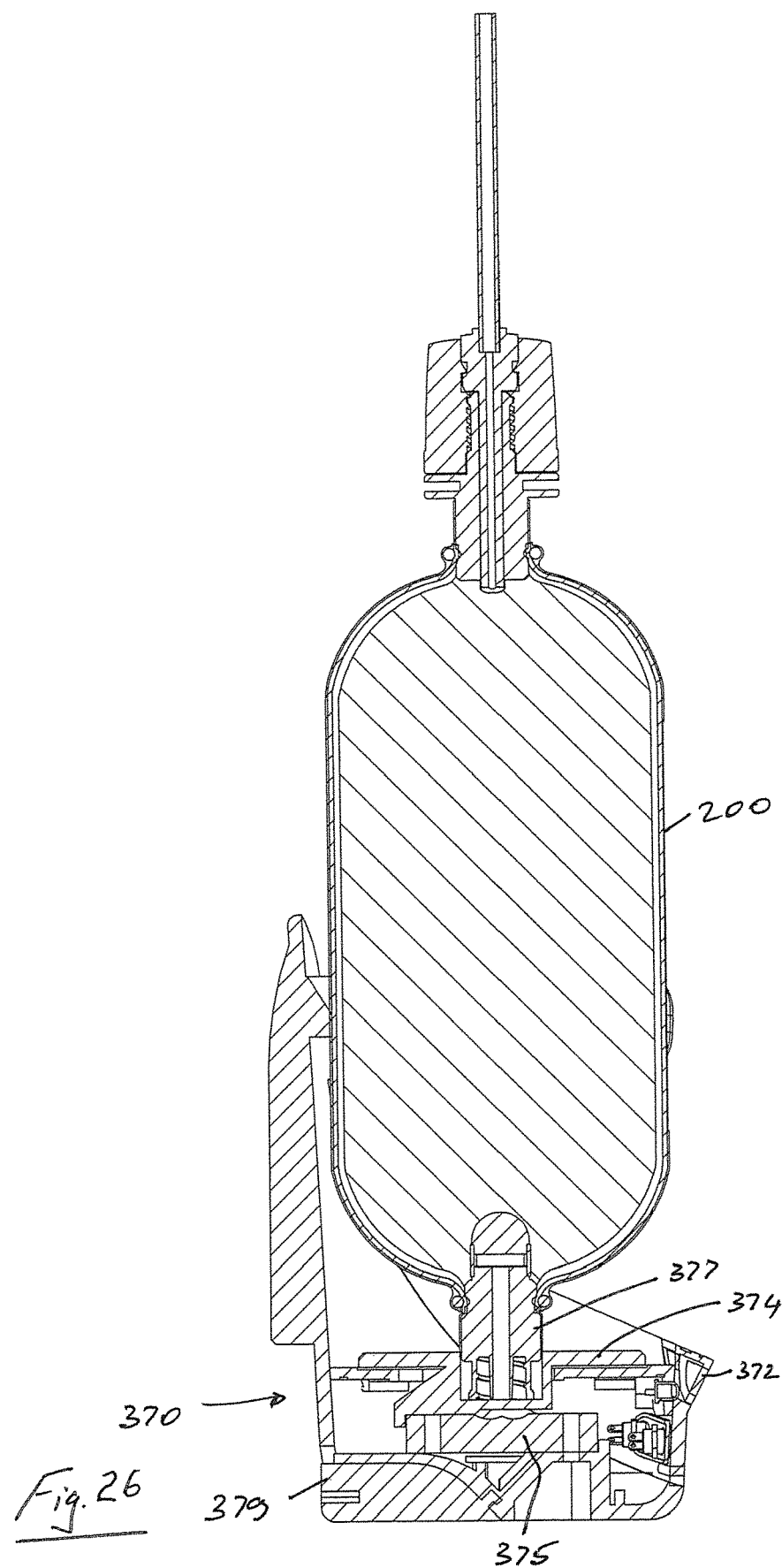

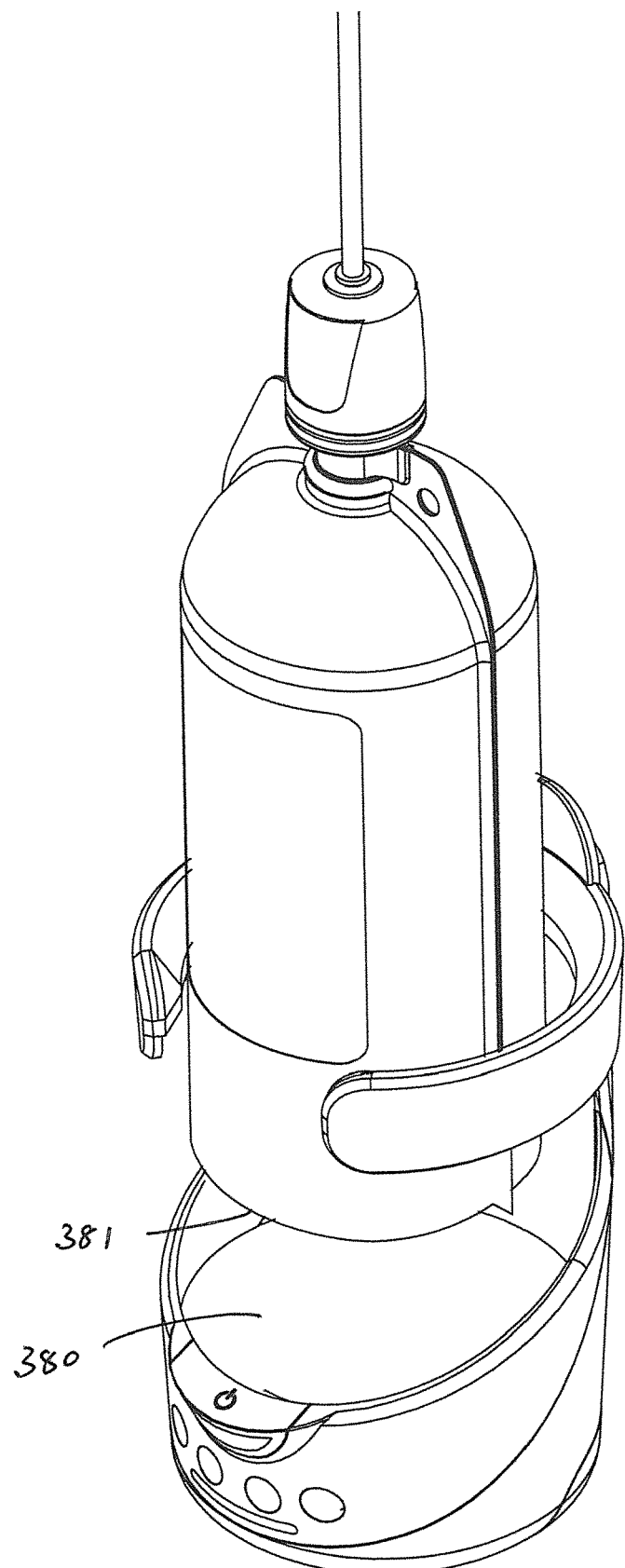
Fig. 28 (α)

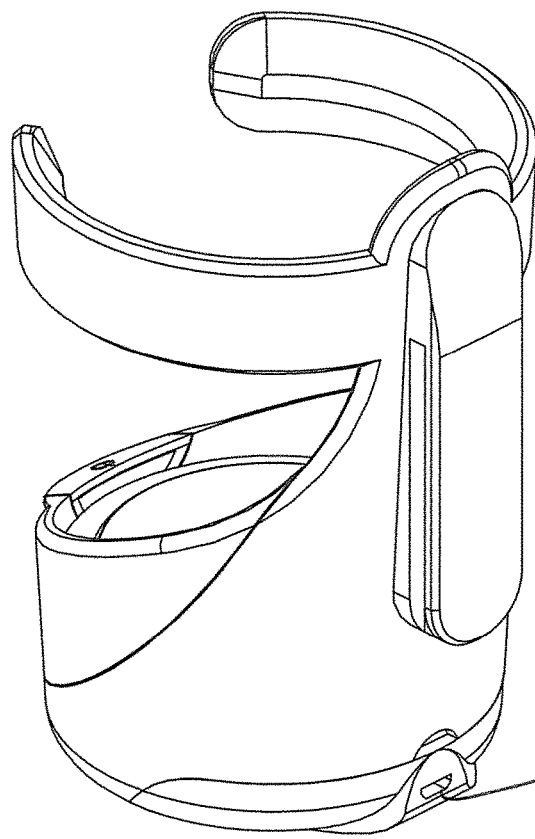
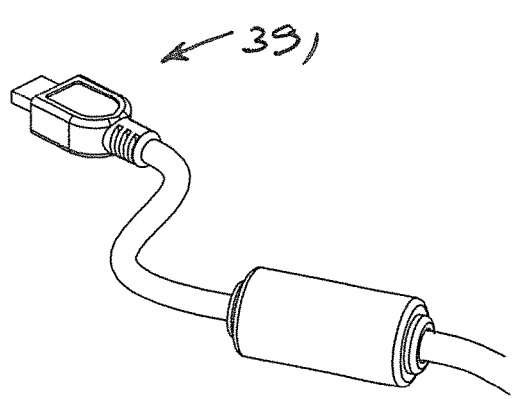
Fig. 31(b)

SECTION B-B

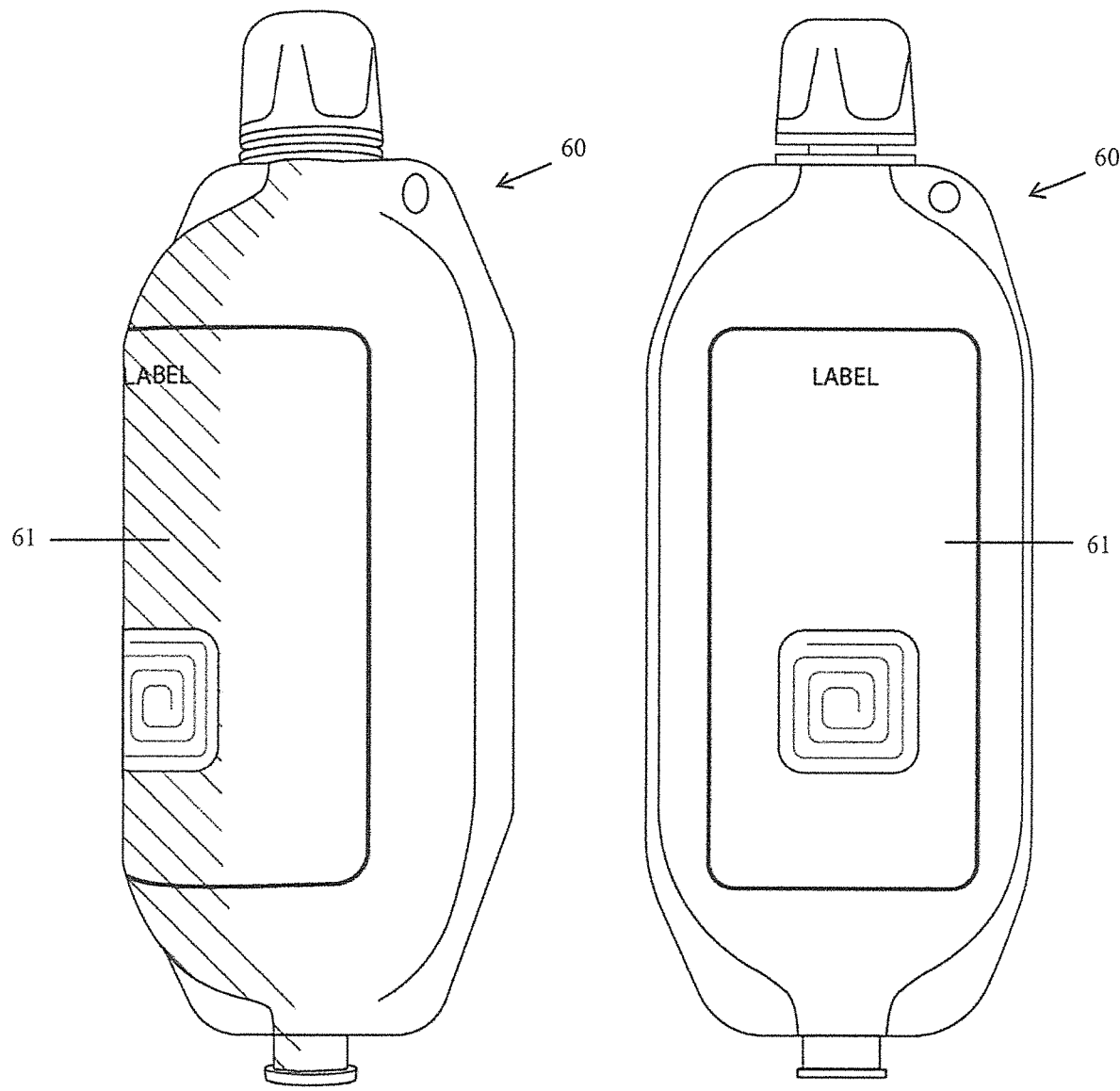

DOCKING STATION FOR AN ENTERAL FEEDING DEVICE

INTRODUCTION

The invention relates to enteral feeding devices.

Enteral feeding or tube feeding is used worldwide by people who are unable to voluntarily eat or swallow food. Enteral feeding delivers the required nutrition to these people, by the use of a battery or electronic pump, which administers a prescription formula or nutritional feed directly into the stomach or nasal system, through a tube.

Nutritional feed is supplied through a tube to a patient by a pump. A single serving of approximately 500 ml to 1000 ml of feed to a patient can take from 4 to 8 hours to be administered. Patients may be seated or lying down during feeding and may be asleep. Due to the length of time required for feeding, errors are likely to occur.

For example, the feed supply may become empty before the end of the feed cycle and more feed is required to be inserted. The supply tube to the patient may become twisted causing a kink on the line, thus slowing down the supply of feed or stopping the supply completely Nutritional feed, as it is required to deliver a nutritionally dense combination of proteins, carbohydrates, fats, waters, minerals and vitamins, is highly viscous in consistency. Because of this, clogs can occur in the mixture before it reaches the patient, affecting the supply of feed to the patient.

Should an error occur, and go unnoticed, the patient will not have received the nutrients needed and the feed will be required to be repeated.

The invention is directed towards providing a docking station which will overcome at least some of these problems.

SUMMARY OF THE INVENTION

The invention provides a docking station which hygienically supports the pump in conjunction with a detector which monitors the quantity the feed, such as by weight monitoring. This information is processed in such a way as to alert the user of any faults, and to provide useful information to optimise a feed. The docking station provides real time alerts to a user and allows the user to locally control the operation of the feeding device.

According to the invention there is provided a docking station for an enteral feeding device comprising a detector to determine a quantity of feed in an enteral feeding device, a processor to determine usage data according to inputs from the detector and an interface to output data from the processor. The interface may provide user outputs and/or be adapted for user input data either locally and/or remotely.

In one embodiment, the detector comprises a weighing platform.

In one embodiment, the docking station further comprises a guide means for guiding an enteral feeding device to the detector. In one embodiment, the guide means comprises a tubular member for guiding an enteral feeding device to the detector.

In one embodiment, the docking station comprises a sleeve for sealing engagement with an enteral feeding device. Preferably, the sleeve comprises a rim for surrounding and sealing against an enteral feeding device.

In one embodiment, the processor is configured to detect a fault in an enteral feeding system. In one embodiment, the processor is configured to identify fault based on the rate of change of weight of the enteral feeding device.

In one embodiment, the processor is configured to identify an abrupt stop in feed supply from an enteral feeding device. In one embodiment, the processor is configured to identify when a quantity of feed is below a pre-set level.

In one embodiment, the docking station comprises a sensor for detecting an enteral feeding device. In one embodiment, the processor is calibrated to determine the nutritional content of feed in the pump by the sensor reading data from a tag on the pump.

In one embodiment, the sensor communicates with the tag using a wireless communication protocol such as Near Field Communication.

In one embodiment, the processor is configured to determine remaining nutritional data according to data received from the tag and pump weight measurements.

In one embodiment, the processor is configured to use security credentials to communicate with the tag.

In one embodiment, the processer is configured to alert the user to a fault in the supply of the feed. In one embodiment, the alert is provided through a local alarm at the docking station. In one embodiment, the alert is transmitted to another device either local to or remote from the docking station.

In one embodiment the docking station comprises a receiver for receiving data from a remote device.

In some cases the docking station comprises a transmitter for transmitting data to a remote device.

In some embodiments the detector is configured for engagement with an enteral feeding device. The detector may be shaped to receive at least a portion of a base of an enteral feeding device.

In some cases the docking station comprises a power port for receiving a removable battery pack.

In one embodiment the docking station comprises a USB port to provide power to the docking station.

In some cases the docking station further comprises a mounting system for the docking station.

In one arrangement the mounting system comprises a suction cup.

In another arrangement the mounting system comprises a bracket. The bracket may be configured for attachment to a support such as a pole.

In a further arrangement the mounting system comprises a hanger. The hanger may be adapted for suspension on a pole. The docking station in some cases comprise a hook for engagement with an enteral feeding device.

The invention also provides an enteral feeding system comprising a docking station of the invention and an enteral feeding device arranged to fit into or onto the docking station.

In one embodiment the feeding device and the docking station comprises interfaces for wireless communication.

In one embodiment the feeding device comprises a tag with stored nutritional data and the docking sensor interface is arranged to read said data.

In one case the portable enteral feeding device comprises a pouch which defines a reservoir for enteral fluid, an outlet port for delivery of enteral fluid from the pouch, the apparatus having an expansile element which is adapted to provide the force by which enteral fluid is delivered from the pouch through the outlet port.

The pouch may comprise the expansile element, the pouch having an expanded filled configuration and a collapsed configuration.

The expansile element may comprise an expansile polymeric material.

There may be a substantially gas impermeable barrier surrounding the pouch.

In one case, when the pouch is filled with enteral fluid, the pouch substantially conforms to the shape of the inner surface of the surrounding barrier. As fluid is delivered from the pouch, a space may be formed between the pouch and the barrier.

In one embodiment the barrier comprises a membrane. The membrane may comprise a gas impermeable membrane such as a metallic foil.

In some cases the device is free-standing. The device may have a base support.

In one embodiment the device further comprises an indicator such as Near Field Communication tag.

In some cases the device further comprises a sensor for detecting properties associated with enteral food. The sensor may be a weight sensor, a volume sensor, or a pressure sensor.

In some cases the outlet port comprises a seal. The seal may be of a pierceable material such as a foil.

The delivery port may comprise engagement features for engagement with a Leur or ENFit connector for connection to an enteral tube feeding fixture.

There may be a removable cap for the outlet port. In some cases there is an inlet port for delivery of enteral fluid into the pouch. The inlet port may comprise engagement features for engagement with a Leur or an ENFit connector. The inlet port may comprise a seal.

In some cases a portable enteral feeding system comprises a mounting means for mounting the apparatus to a stand.

In some embodiments the enteral feeding system comprises a feeding tube having a Leur or ENFit connector at a first end for connection to the pouch outlet and a Leur or ENFit connector at a second end for connection to a PEG fixture. The enteral feeding system may further comprise a regulator for regulating the flow of enteral fluid to the PEG.

BRIEF DESCRIPTION OF THE DRAWINGS

The invention will be more clearly understood from the following description of some embodiments thereof, given by way of example only with reference to the accompanying drawings in which:

FIG. 1 is an isometric view of an enteral feeding pump docking station;

FIG. 2 is a front view of the docking station;

FIG. 3 is a side view of the docking station;

FIG. 5 is a perspective view a base of the docking station, and

FIG. 6 is a plan view of the internal of the docking station;

FIG. 8 is a perspective view of the docking station with pump being inserted, and FIG. 9 is of the pump fully inserted;

FIG. 10 is a front view of the docking station with the pump inserted into the inner flexible tube;

FIGS. 11 and 12 are cross sectional views of the docking station pump inserted into the inner flexible tube;

FIG. 26 is a side cross section of the docking station of FIGS. 22 to 24 with a food pod in position;

FIG. 31(b) is another view of the docking station of FIG. 31(a) with the charger removed;

FIGS. 82 and 83 show a further enteral feeding apparatus with near field communication tags on the labelling;

DETAILED DESCRIPTION

Figure 4:
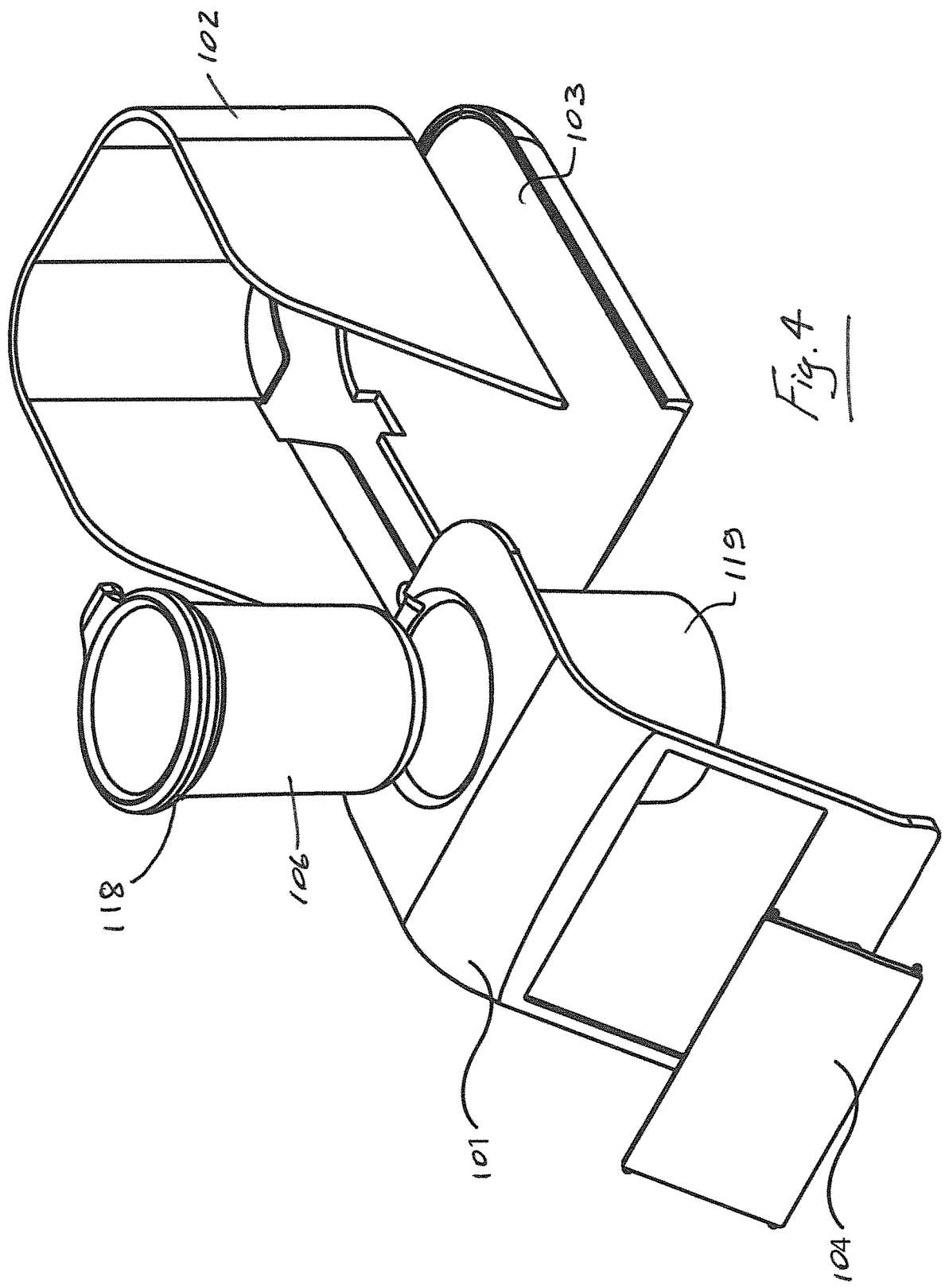
FIG. 4 is an exploded view of the docking station casing.

Referring to the drawings and initially to FIGS. 1 to 14, there is illustrated a docking station 100 having a receiver 101 for an enteral feeding device 117, especially a food pod 200. The docking station 100 comprises a detector such as a weighing device 110, 111, to determine a quantity of feed in the enteral feeding device 117. An on-board processor 109 is used to determine usage data according to inputs from the detector. A user display or interface 104 is used to provide output signals and/or data from the processor to the user.

In some cases, the interface 104 may be used to program the device.

The docking station 100 comprises guide means for guiding the enteral feeding device 117 to the detector, in this case a scales platform 111. The guide means may be provided by a tubular member 119 extending from the receiver 121 towards the scales platform 111. The docking station also has a sleeve 106 for sealing engagement with the enteral feeding device 117. The sleeve 106 has a sealing rim and confines any spillages that may occur, preventing spillages from contacting the sensitive detector or processing elements of the docking station.

Referring to FIGS. 1 to 4 there is illustrated a docking station 100 comprising a housing with a top cover shell 101, a middle shell 102 and a bottom shell 103. The top cover shell 101 has a touch display interface 104, and an activation on/off button 105 incorporated into it. A guide for supporting a pump in the docking station has a tube 119. A flexible sleeve 106 with a rim 118 surrounds the pump. The docking station can be gripped to a surface by a surface gripping coating 107 on the bottom shell 103. There is a power input 108 incorporated into the middle shell 102. The inner flexible tube 106 acts as a hygienic protector for the pump, with the rim sealing any spillages that may occur.

Figure 7:
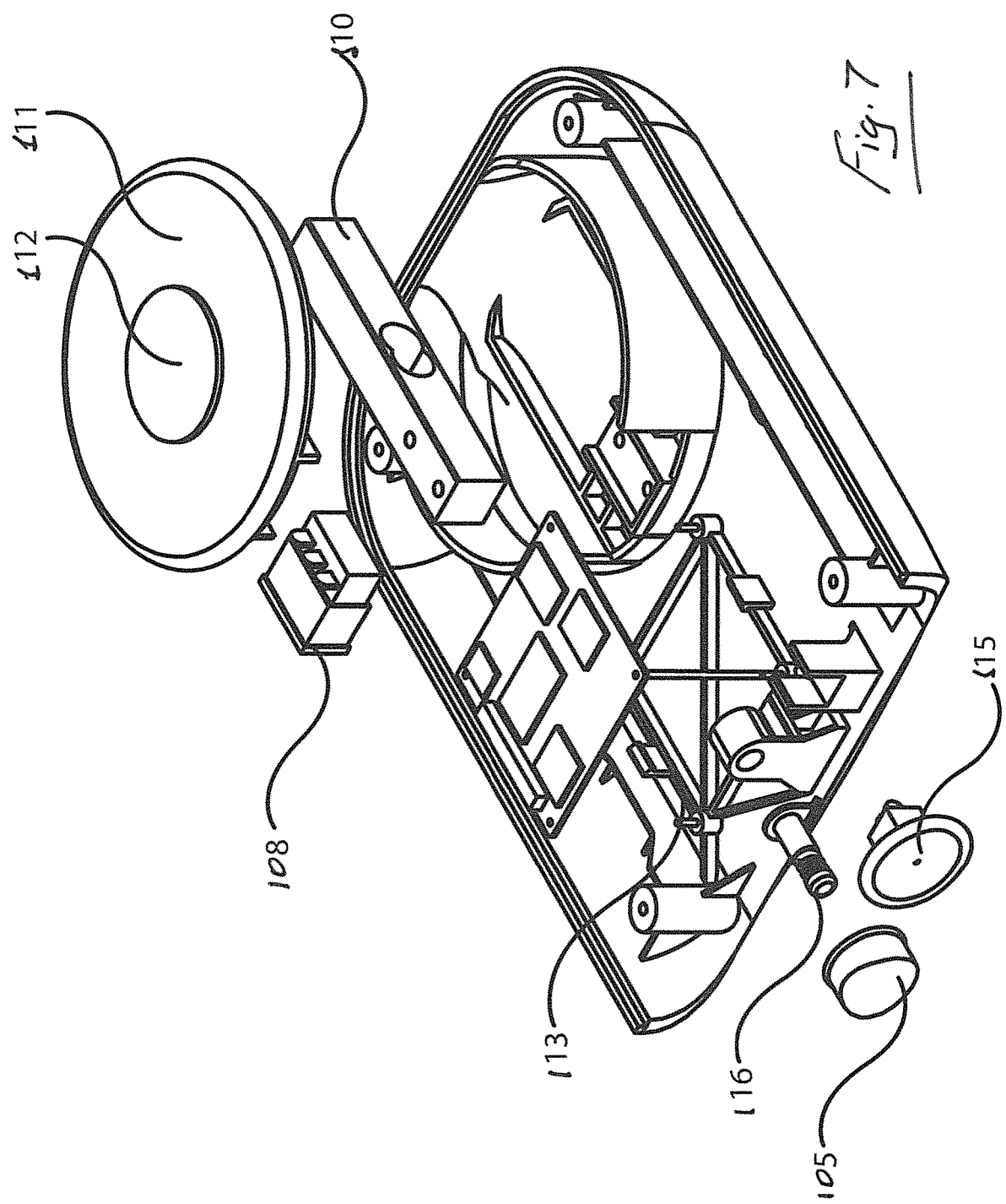
FIG. 7 is an exploded view of the docking station base.

FIGS. 5, 6 and 7 illustrate the internal components of the docking station. The docking station contains a circuit board 109, a strain gauge 110, a scales platform 111, a near field communication receiver 112, a rechargeable battery 114, audio output 115, and an activation switch 116. Inner ribs 113 provide stability for the internal components.

FIGS. 8 to 12 illustrate the interaction between the docking station 100, the inner flexible tube 106, the rim 118, the tube 119 and a nutritional pump 117 or food pod 200. It will be noted that in the case illustrated the pump 117 has a visual level indication 125. As seen in FIGS. 8 and 9, the pump 117 fits in the inner flexible sleeve 106, leaving part of it proud. The pump 117 is then guided by the tube 119 to the scales platform 111. In this position the pump is freely sitting or resting on the scales platform 111 which is connected to a strain gauge 110.

Figure 13:
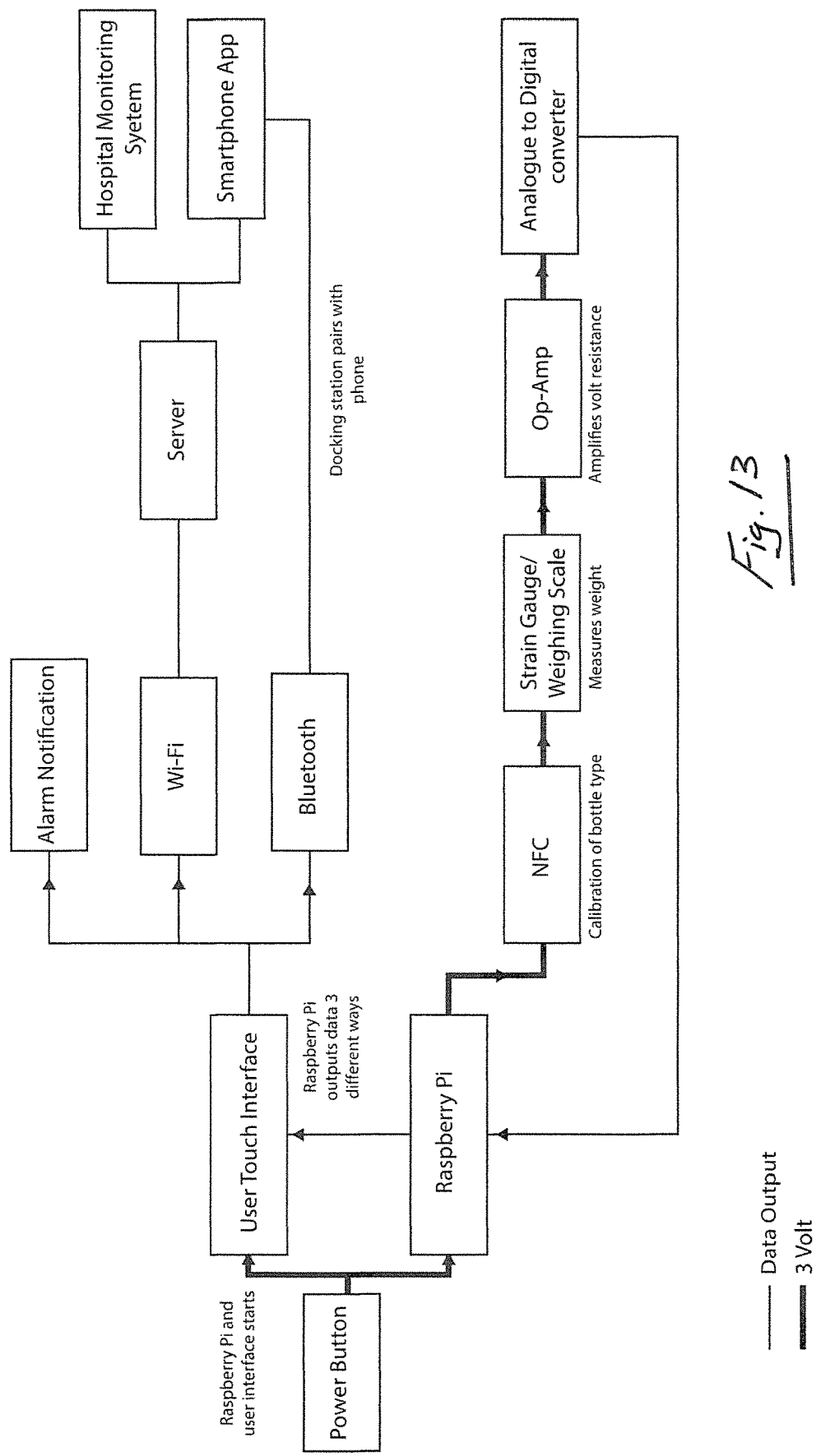
FIG. 13 is a flow diagram illustrating the operation of the docking station.

FIG. 13 is a flow diagram demonstrating how information from the docking station is used to provide notifications to the user and/or to other devices either local and/or remote.

The weight of a nutritional pump 117 or food pod is monitored, using a strain gauge 110, as it releases feed. The docking station detects if the pump has stopped releasing the feed due to an error (e.g. a kink in the line) or the feed pump being empty. The processor is programmed to analyse the weight data to determine the feeding pump status. For example, if the weight of the pump does not change for a pre-set amount of time, the processor will determine that there is blockage in the supply tubes and that the supply of feed has stopped.

As the strain gauge 110 weighs the nutritional feed being released it also detects if the pump stops releasing the feed (e.g. if the pump stays at the same weight for more than a set time such as 5 minutes). Following this, a notification or alert is given to the user. Information can also be displayed via a touch display interface 104 on the length of the feeding time that is left or how much nutritional feed is left in the pump by assessing the weight.

The docking station can be set up to locally alarm or send an alarm to a mobile, computer or program via Wi-Fi or Bluetooth. Wifi connection may be used in order to download updates or collect any relevant data. Bluetooth relay may be used so that notifications can be sent to other devices. The station may also have a pause feature that allows a user to lift the pump out and travel (e.g. to the bathroom) and to continue the feed on returning.

The invention allows patients using an enteral delivery system to be notified if there are any disruptions during a feed. It is particularly beneficial for night time feeding, however it is not limited to this. The pump/food pod and docking station are used in conjunction with each other in order to notify the user of any issues throughout the feed so that the issues can be rectified and the feed can be continued.

The docking station allows for static and remote monitoring and multiple notifications can be sent to carers or clinicians without disturbing the patient. Multiple users (patients, carers & clinicians) can be notified when the pump is blocked, kinked or emptied during a night feed.

The docking station can be remotely controlled such as "ON" or "OFF", "Clear Alarms", etc., by patient, carers or clinicians using the docking station app on their mobile phone/laptop/tablet. Communication from the docking station app on the mobile phone/laptop/tablet is usually but not limited to either Bluetooth/WiFi/Home network or network.

Near Field Communication (NFC) is used to identify the pump/food pod when it enters the docking station. An NFC interface circuit identifies the presence and volume of the feed pump in the docking station.

The system protects data on the NFC tag by encryption using a security algorithm, known as a secret key algorithm (sometimes called a "symmetric algorithm"). This is a cryptographic algorithm that uses the same key to encrypt and decrypt data when writing or changing the data on the tag. This prevents unauthorised data amendment.

Accordingly, any NFC-enabled phone or other device should be able to read the tag. However it is not possible to write over or add to the tag without the security credentials. NDEF (NFC Data Encoding Format) is a standardised way of encoding NFC tags in general.

The processor is calibrated for the weight of the product and this, coupled with the NFC data, is used to identify the type of feed, as the nutritional feed comes in many different consistencies e.g. one calories per/ml, two calories per/ml, 5 calories per/ml. This will allow the user to get feedback on calorie intake and keep track of their own feed data. The NFC facilitates pausing the docking station so it can be calibrated with a less than full pump. This is done by the docking station as it will read the expiry date, nutritional information (calories per/ml), overall feed time and the size of the pump be it 250 ml, 500 ml or a litre. The calibration will then take place as a result of subtracting the current weight when less than full off the feed from the total weight when full so show the remaining amount of feed, for example if a user needs to go to the bathroom during a night feed the user can then remove the pump from the docking station, bring the pump with them and when returning back to the docking station can place the pump back in to the docking station. The docking station can then re-calibrate how much feed has been used while the pump has been removed from the docking station and continue with the regular monitoring.

Figure 14:
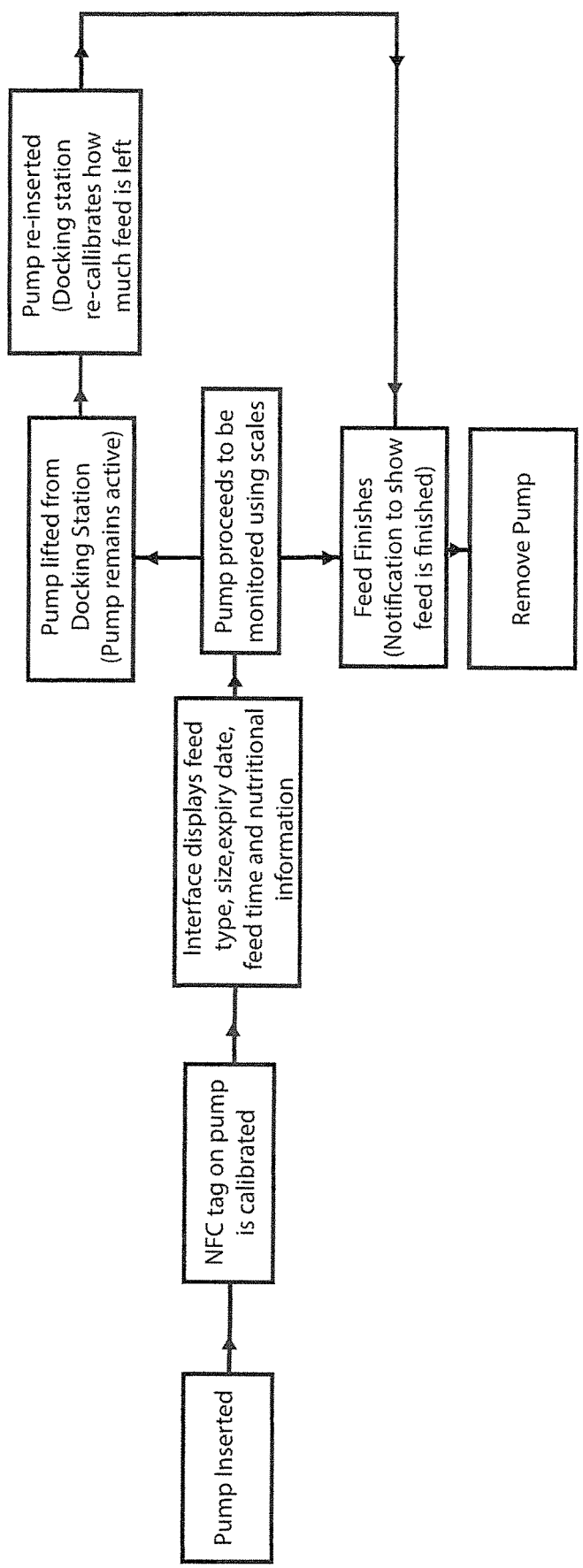
FIG. 14 is a flow diagram illustrating a typical use, in which the pump is removed and subsequently re-inserted.

FIG. 14 illustrates a typical use case. The pump/food pod is inserted and the docking station, using the NFC interface, reads the nutritional data including feed type, size expiry date, and feed time. The processor is calibrated to determine remaining nutritional data according to data read from the tag and the weight measurements. This data is displayed. The pump is monitored during use according to the scales, and when the feed finishes the pump is removed. If the pump is lifted from the docking station and subsequently re-inserted (such as by a patient needing to leave a room) the NFC interface is again used together with the weight measurements to determine nutritional data of what remains.

The docking station provides comprehensive information throughout a feed. Any errors that occur can be alerted to the user, hence any action that is required to rectify the issue can be done quickly and efficiently. This may be done without disturbing the patient.

Advantageously, the inner flexible tube provides a barrier between the pump and the docking station, resulting in better hygiene and the prevention of spillages.

Advantageously, in some cases the docking station is used to display the nutritional content of the feed to the user in terms of calories per ml, providing a standard means of measure of energy content and nutrition content. This is achieved by reading the NFC tag on the pod/pump showing the calories per/ml for each different feed type when full, thus showing the nutritional content for each feed be it 1,000 calories for one feed type or 2,000 calories for another.

Advantageously, in some cases the amount of feed remaining at any one time in the pod/pump can be displayed to the user.

The docking station may be considered to be "Plug & Play" so can be easily activated, paused and deactivated.

Advantageously, the invention has the benefits of allowing for 24-hour feeding monitoring, data collection for nutritional feed companies and logistics, and no moving parts resulting in minimal call out repairs It is envisaged that monitoring may be performed by means other than by weighing the feed. For example, a level sensor may be used to detect the level and rate of change of the level of the feed and this data can be processed in a similar way was weight data. Alternatively optical monitoring may be used.

The invention provides patients with an enteral feeding system that is comfortable, portable and adaptable to both therapy and lifestyle.

Figure 15:
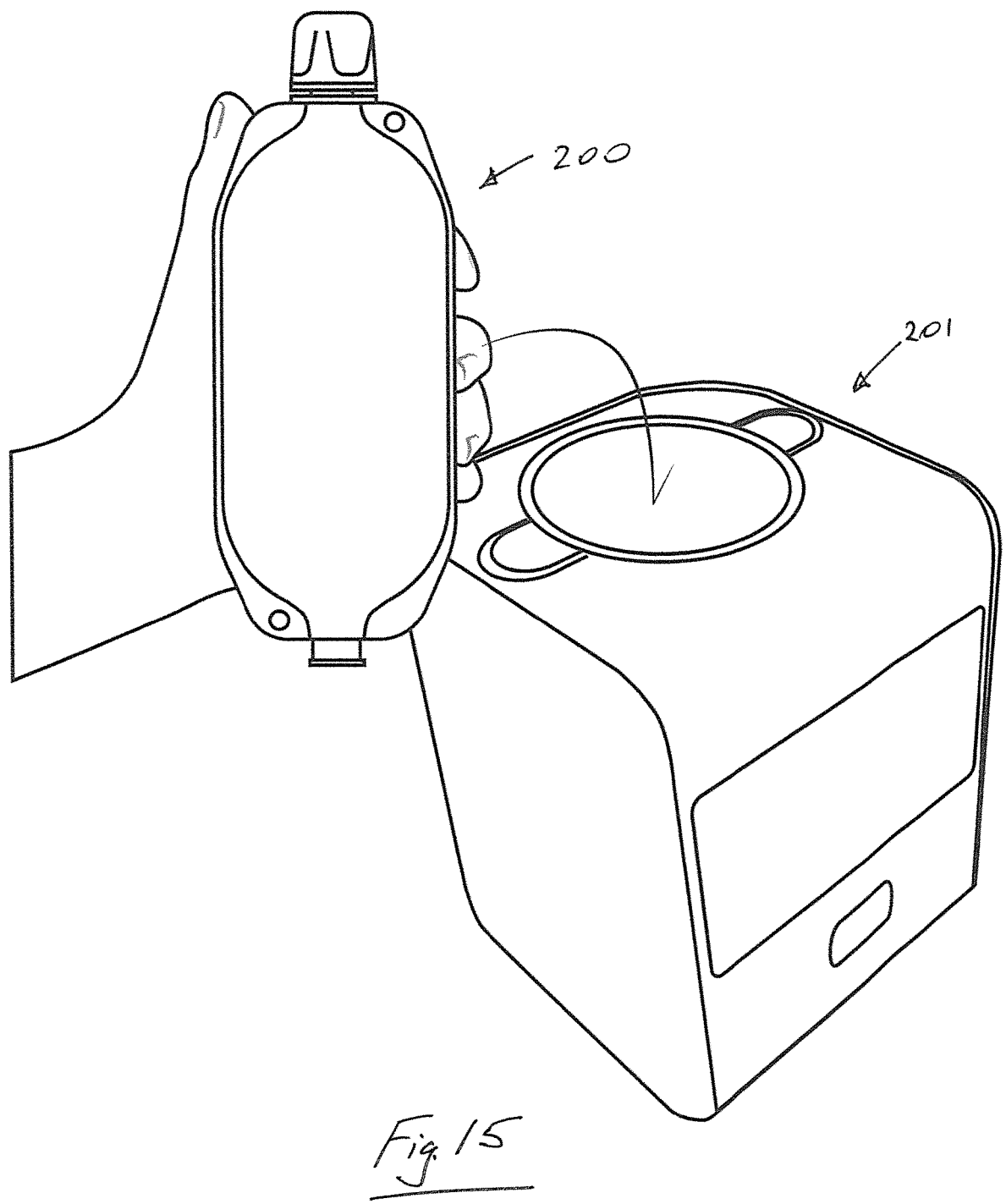
FIG. 15 illustrates a food pod being mounted to a docking station.

FIG. 15 illustrates a food pod 200 being mounted to a docking station 201 which is similar to that described above. The food pod 200 is described in more detail below.

Figure 16:
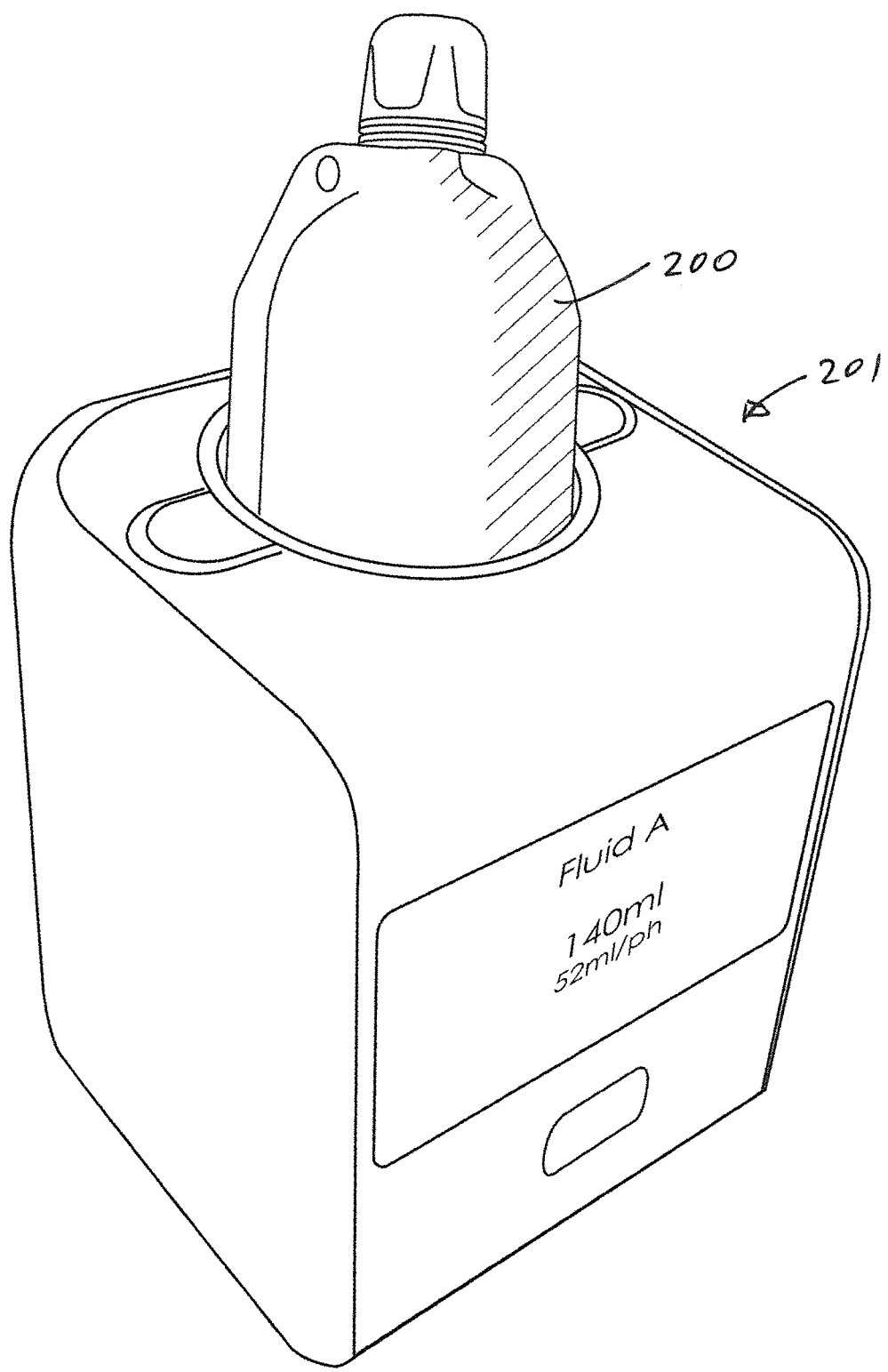
FIG. 16 is a view of a food pod and in position in the docking station.

FIG. 16 is a view of the food pod 200 in position in the docking station 201.

Figure 17:
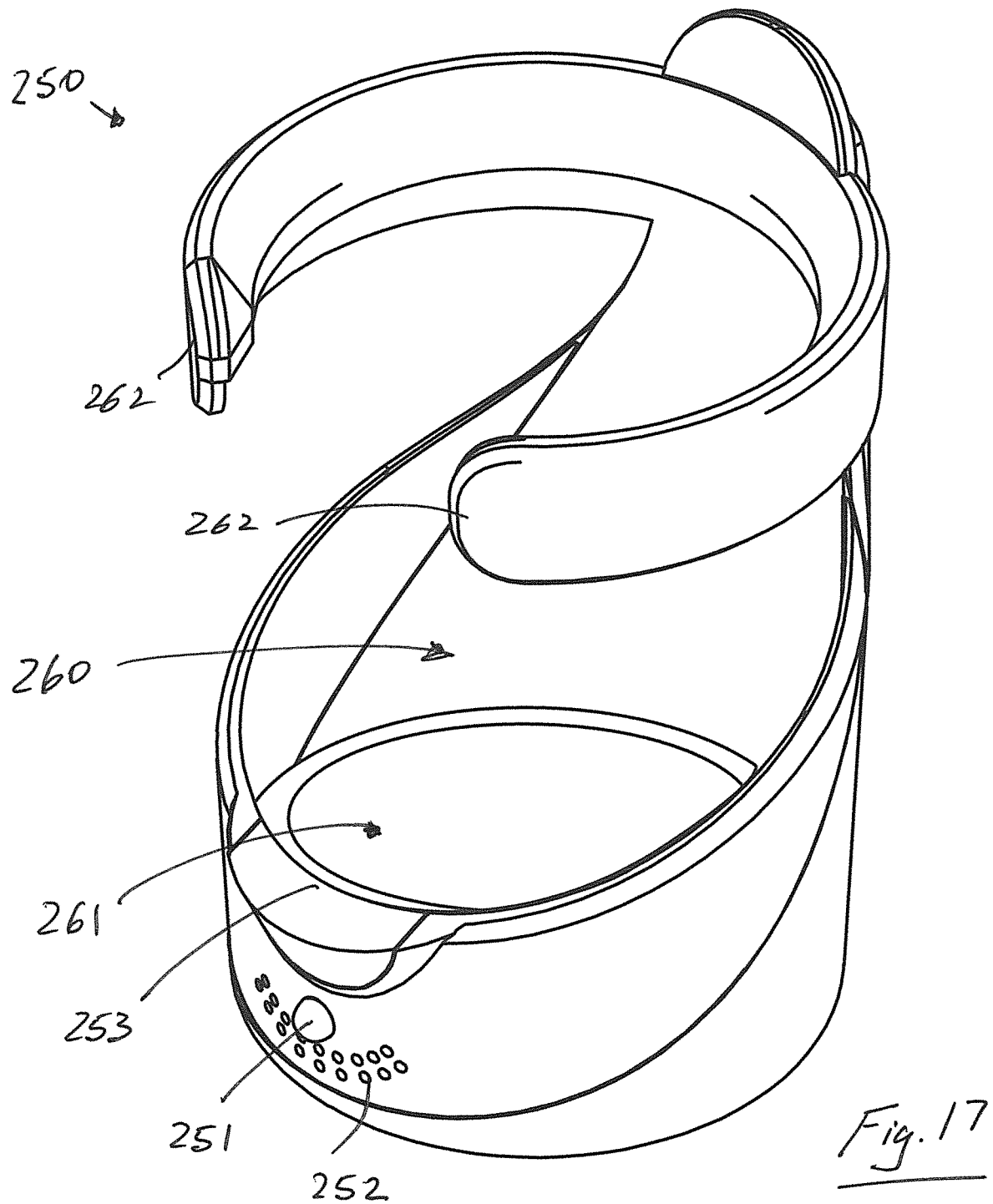
FIG. 17 is a perspective view of another docking station.

FIG. 17 is a perspective view of another docking station 250. In this case the docking station 250 has a user indictor. The user indicator may be a visible indicator such as a light 251. An audible indicator may also be provided through a speaker 252. There is also an on/off switch 253.

The docking station 250 comprises a housing defining a receiver 260 for an enteral food pod 200. The housing comprises a base 261 in which a weighing device (such as a strain gauge), a processor and associated elements are mounted. The food pod 200 is supported on a platform 261 which is engaged by the bottom of the food pod for weighing of the pod. The housing has an open ring housing arms 262 which assist in retaining and aligning the pod 200 in situ.

Figure 18:
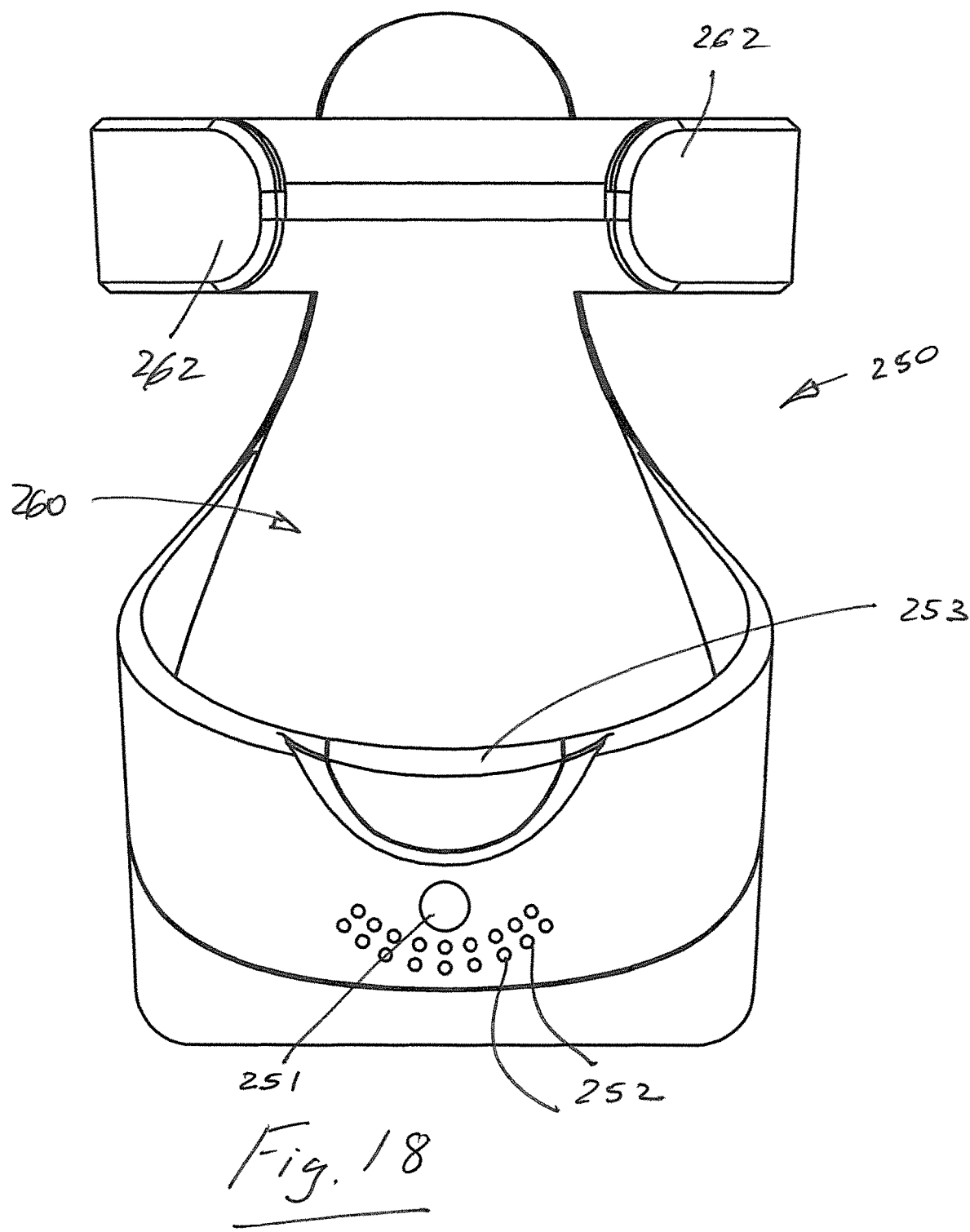
FIG. 18 is a front view of the docking station of FIG. 17.

FIG. 18 is a front view of the docking station 250 of FIG. 17.

Figure 19:
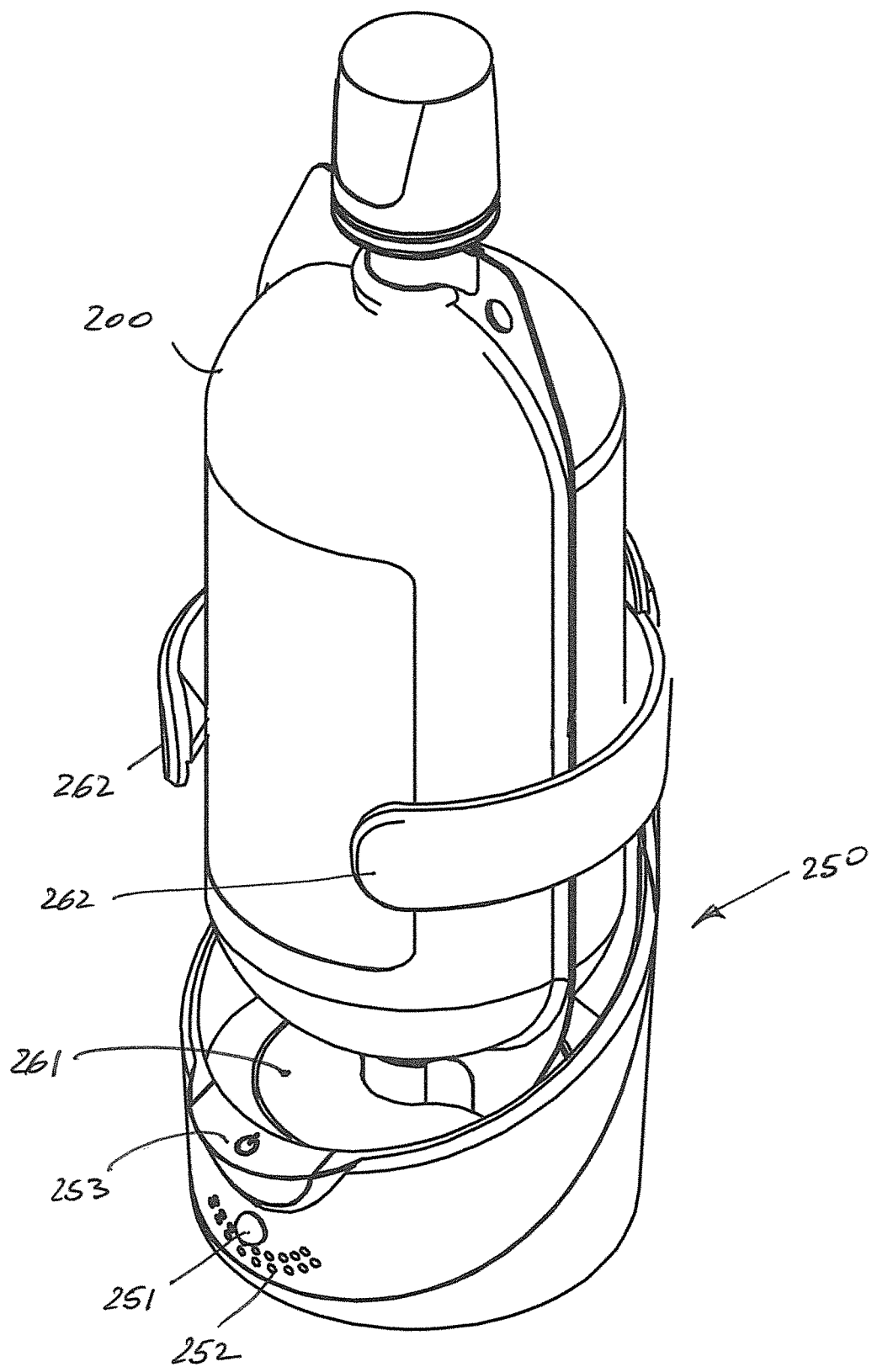
FIG. 19 is an isometric view of the docking station of FIGS. 17 and 18 with a food pod positioned on a platform.

FIG. 19 is an isometric view of the docking station 250 of FIGS. 17 and 18 with a food pod 200 positioned on the platform 261.

Figure 20:
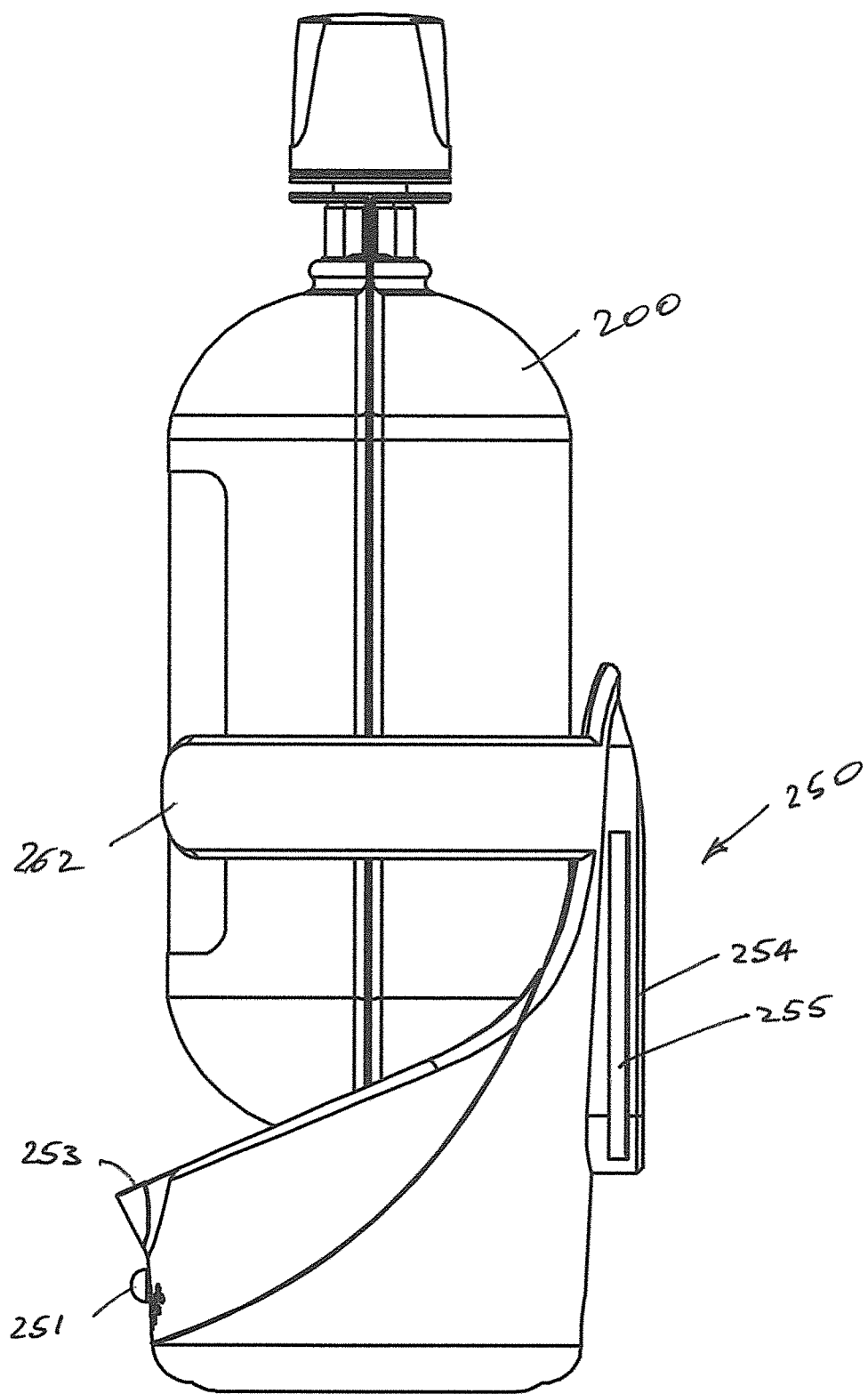
FIG. 20 is a side view of the docking station and the food pod of FIG. 19.

FIG. 20 is a side view of the docking station 250 and the food pod 200 of FIG. 19. The station includes a mounting bracket 254 with a slot 255 for mounting to a support such as a pole.

Figure 21:
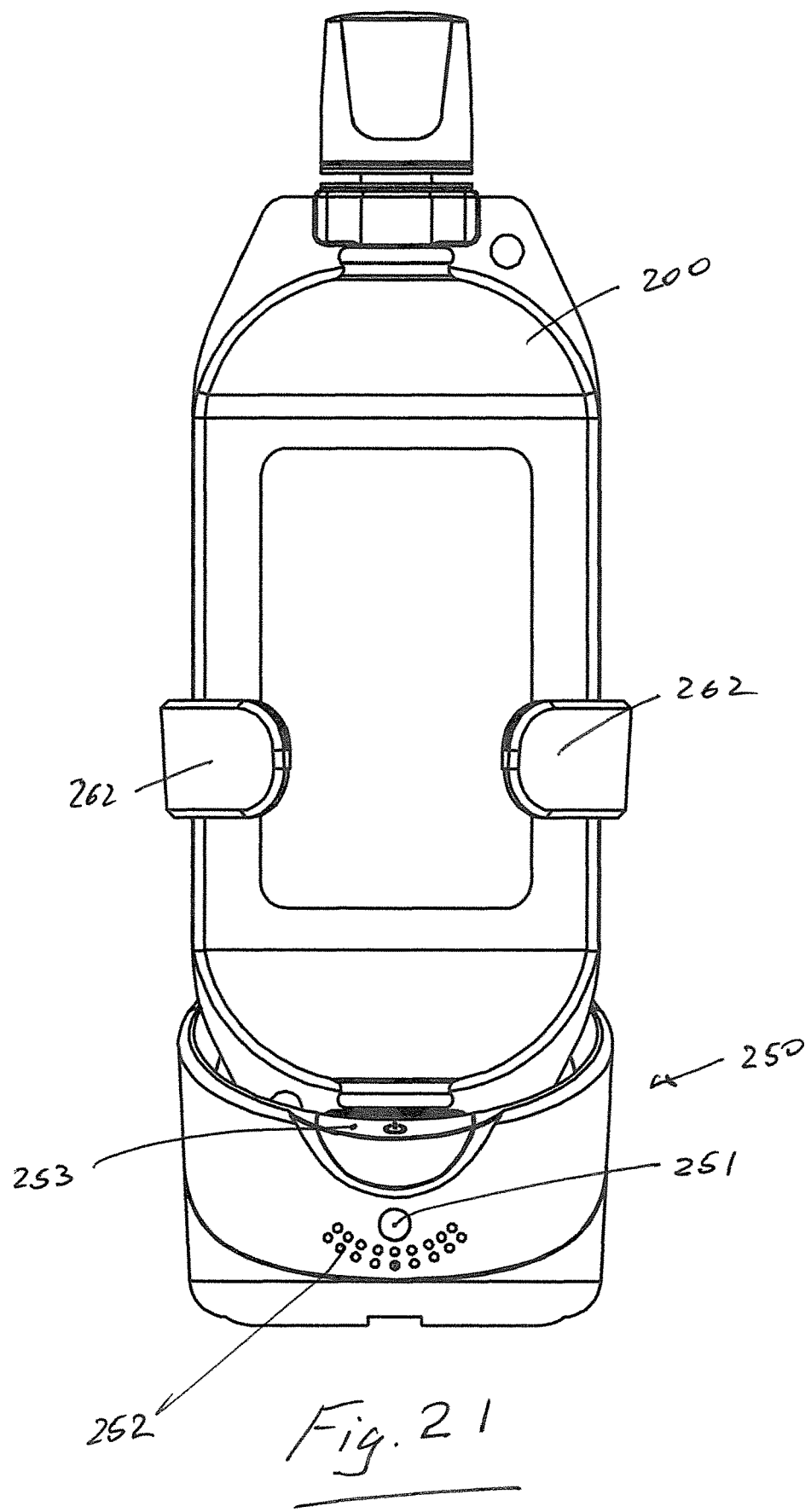
FIG. 21 is a front view of the docking station and the food pod of FIG. 19.

FIG. 21 is a front view of the docking station 250 and the food pod 200 of FIG. 19.

Figure 22:
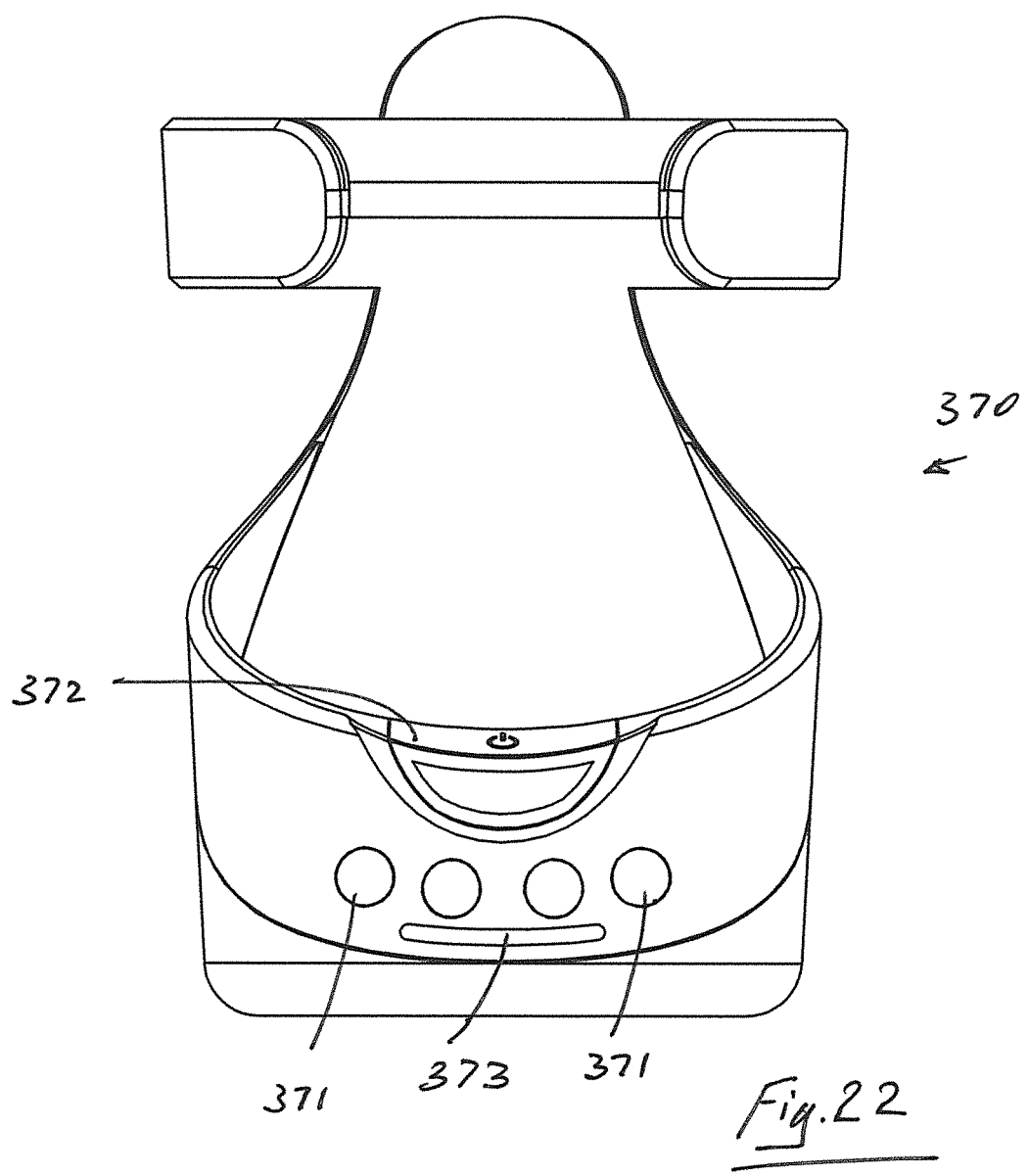
FIG. 22 is a front view of another docking station with a different interface to the docking station of FIGS. 17 to 21.

FIG. 22 is a front view of another docking station 370 with a different interface to the docking station of FIGS. 17 to 21. The interface in this case has a number of buttons 371 on the lower face and an on/off switch 372 on the edge. The buttons may, for example, be used by the user to adjust volume, set silent mode, set Bluetooth, set WiFi and the like. There is also a speaker 373 for audio output.

Figure 23:
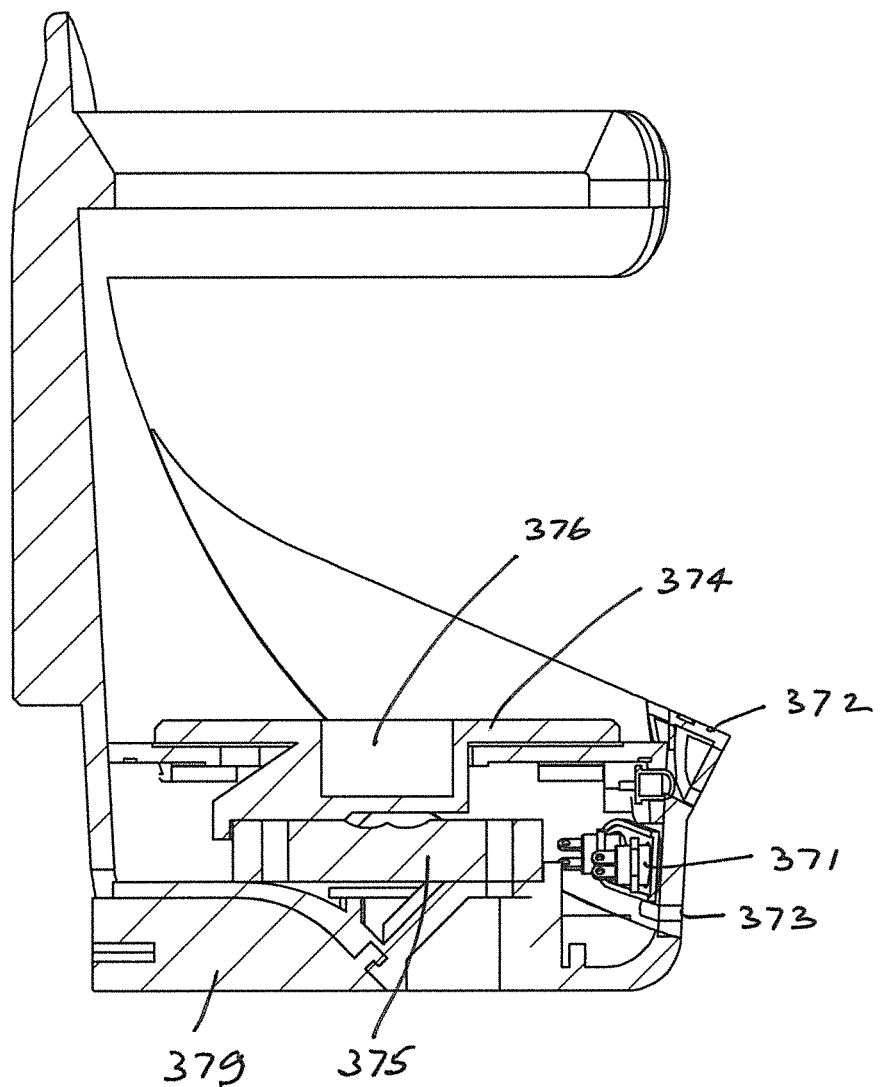
FIG. 23 is a section of the docking station of FIG. 22 from a side view.

FIG. 23 is a section view on the line A-A in FIG. 22.

Figure 24:
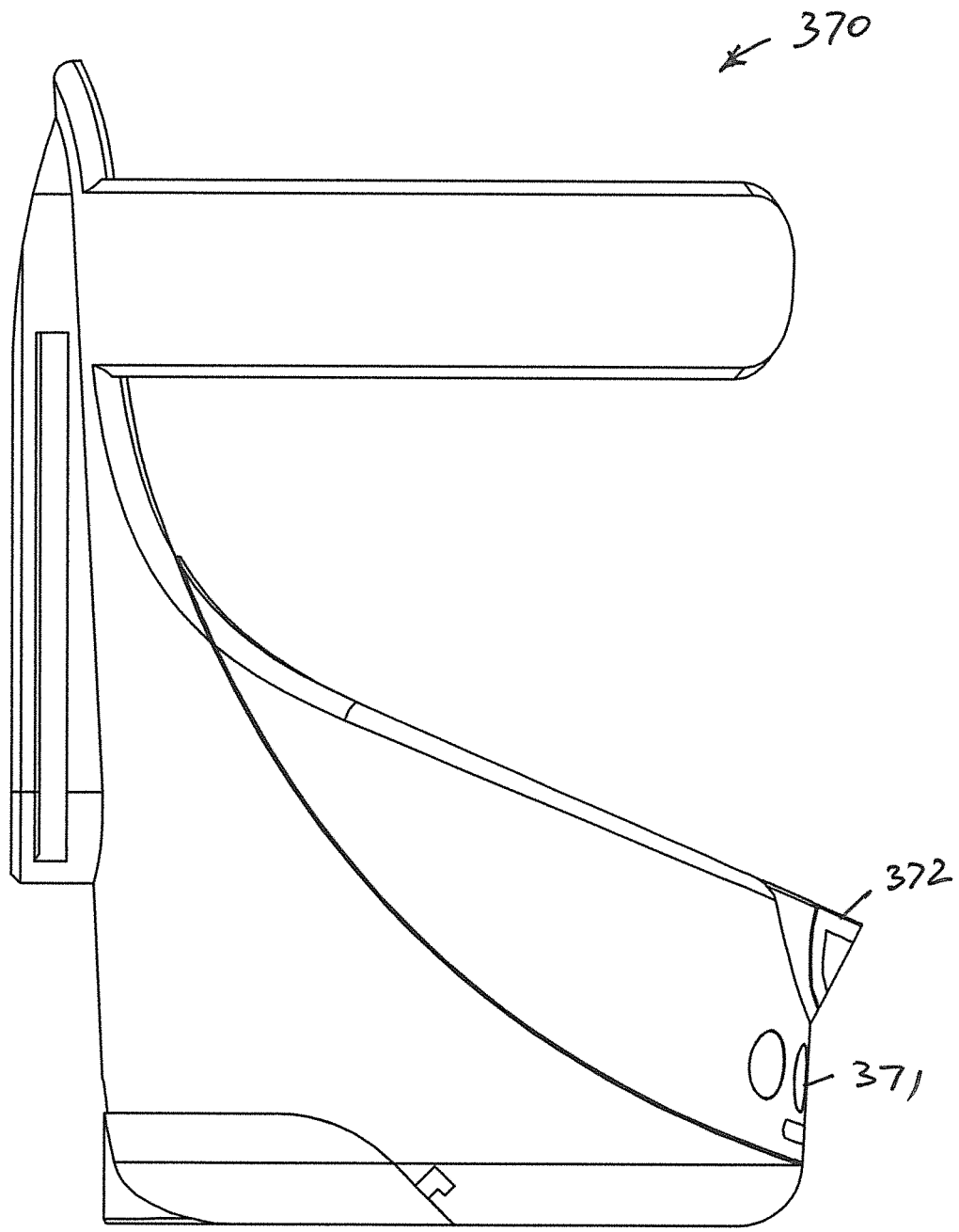
FIG. 24 is a side view of the docking station of FIG. 22.

FIG. 24 is a side view of the docking station 370 of FIGS. 22 and 23.

Figure 25:
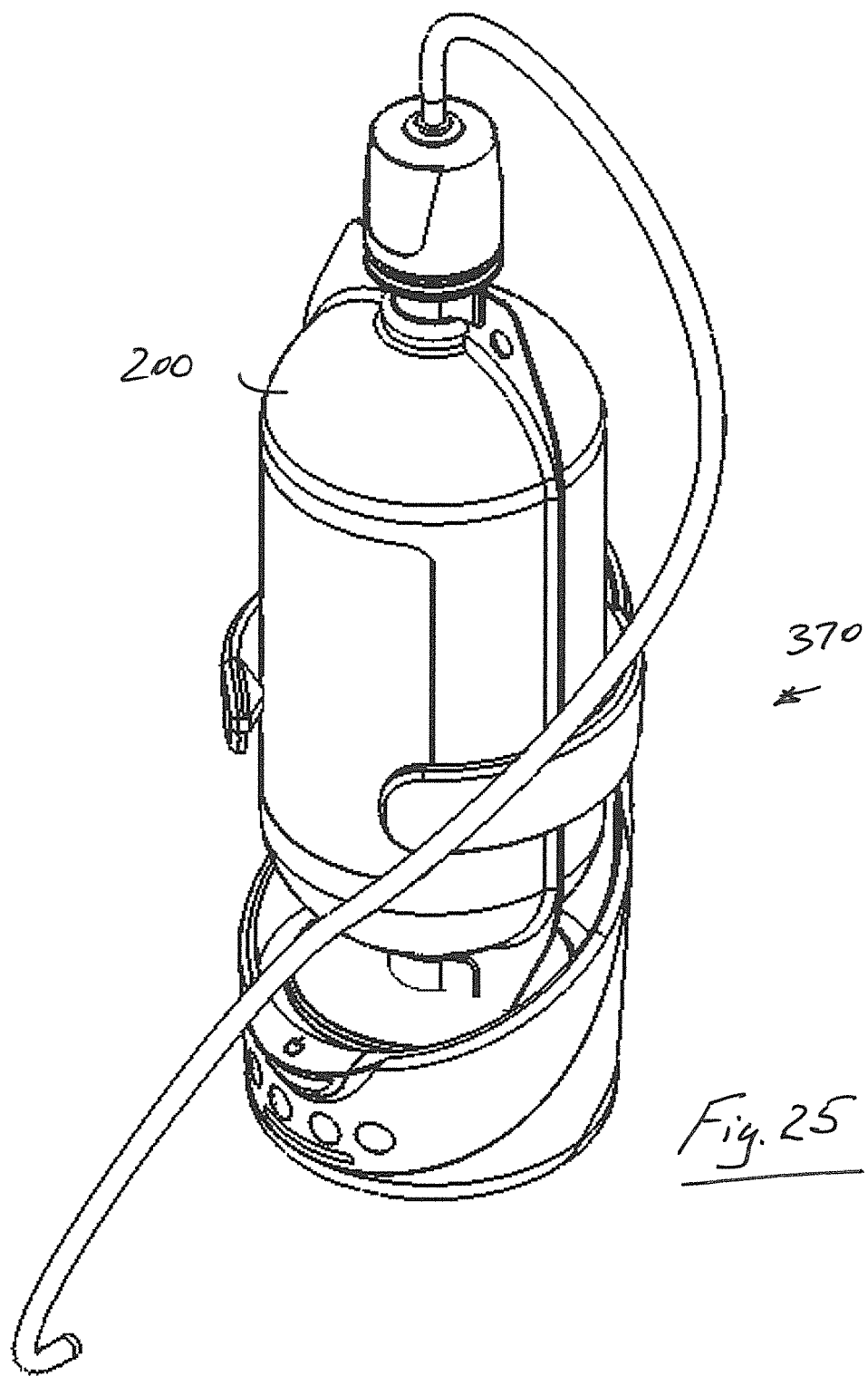
FIG. 25 is an isometric view of the docking station of FIGS. 22 to 24 with a food pod in position on a weighing platform.

FIG. 25 is an isometric view of the docking station 370 of FIGS. 22 to 24 with a food pod 200 in position on a weighing platform.

FIG. 26 is a cross section of the food pod 200 and docking station 370 from a side view.

Figure 27A:
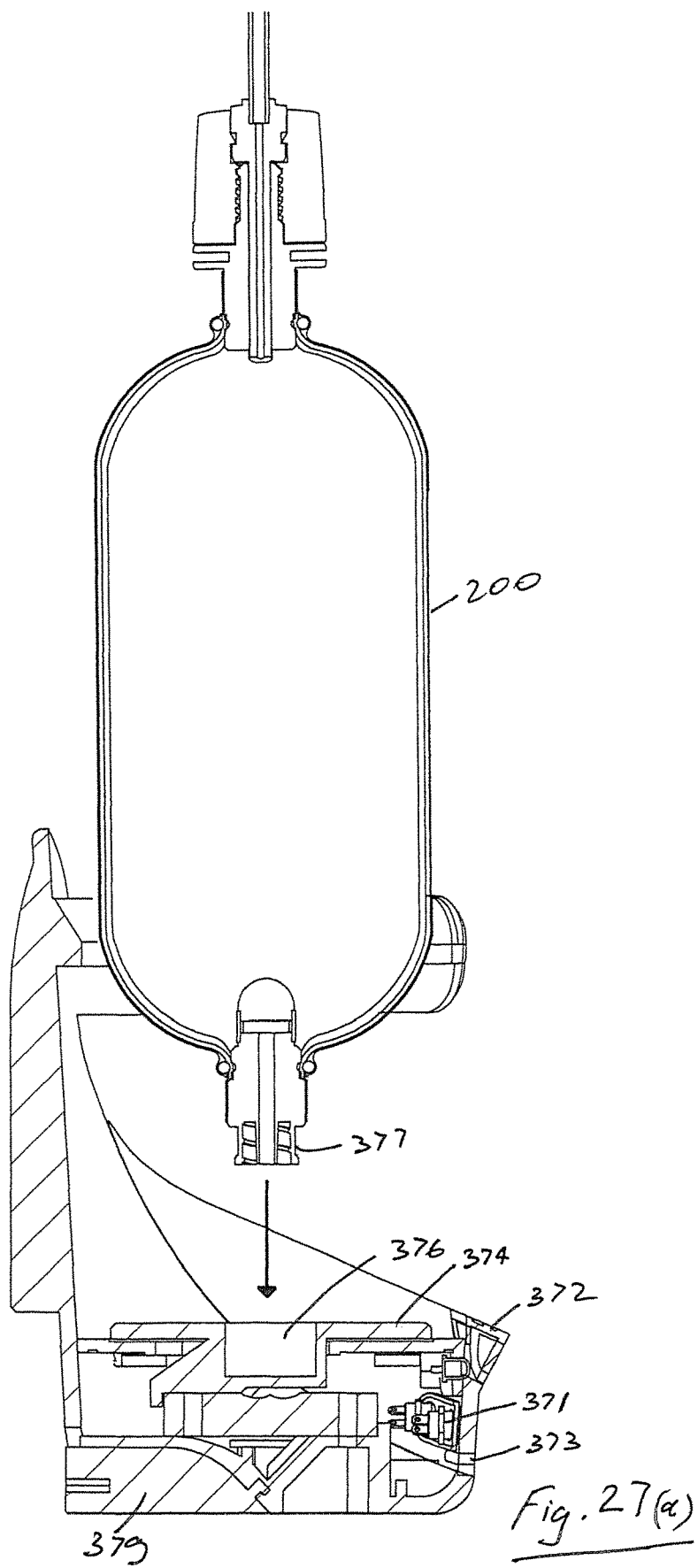
FIGS. 27(a) and 27(b) show an intermediate stage of the mounting of the food pod to the docking station.
Figure 27B:
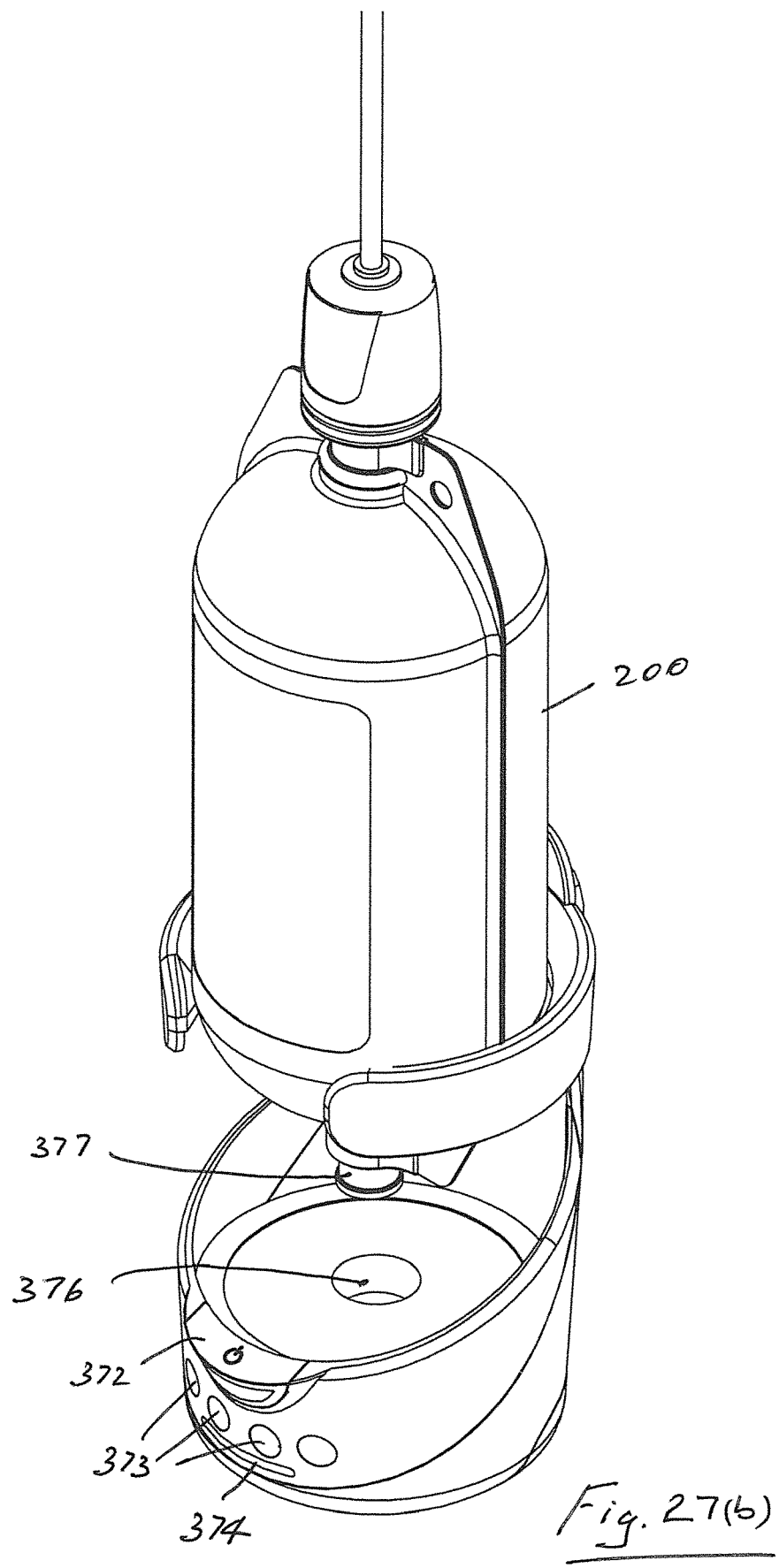

FIGS. 27(a) and 27(b) show an intermediate stage of the mounting of the food pod 200 to the docking station.

Referring in particular to FIGS. 23, 26 and 27(a), the weight platform 374 and strain gauge 375 are shown. It will be noted that in this case the platform 374 has a recess 376 into which a part 377 at the base of the food pod 200 is inserted. This stabilises the mounting of the food pod 200 to the docking station 370. FIGS. 25 to 27 in particular illustrate the engagement of the food pod base part 377 in the recess 376 of the platform 374. The docking station also has a removable buttery pack 379.

Figure 28:
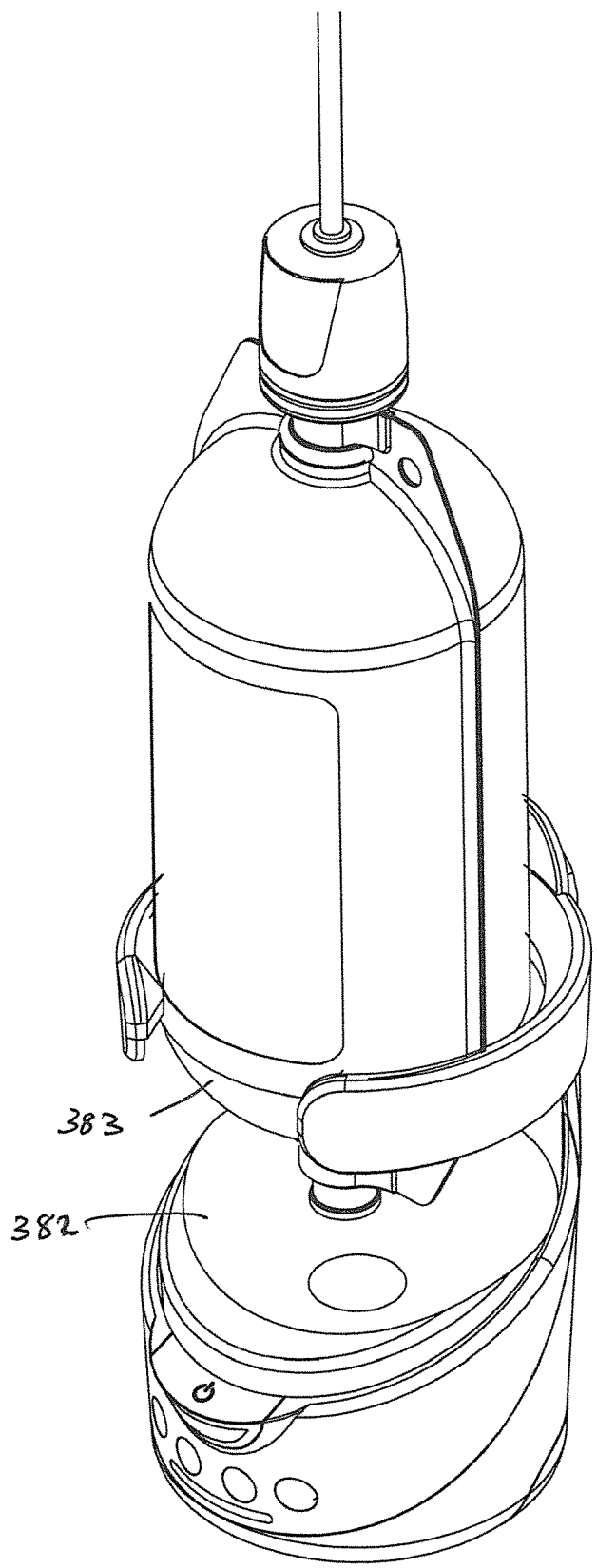
FIGS. 28(a) and 28(b) show docking stations with alternative support platforms.

FIGS. 28(*a*) and 28(*b*) show docking stations with alternative support platforms. FIG. 28(*a*) shows a generally flat weight platform 380. Such a platform is useful for engagement with a food pod having a flat base or base portions 381 such as the gusset-type base of the food pod described below with reference to FIGS. 78 to 80.

FIG. 28(*b*) illustrates a support platform 382 with a cup shape for receiving a food pod with a curved base 383.

Figure 29A:
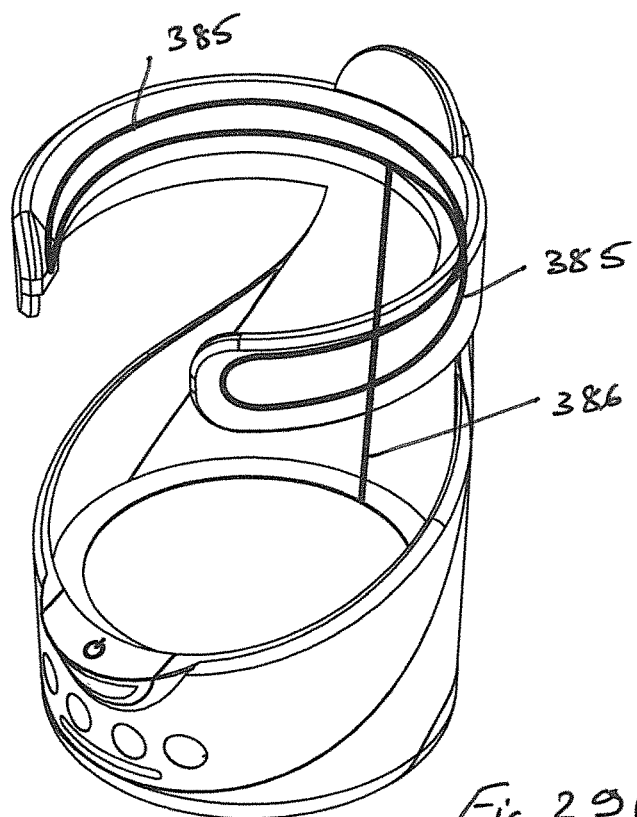
FIGS. 29(a) and 29(b) show an NFC reader within the arms of the housing of the docking station and transferring the data collected to a processor.
Figure 29B:
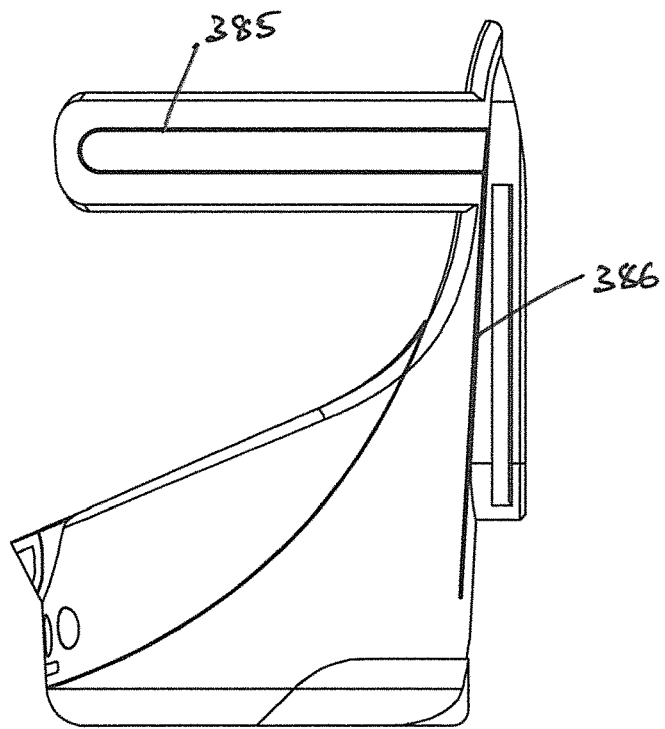
Figure 29C:
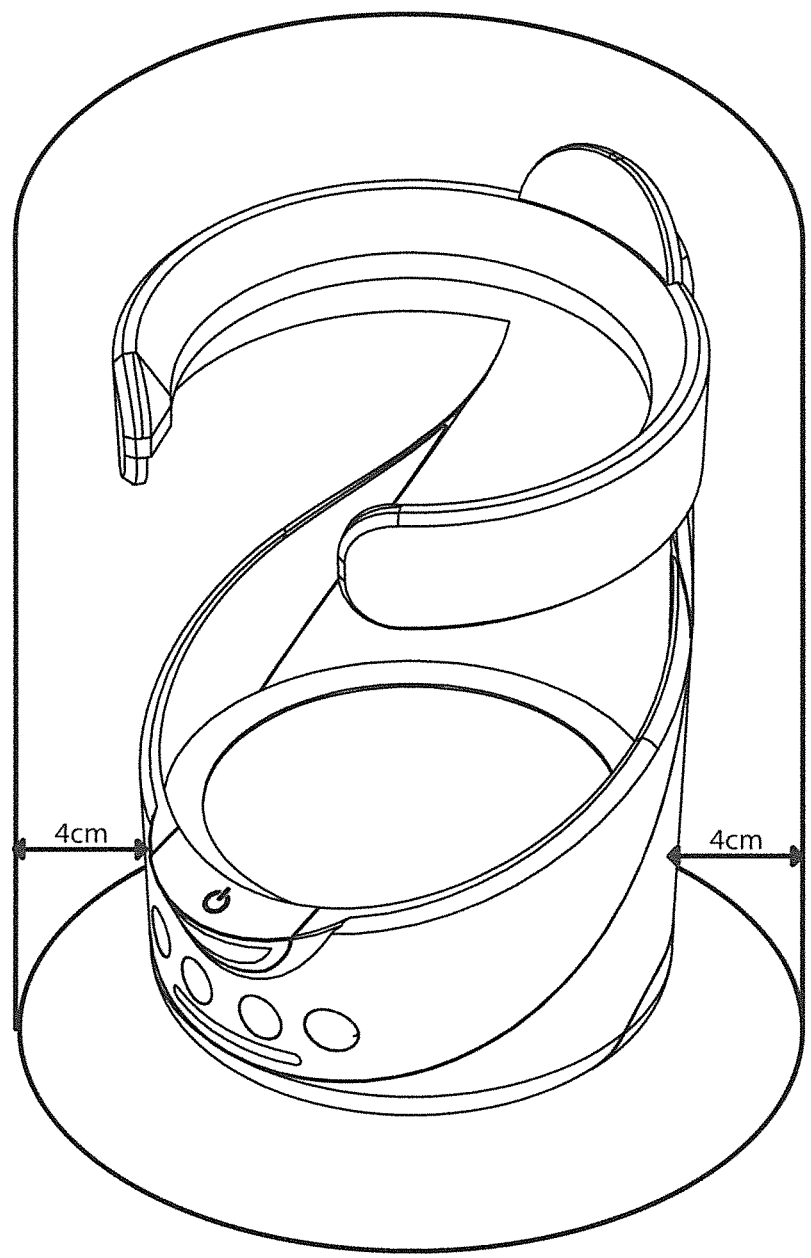
FIG. 29(c) is a diagram showing a space envelope around the docking station where the NFC reader may register the NFC tag.

FIGS. 29(*a*) and 29(*b*) illustrate an NFC reader 385 which in this case is located within the arms of the pod receiver. Data collected may be transferred to the processor along line 386.

FIG. 29(*c*) diagrammatically illustrates a space envelope (such as a 4 cm envelope) around the docking station where the NFC reader may register the NFC tag.

Figure 30A:
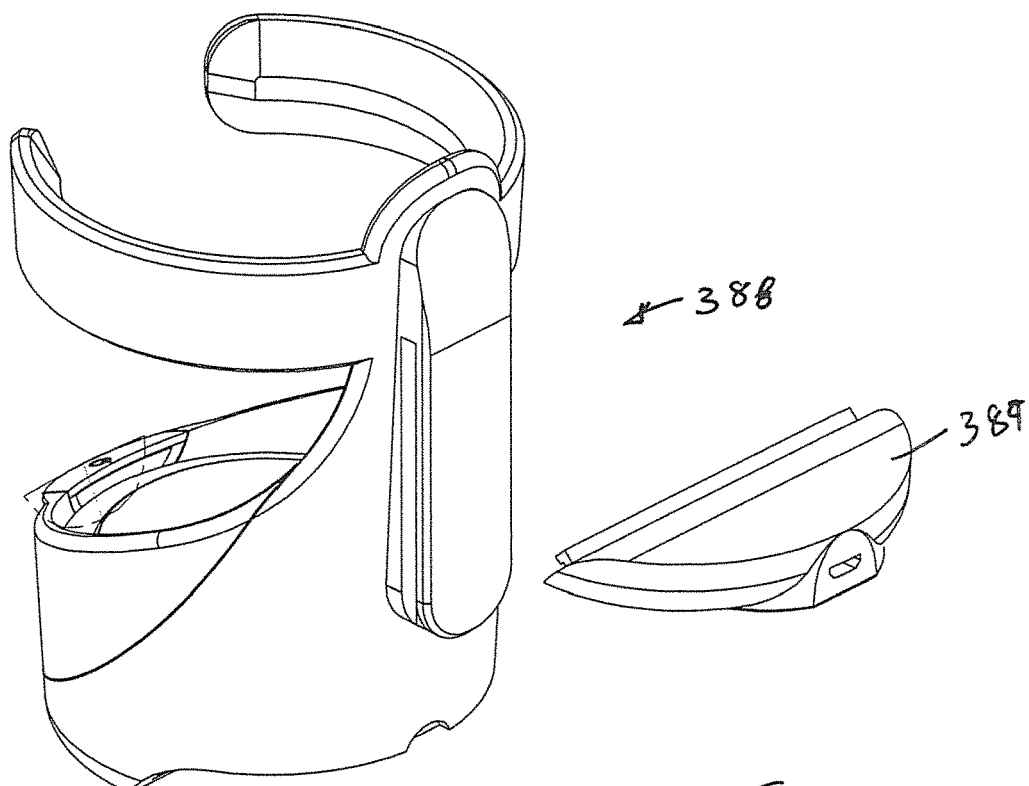
FIGS. 30(a) and 30(b) are images of a docking station with a removable battery pack.
Figure 30B:
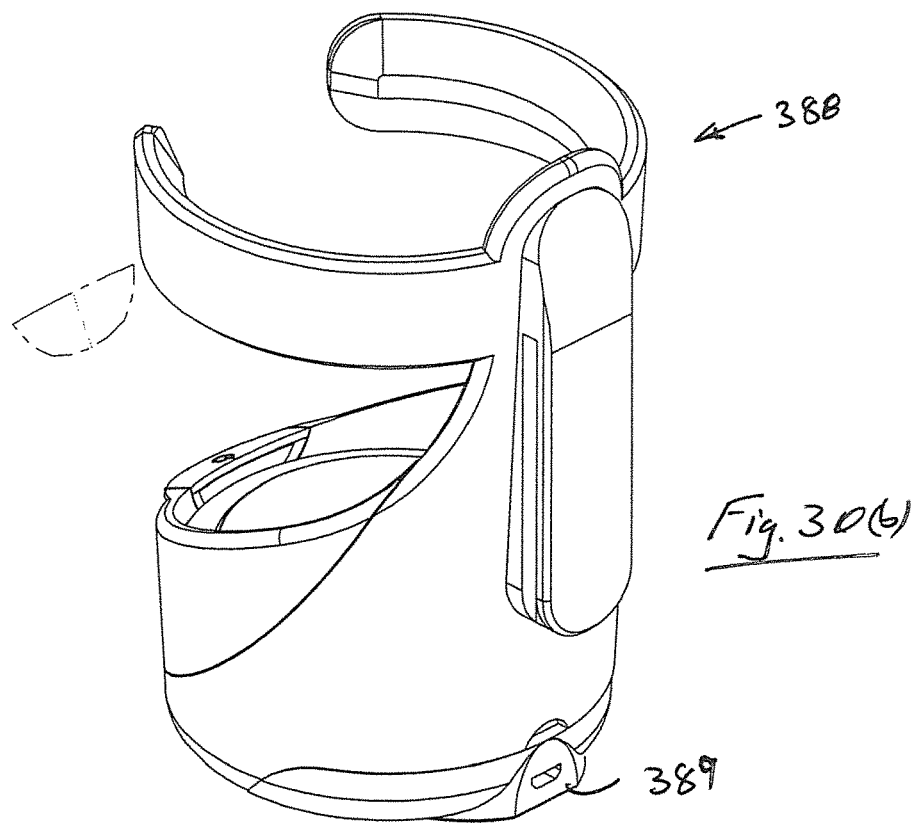

FIGS. 30(*a*) and 30(*b*) are images of a docking station 388 with a removable battery pack 389.

Figure 31A:
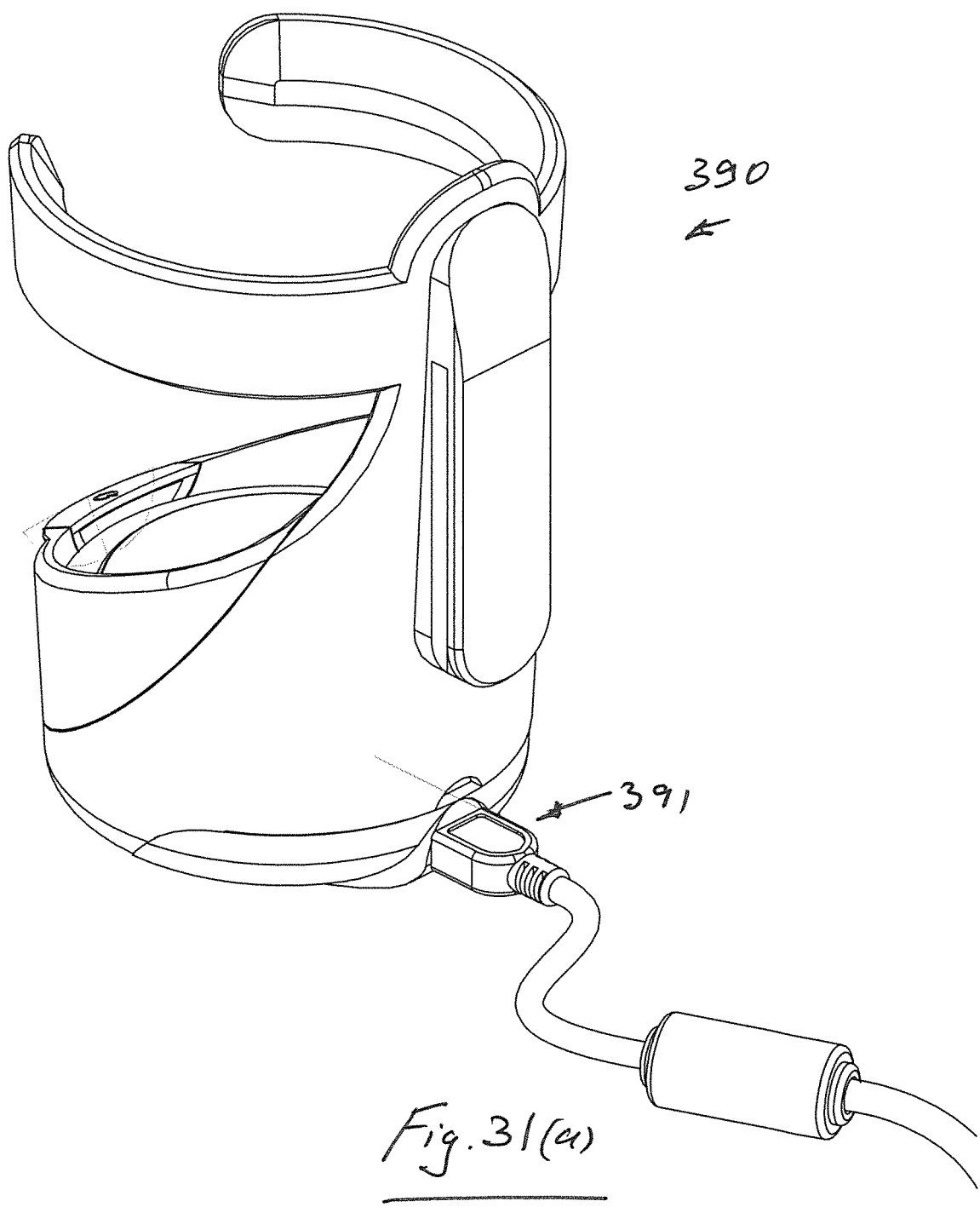
FIG. 31(a) is a perspective view of a docking station being charged using a standard micro USB port.

FIG. 31(*a*) is a perspective view of a docking station 390 having a charging port 392 which is used to charge the device using a standard micro USB 391.

FIG. 31(*b*) is another view of the docking station 390 of FIG. 31(*a*) with the charger 391 removed.

Figure 32:
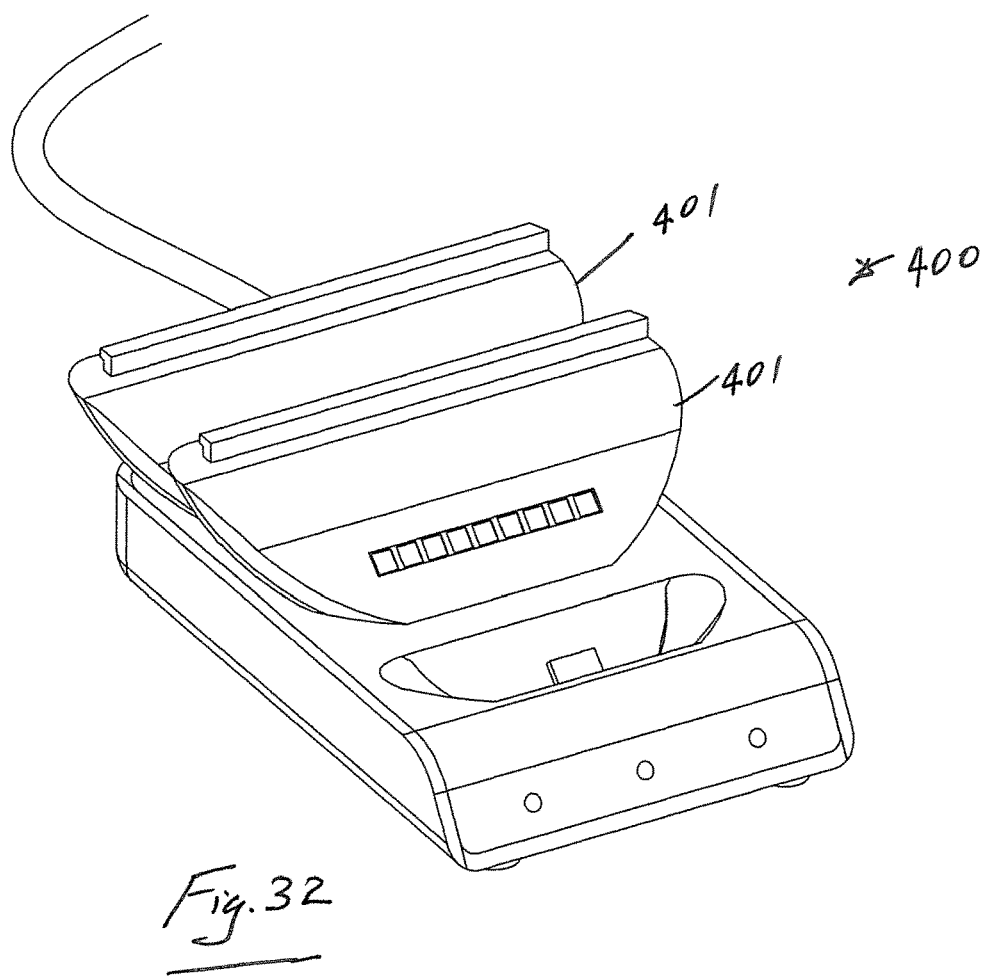
FIGS. 32 and 33 are images of a docking station with multiple plug-in battery packs.
Figure 33:
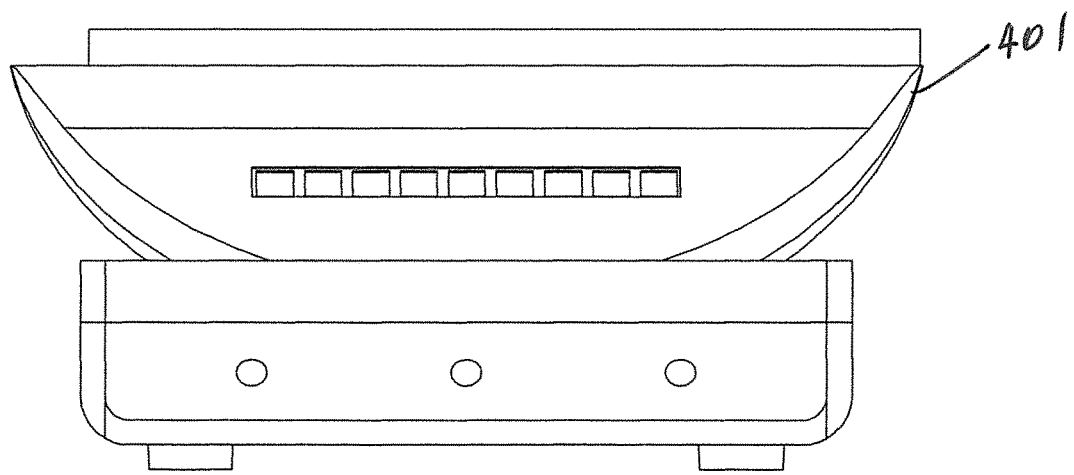

FIGS. 32 and 33 are images of a docking station 400 with multiple plug-in battery packs 401. Such a device may be used in a setting such as a hospital in which multiple docking stations are used.

Figure 34A:
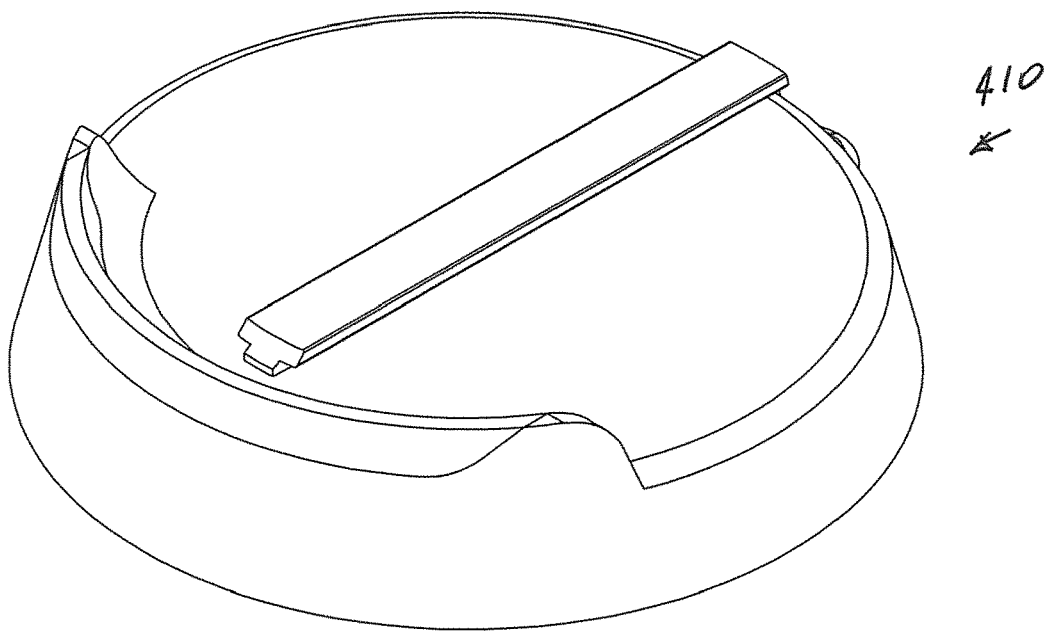
FIGS. 34(a) and 34(b) are images of a stand for a docking station.
Figure 34B:
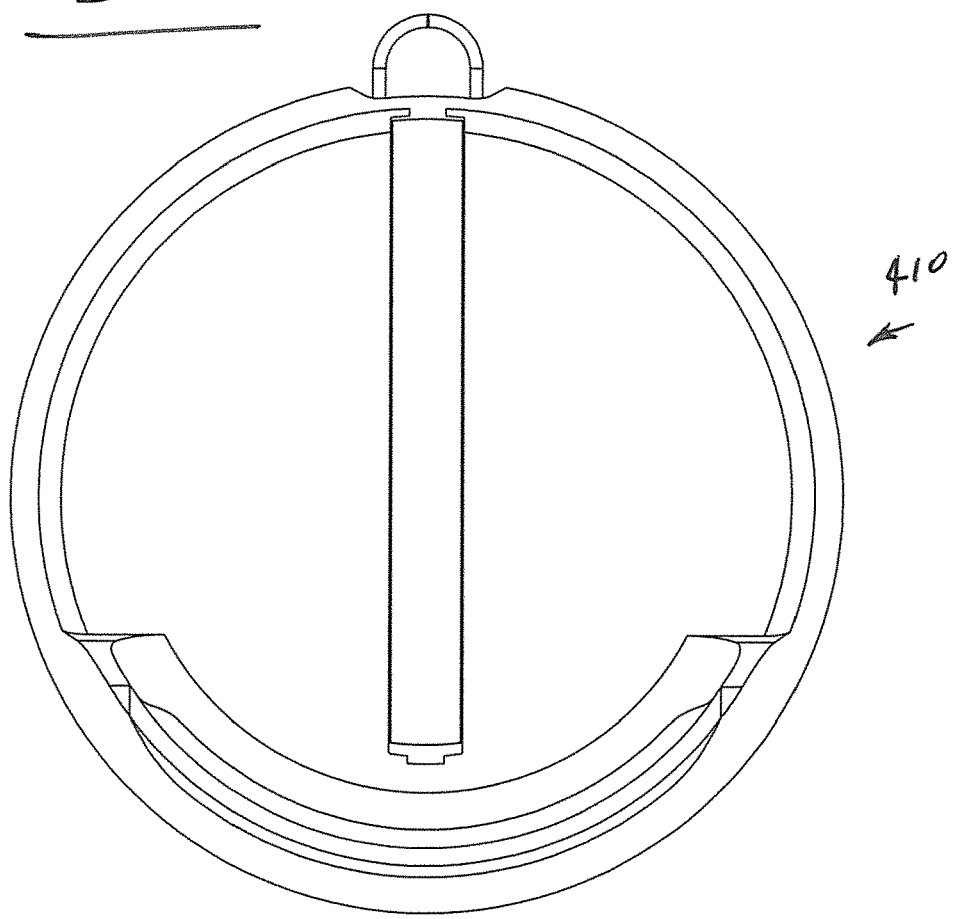
Figure 35A:
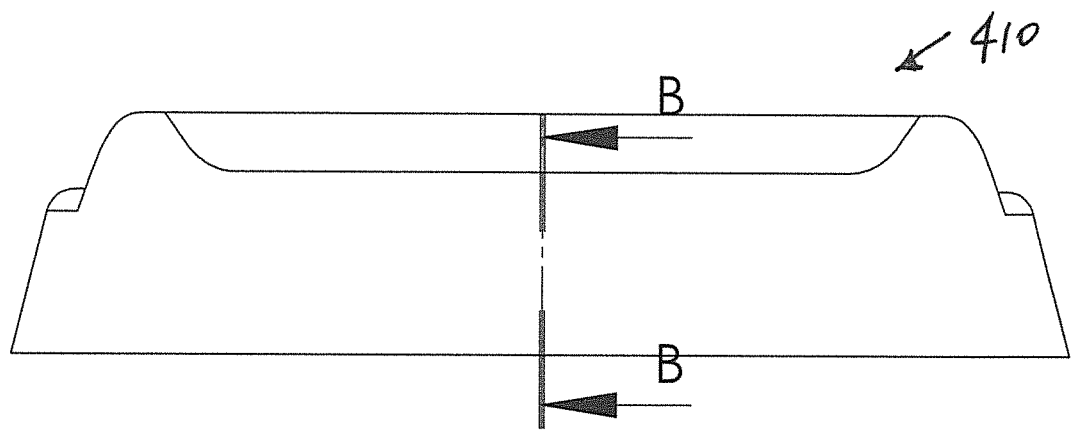
FIG. 35(a) is a side view of the stand of FIG. 34.
Figure 35B:
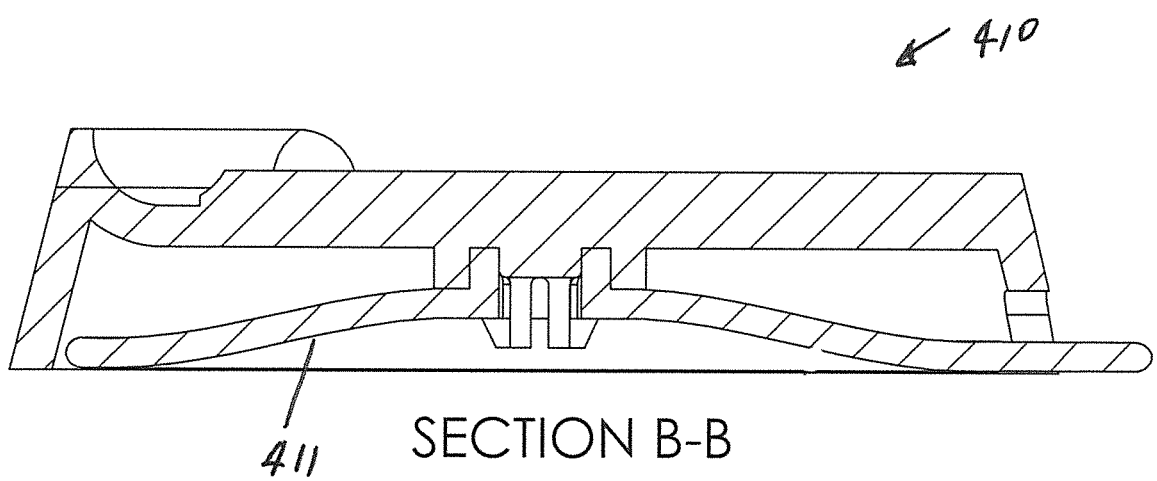
FIG. 35(b) is a cut section on the line BB in FIG. 35(a)

FIGS. 34(*a*) and 34(*b*) are images of a stand 410 for a docking station. The stand 410 can be placed on the table to stop the docking station from falling over or being dragged from side to side. FIG. 35(*a*) is a side view of the stand 410 of FIG. 34. FIG. 35(*b*) is a cut section BB on FIG. 35(*a*) and exposes a suction cup 411 which is used to hold the stand firmly in place.

Figure 36:
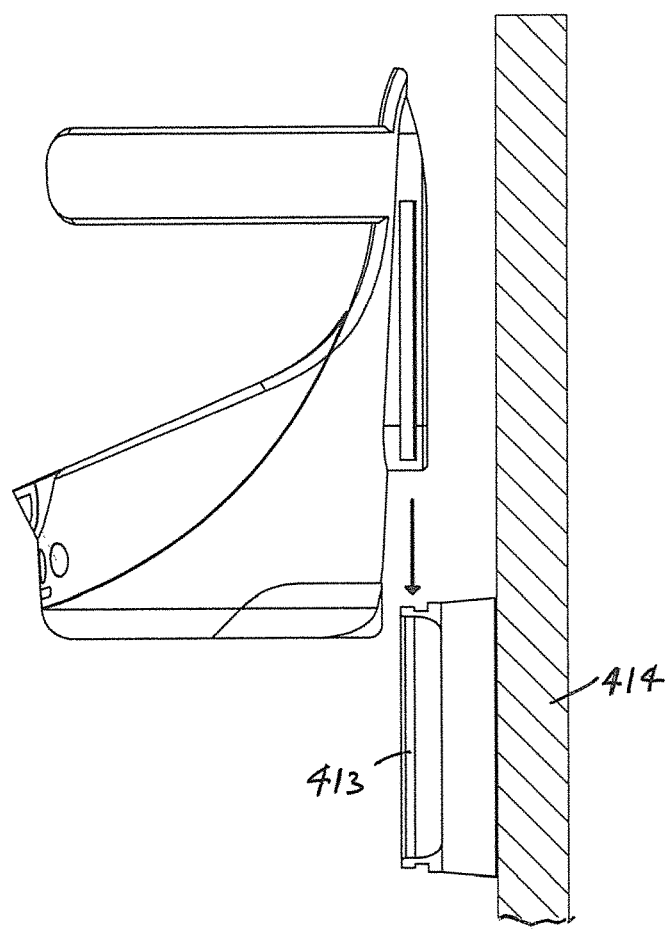
FIGS. 36 and 37 show a suction cup that can be attached to the back of the docking station and placed on a flat surface such as a wall.
Figure 37:
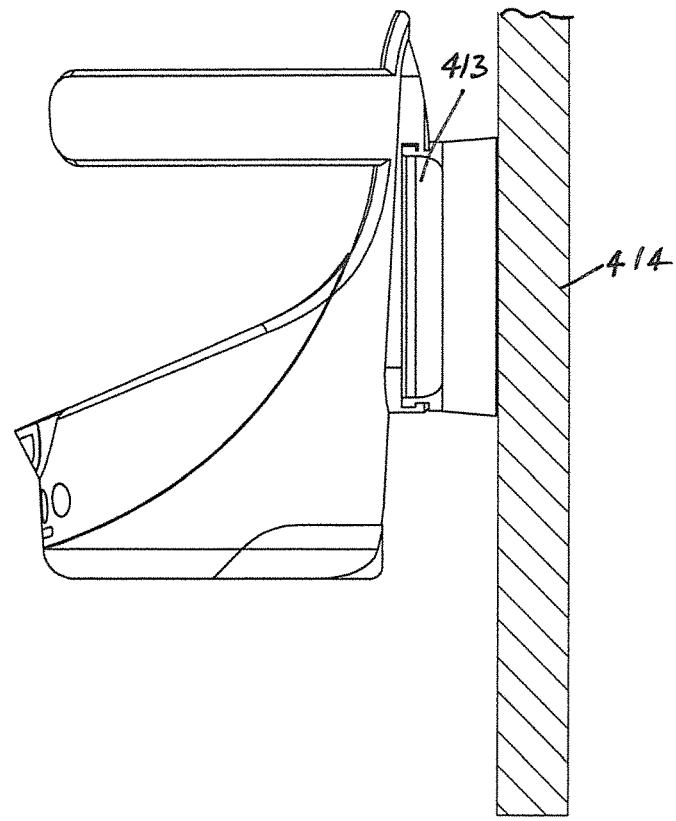

FIGS. 36 and 37 show a suction cup 413 that can be attached to the back of the unit and placed on a vertical surface such as a wall 414.

Figure 38:
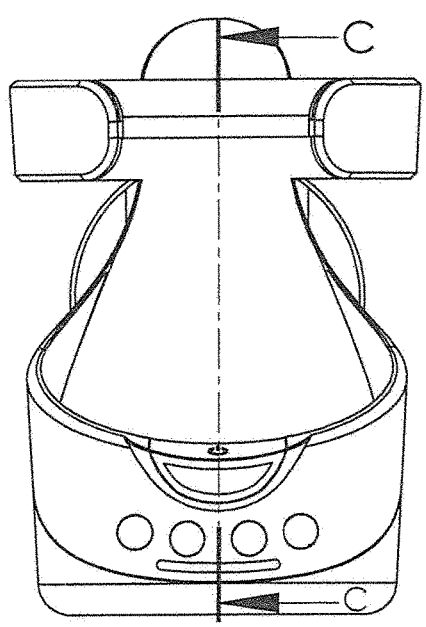
FIG. 38 is a front view and FIG. 39 is a cut section CC of the station and suction cup when attached to a flat vertical surface.
Figure 39:
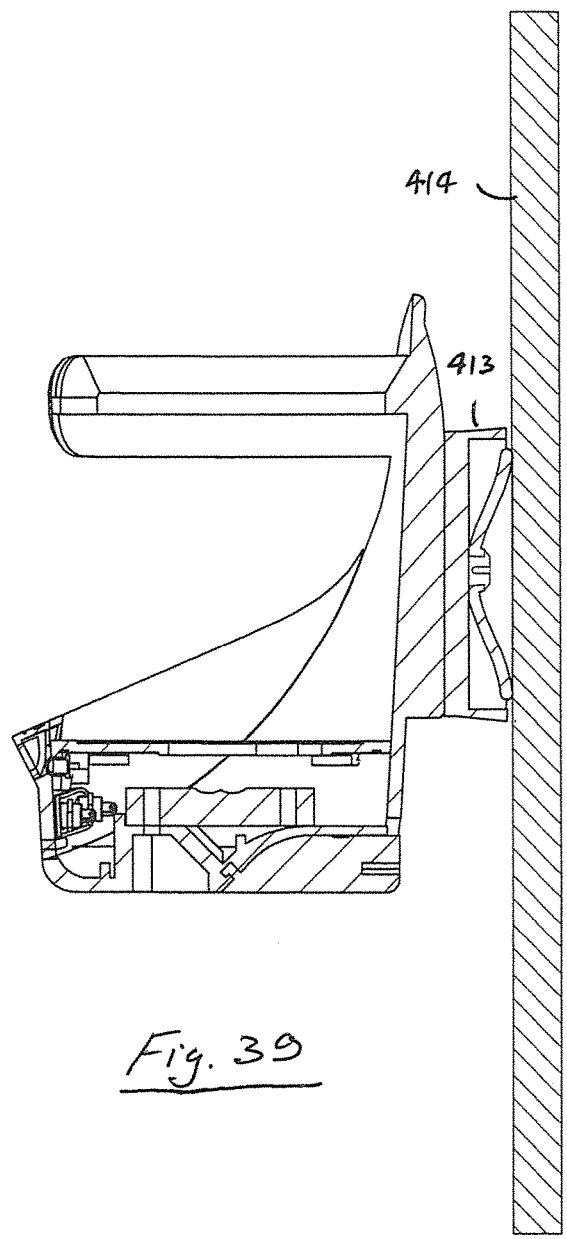

FIG. 38 is a front view and FIG. 39 is a cut section CC of FIG. 38 of the station and suction cup which attached to a flat vertical surface.

Figure 40:
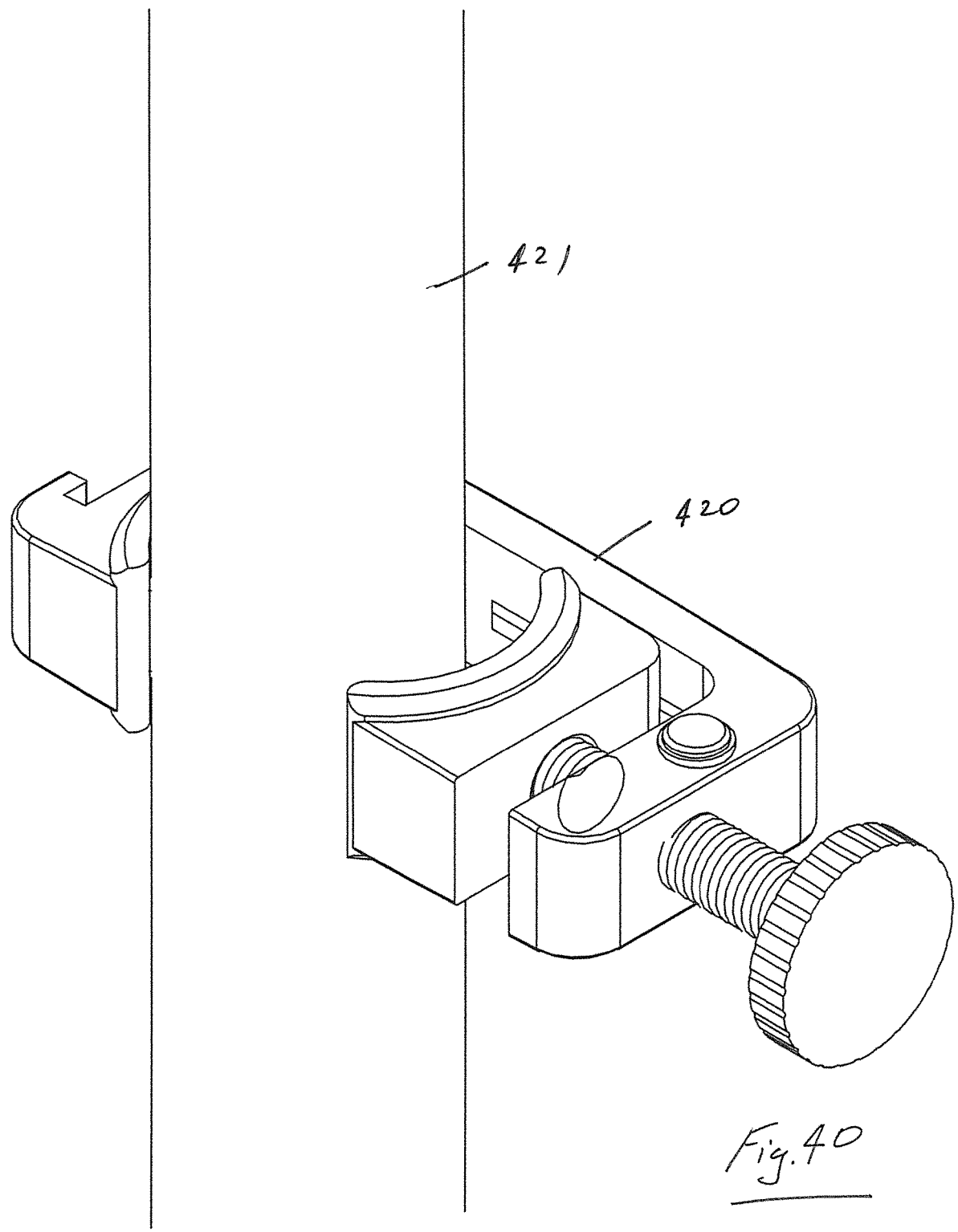
FIG. 40 is an isometric view of a mounting bracket for mounting the docking station of a support pole.

FIG. 40 is an isometric view of a mounting bracket 420 for mounting a docking station such as the docking station of FIG. 20 to a support pole 421. The bracket engages with the docking station, for example, by extending through the slot 255.

Figure 41A:
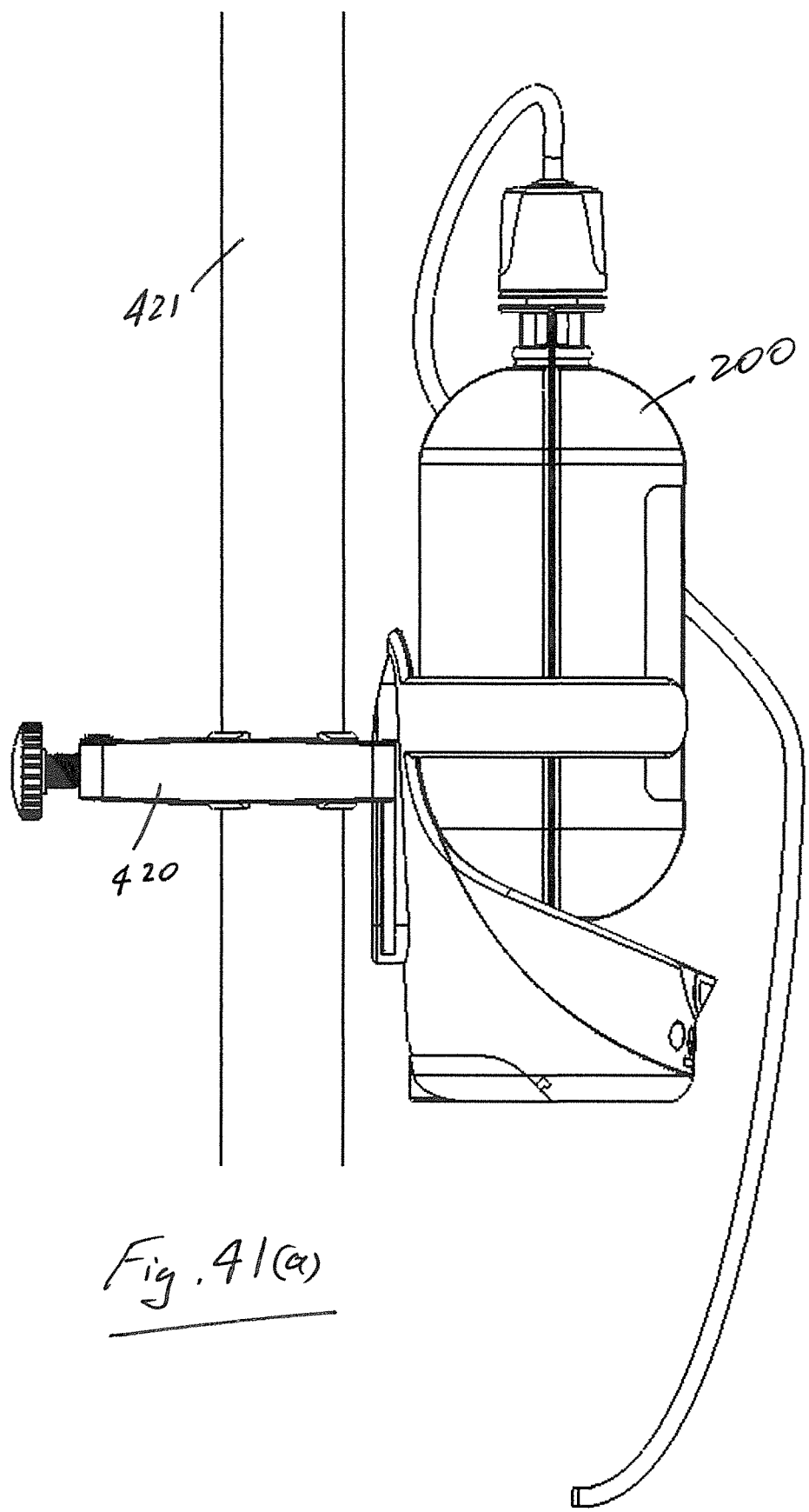
FIG. 41(a) is an image of a food pod mounting bracket and a docking station in side view.
Figure 41B:
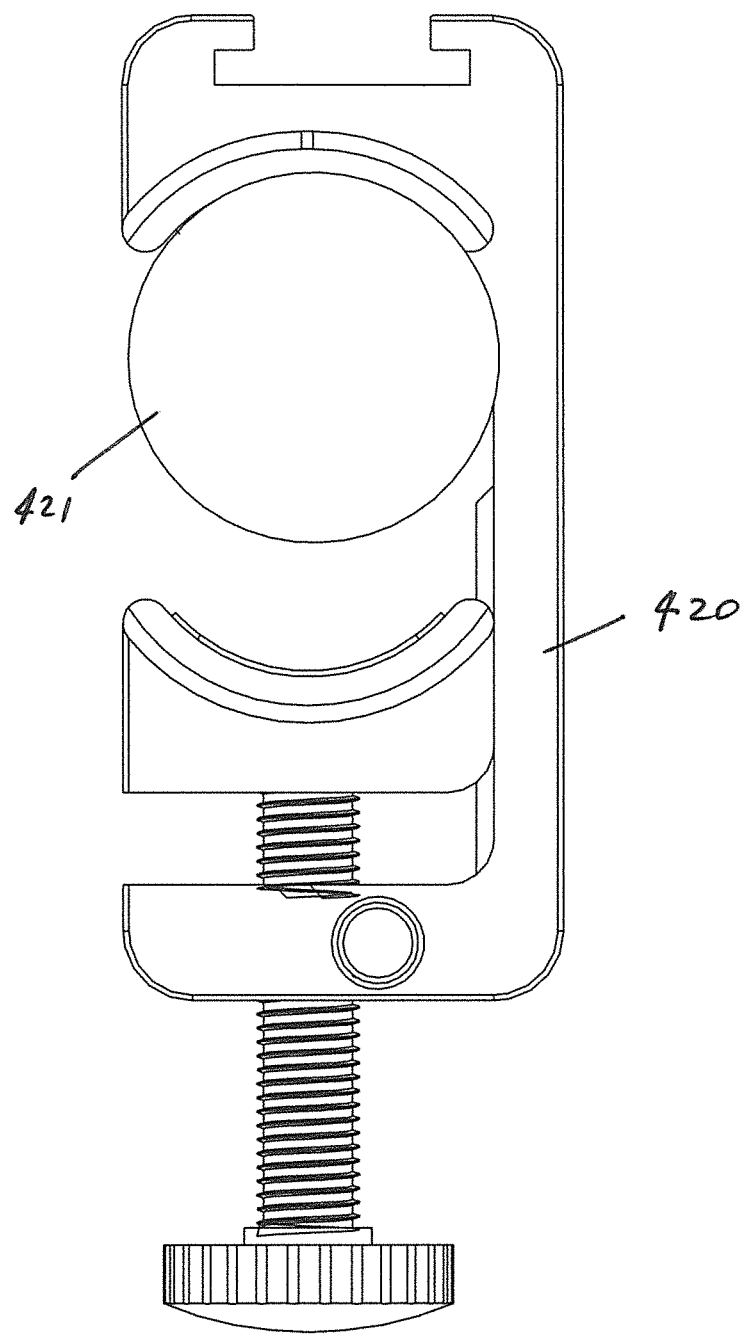
FIG. 41(b) is a top view showing the connection to a support pole.

FIG. 41(*a*) is an image of the food pod mounting bracket 420 and a docking station in side view.

FIG. 41(*b*) is a top view showing the connection to a support pole 421.

Figure 42:
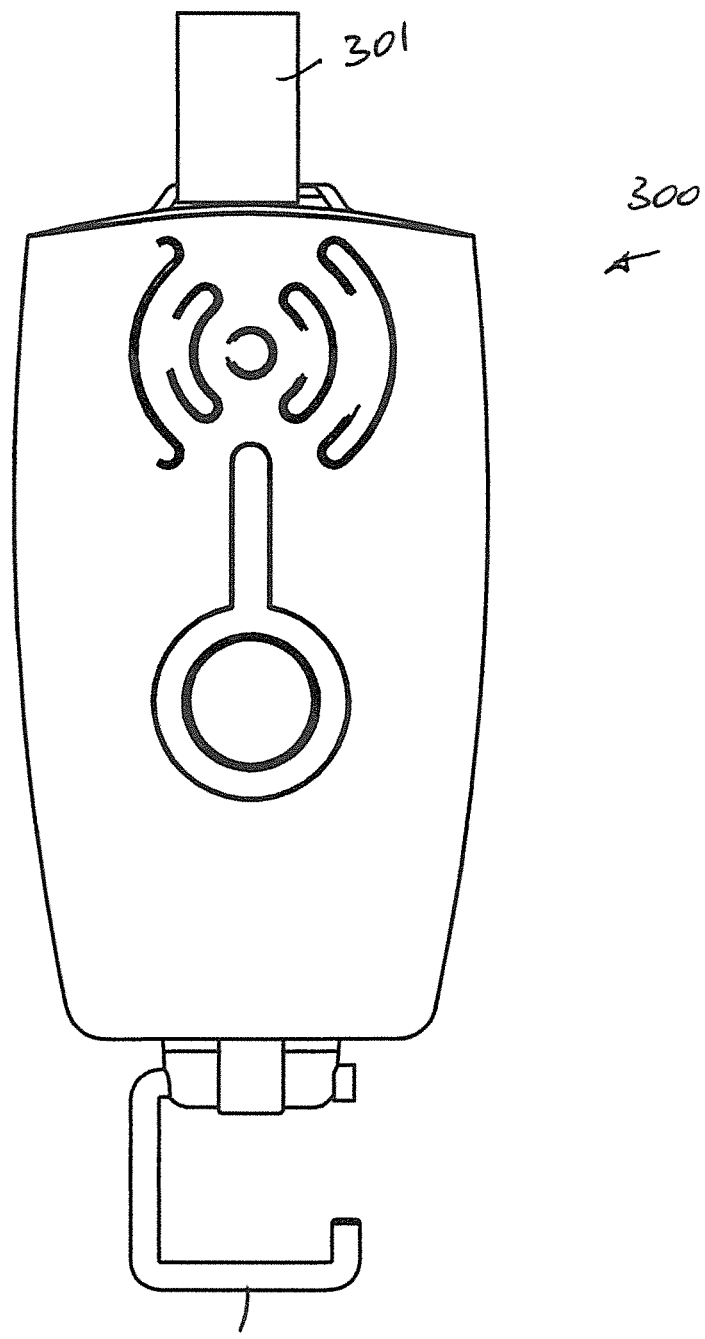
FIG. 42 is a front view of another docking station.

FIG. 42 is a front view of another docking station 300. In this case the docking station 300 has a strap 301 at an upper end for hanging on a support such as a bar 302 and a hook 303 at the opposite end on which a food pod 200 is suspended, for example, using an eyelet 305 on the pod 200.

Figure 43:
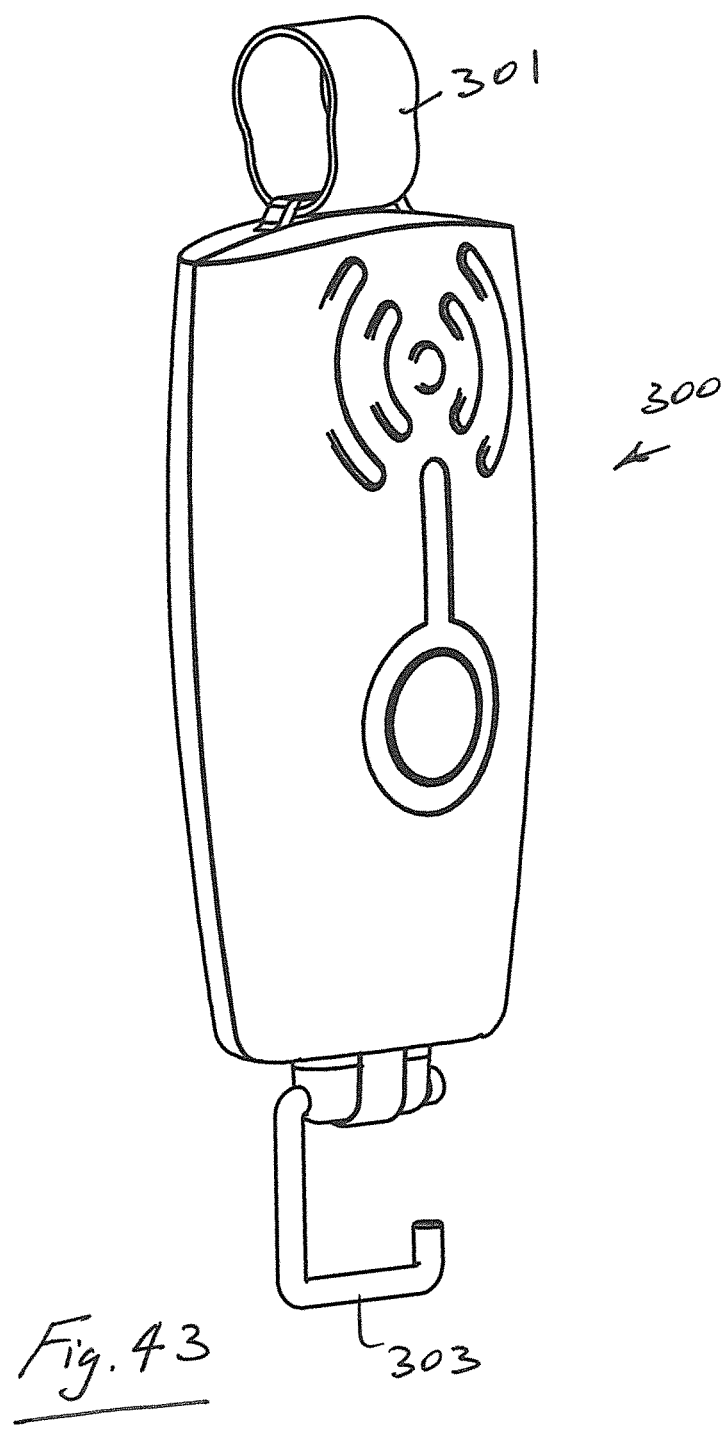
FIG. 43 is an isometric view of the docking station of FIG. 42.

FIG. 43 is an isometric view of the docking station 300 of FIG. 42.

Figure 44:
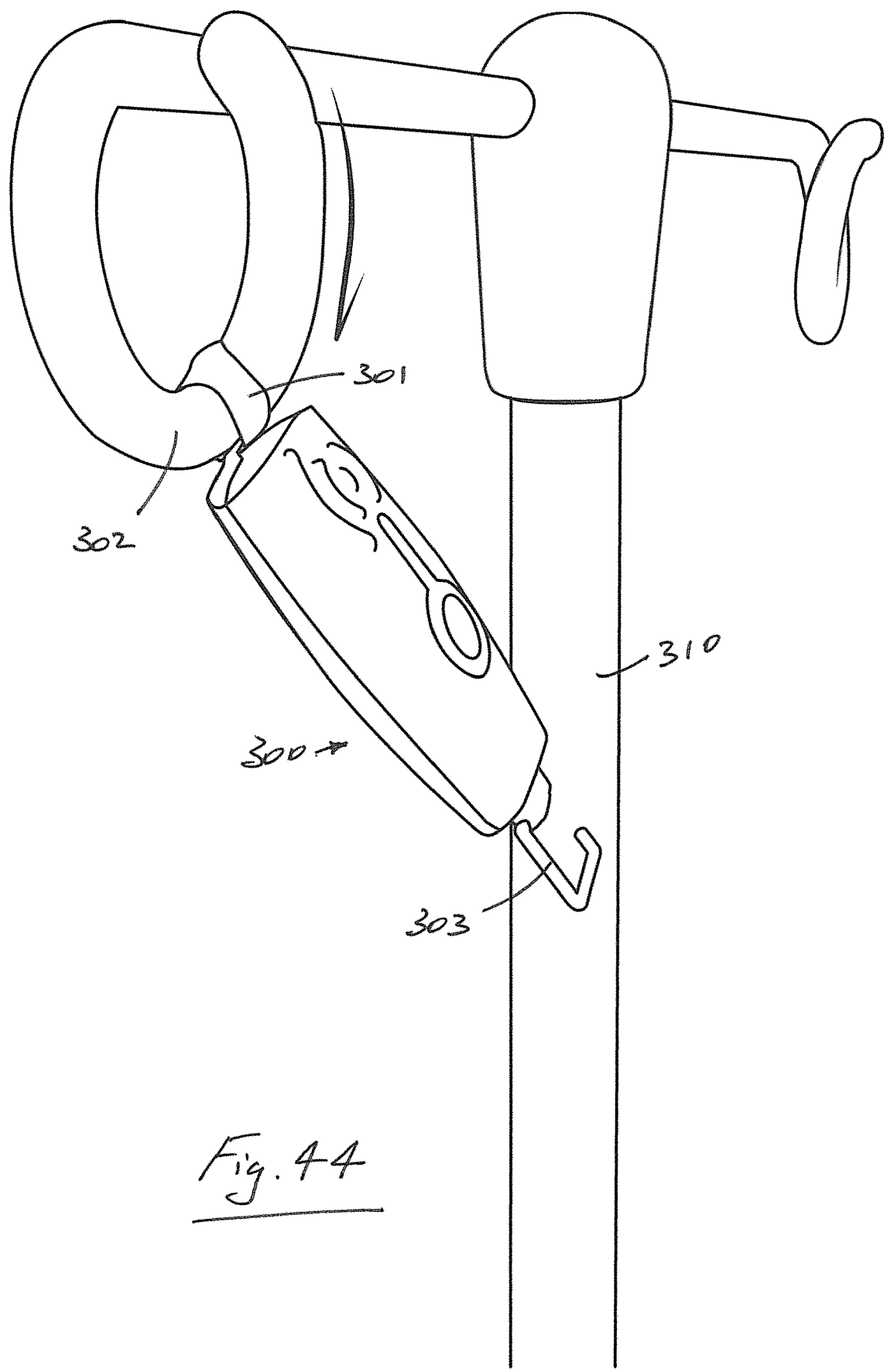
FIG. 44 is an image of the docking station being hung onto a support pole.

FIG. 44 is an image of the docking station being hung onto a support pole 310.

Figure 45:
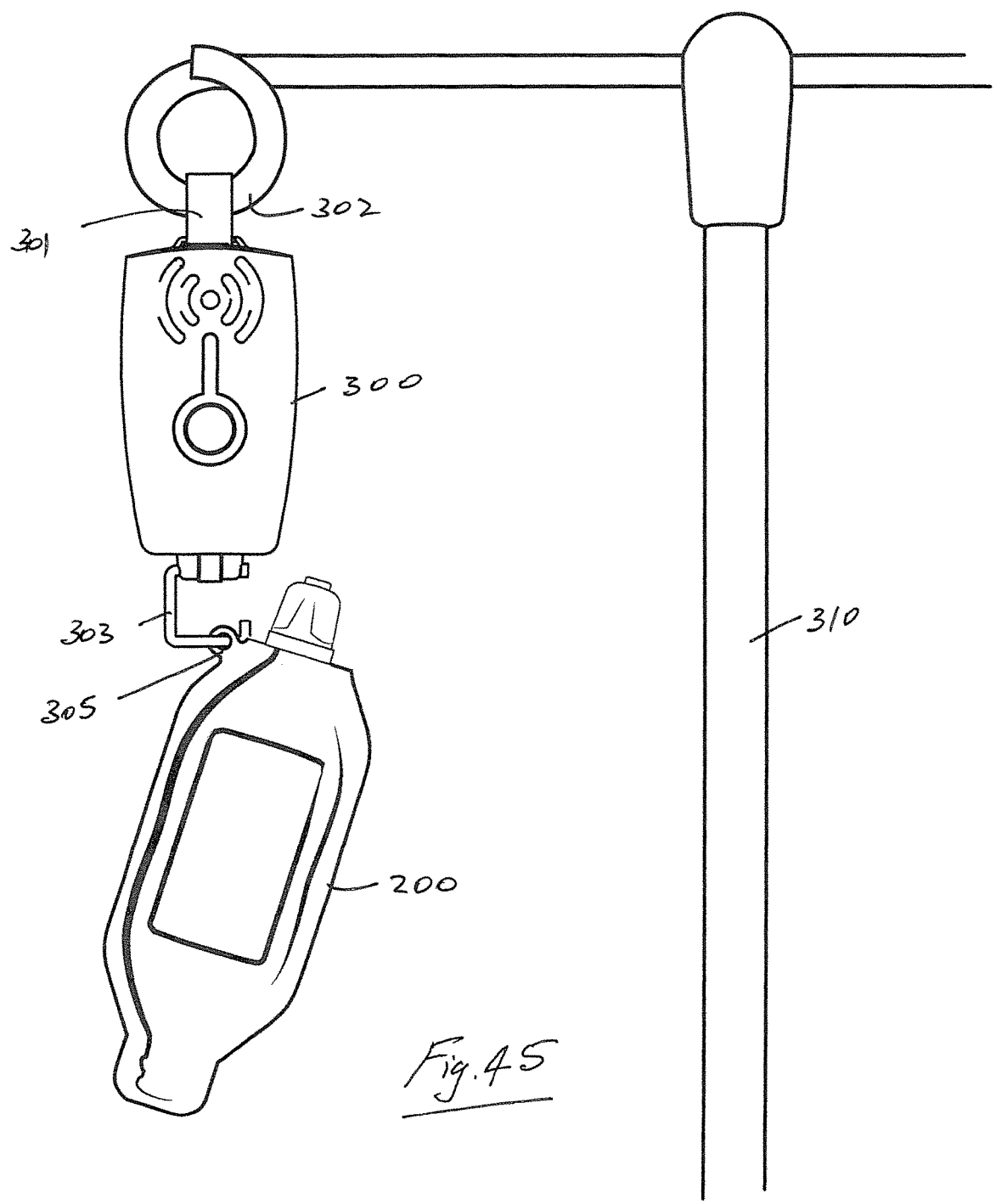
FIG. 45 shows the docking station of FIG. 44 connected to the support pole and a food pod hanging from the docking station.

FIG. 45 shows the docking station of FIG. 44 connected to the pole 310 and a food pod 200 hanging from the station.

Figure 46:
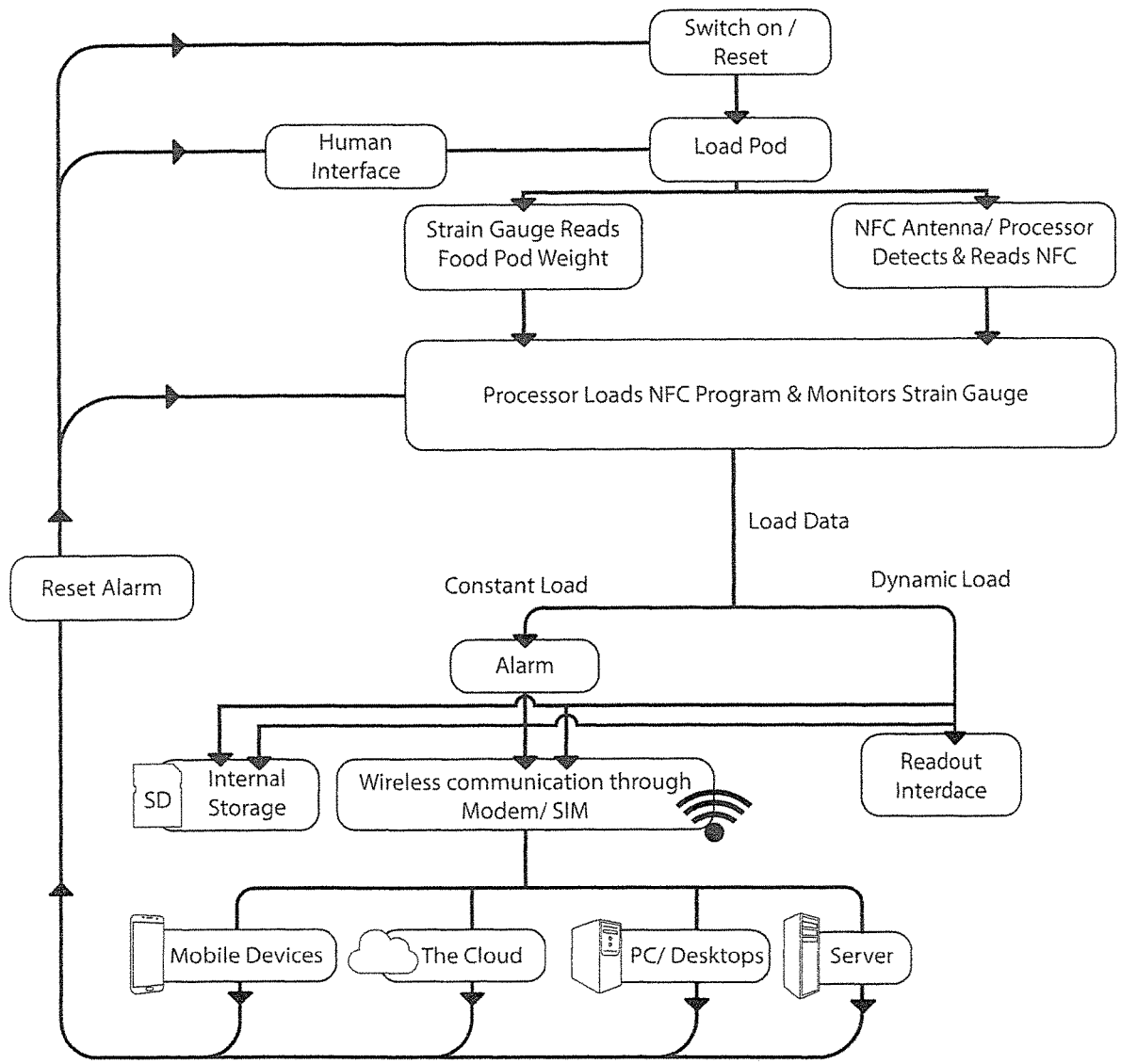
FIG. 46 is a flow chart of the operation of a docking station.

FIG. 46 is a flow chart of the operation of the docking station and illustrates the interaction between the processor, a strain gauge, an NFC tag, and optionally an application for a mobile device such as a telephone.

In use, the docking station is activated in the following sequence;

The delivery (giving) set is attached to the food pod which is primed for flow from the pod. The delivery set to the user. Switch the docking station "ON". Place the food pod into the docking station. The food pod has an electronic tag and the docking station has a tag reader which is activated to allow the docking station to identify the type of food pod loaded. Once the food pod is identified the docking station then automatically weighs the loaded food pod using the strain gauge to establish if it's new or partly used. The docking station processor then loads the correct food profile program to correspond with the food pod NFC identification. The giving set regulator is then adjusted to the correct settings. If the food pod empties either too slowly or too fast per the loaded food profile program, then the docking station will alarm. If the food pod weight remains static for a nominal period (say about 5 minutes) and the docking station can still read the food pod NFC tag, then the docking station will alarm as this is an indication that the food is not being delivered. There may be a fault such as a kink in the giving set. If the food pod empties naturally and approaches the food profile programs set endpoint, then the program can either alarm or indicate depending on the user's preferences.

Some or all of the docking station data, alarms, user input, etc. can be stored locally in the docking station on a SD card, etc. or in the cloud, server, PC or mobile device. Data can be transferred via WiFi/Modem and SIM. Remote control of the docking station can be achieved by a docking station software application loaded onto a mobile phone/laptop/PC or tablet. The application allows as much or greater functionality as the docking station control buttons. Alarms can be cleared, data reviewed, programs altered, etc. If the food pod is removed from the docking station, for example for a bathroom break, the docking station will go into sleep mode for a defined period such as 15 mins. If the same food pod is replaced in the docking station during this period then the docking station will recognize the last food pod NFC tag identification, update the food profile program data and finish time. If the food pod is not replaced in the docking station during this defined period, then the docking station will alarm.

Figure 47:
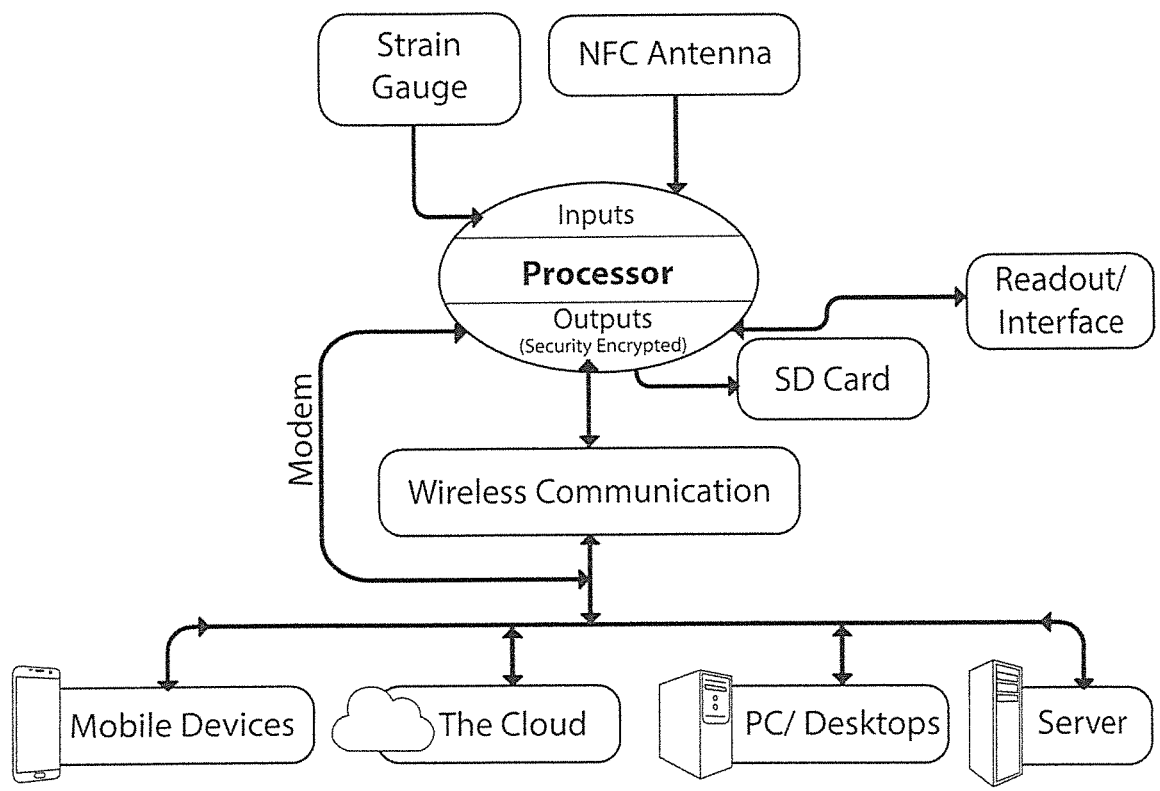
FIG. 47 is a flow chart illustrating the processing of the inputs by the processor to provide outputs.

FIG. 47 is a flow chart illustrating the processing of the inputs by the processor to provide outputs.

Figure 48:
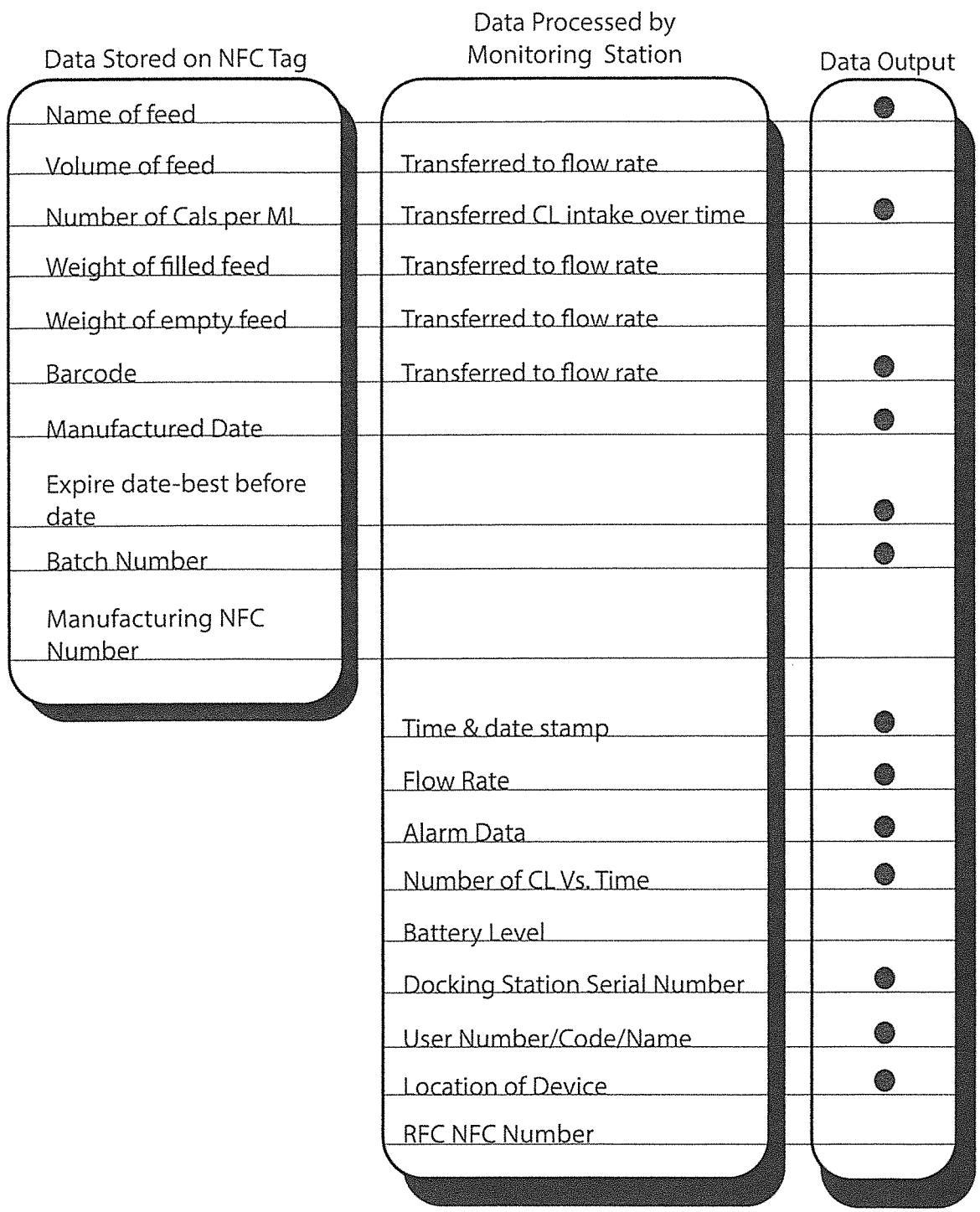
FIG. 48 is a chart listing data carried.

FIG. 48 is a chart listing data carried. The column on the left lists data carried by the NFC tag.

The column in the middle lists data that is processed. If blank, there is no change from the data fed from the NFC. The column on the right lists data that is sent wirelessly to the cloud, mobile devices or the like.

Referring to FIGS. 49 to 83 of the drawings, there is illustrated an enteral feeding apparatus 1 in the form of a pod which may be pre-loaded or self filled with enteral fluid. The apparatus comprises an expansile pouch 2 which defines a reservoir for enteral fluid and a barrier 3 which surrounds the pouch 2. The apparatus comprises an inlet port 5 for delivery of enteral fluid into the pouch 2 and an outlet port 6 for delivery of enteral fluid from the pouch 2. The outlet port 6 includes a seal such as a foil 7 which is pierceable to release enteral fluid from the pouch 2. A removable cap 9 closes the outlet port 6.

The pouch 2 is expansile from a collapsed empty configuration to an expanded filled configuration. The expansile pouch 2, when filled, provides the force by which enteral fluid is delivered from the pouch through the outlet port 6. As enteral fluid is delivered from the pouch it starts to collapse. The barrier 3 is substantially impermeable to gas and protects the contents of the expansile pouch from spoilage in storage caused by air passing through the wall of the expansile pouch. The barrier 3 is also partially collapsible, however, in one case the barrier collapses to a larger volume than that of the pouch as it collapses. In this way, a space is defined between the pouch and the barrier into which gas (such as Nitrogen used in filling) from the pouch passes and is retained by the barrier. The barrier may comprise a membrane which is substantially gas impermeable. For example, the barrier may comprise a foil, especially a metallic foil such as an aluminium foil.

The outlet 6 from the feeding pod is connected to a feedings tube 10 which has a Leur or ENFit connector 11 for connection to an inlet 12 to a PEG (percutaneous endoscopic gastronomy) fixture. ENFit connectors are described, for example, at http://stayconnected.org/applications/enteral/.

A regulator 15 is provided on the feeding line. The regulator 15 is adjustable between at least three different positions corresponding to an off position, a fully on position, and at least one intermediate position.

As the reservoir is being filled with the enteral fluid through the inlet port 5, the elastomeric material of the pouch 2 expands. When the reservoir is filled, a cap or seal 20 is placed on the inlet. A gas escape route may be provided.

Figure 49:
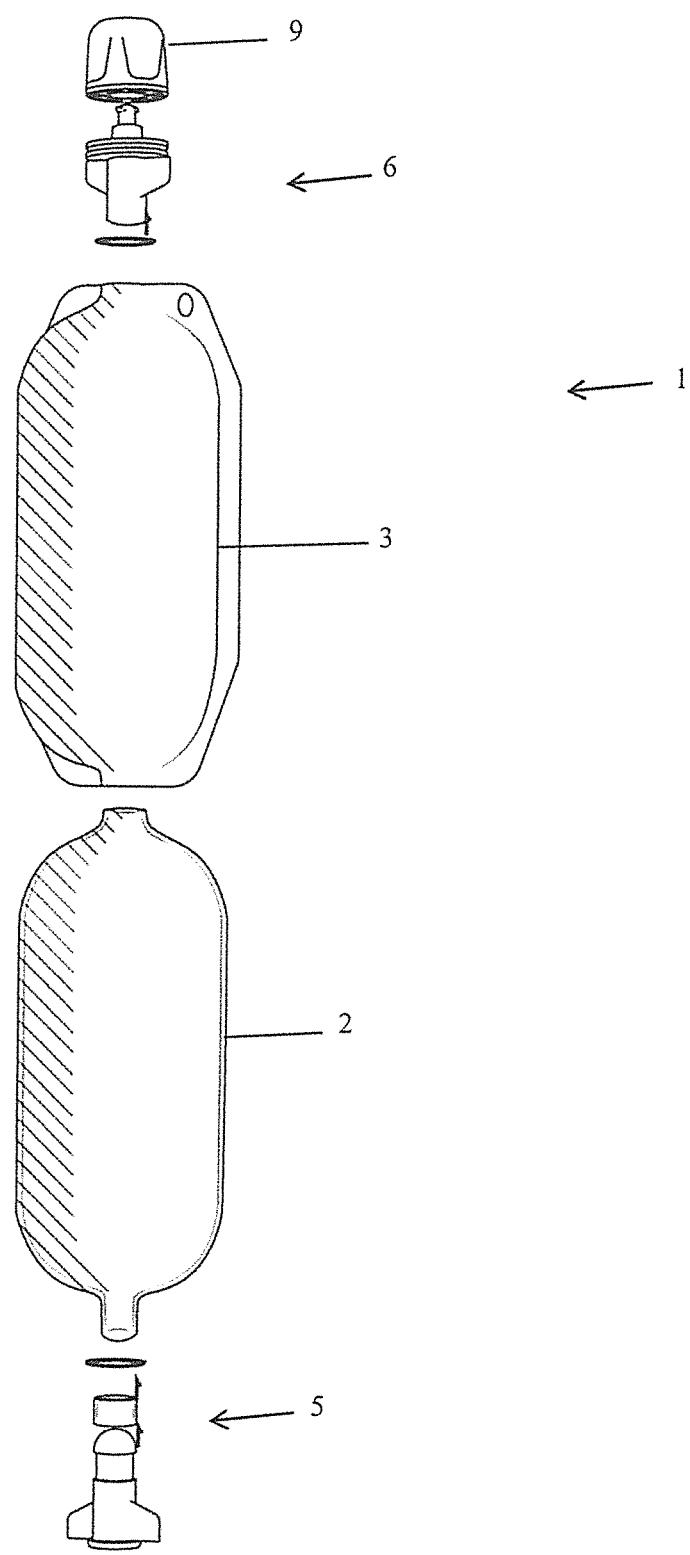
FIG. 49 is an isometric exploded view of an enteral feeding apparatus according to the invention.
Figure 50:
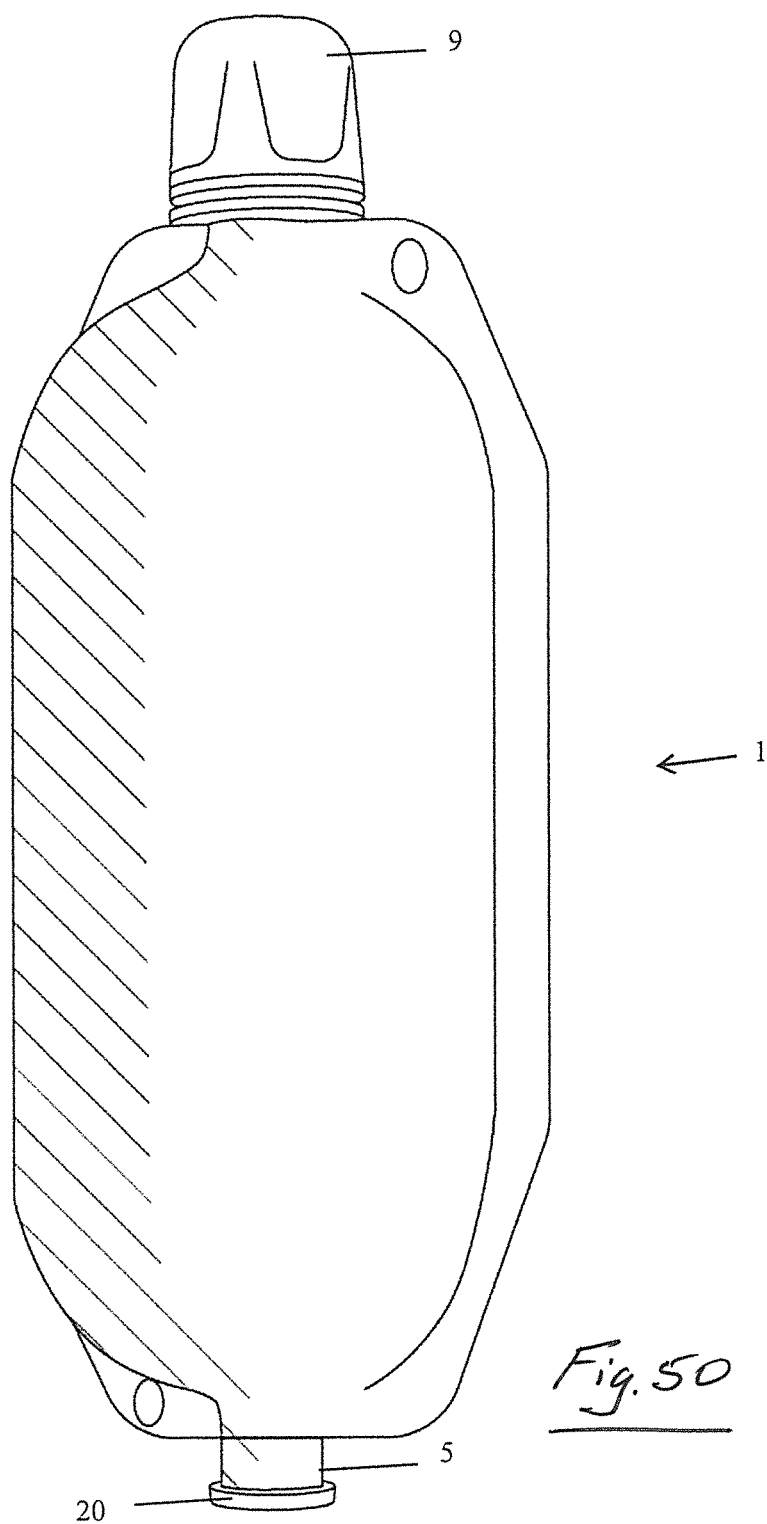
FIG. 50 is a view of the assembled apparatus of FIG. 49.
Figure 51:
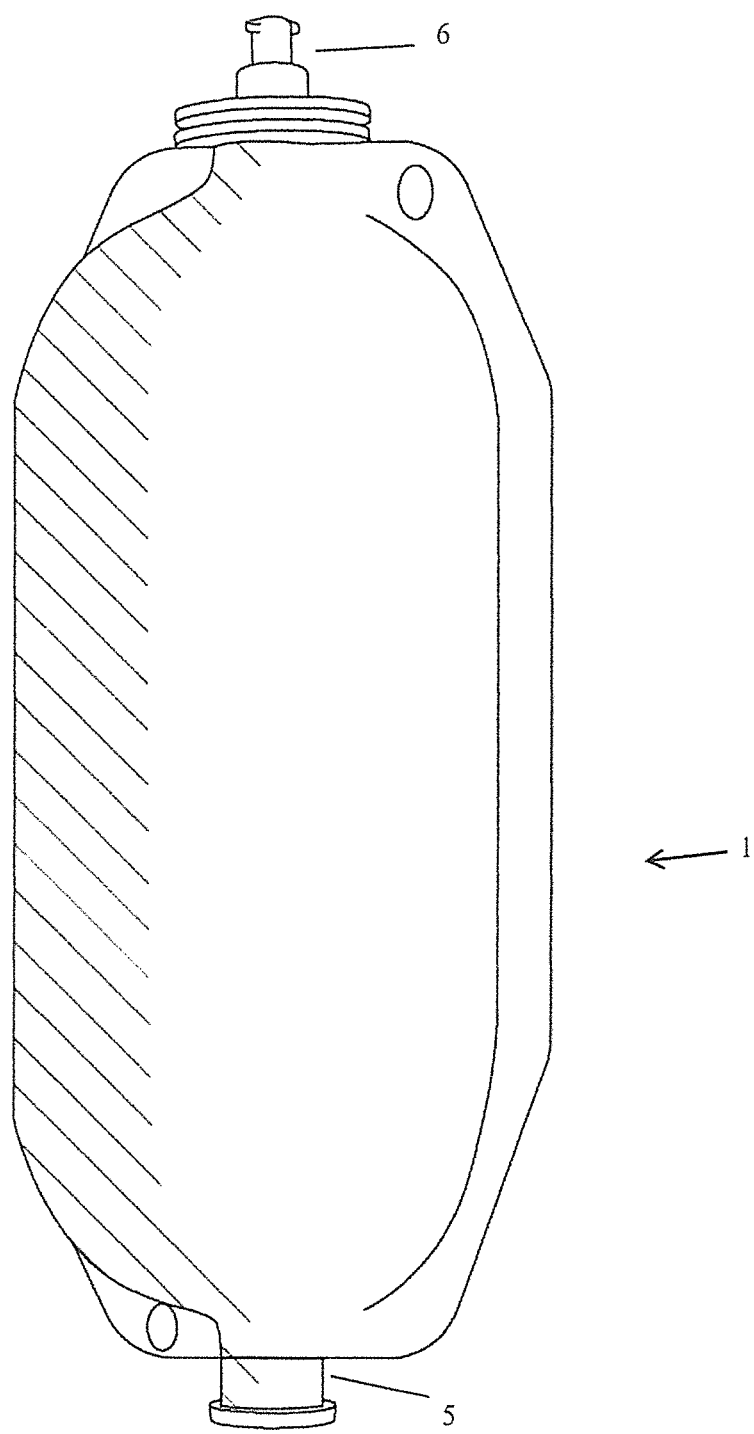
FIG. 51 is another view of the apparatus of FIG. 49 with a cap for the delivery port removed.
Figure 52:
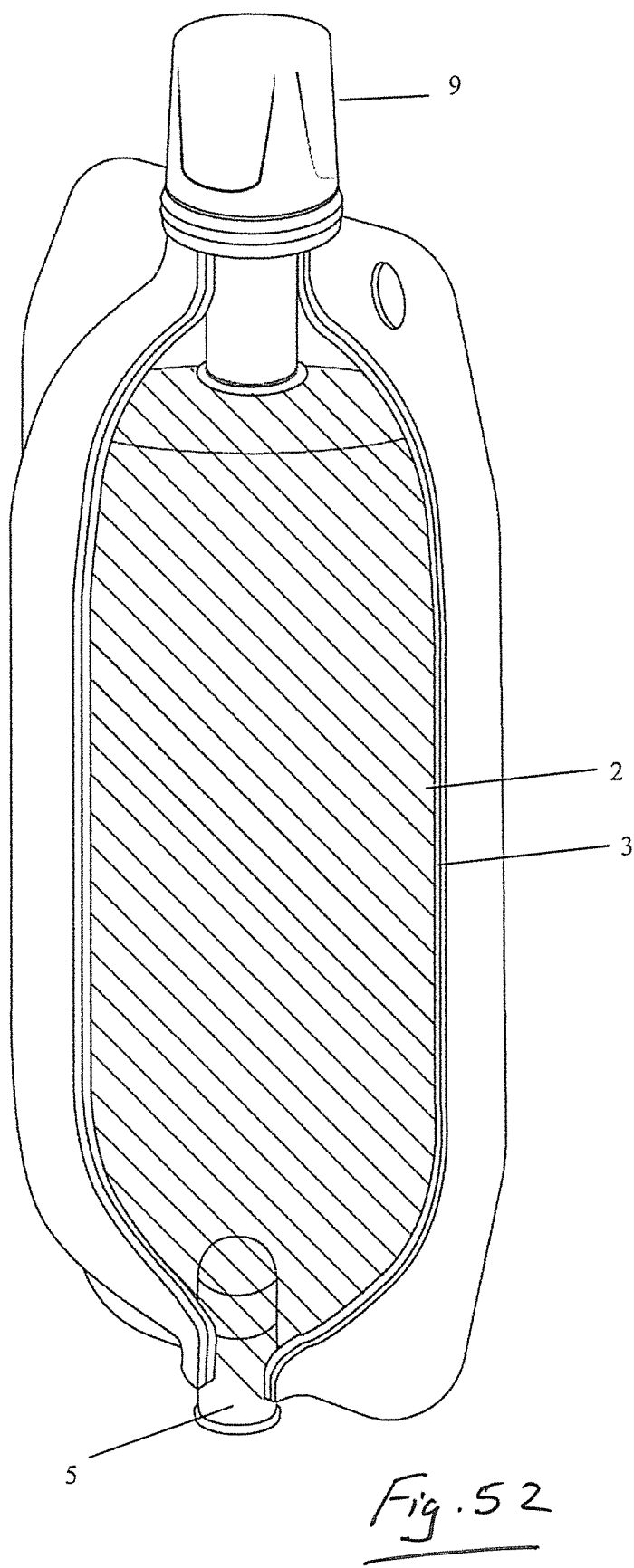
FIG. 52 is a partially cut-away view of the apparatus.
Figure 53:
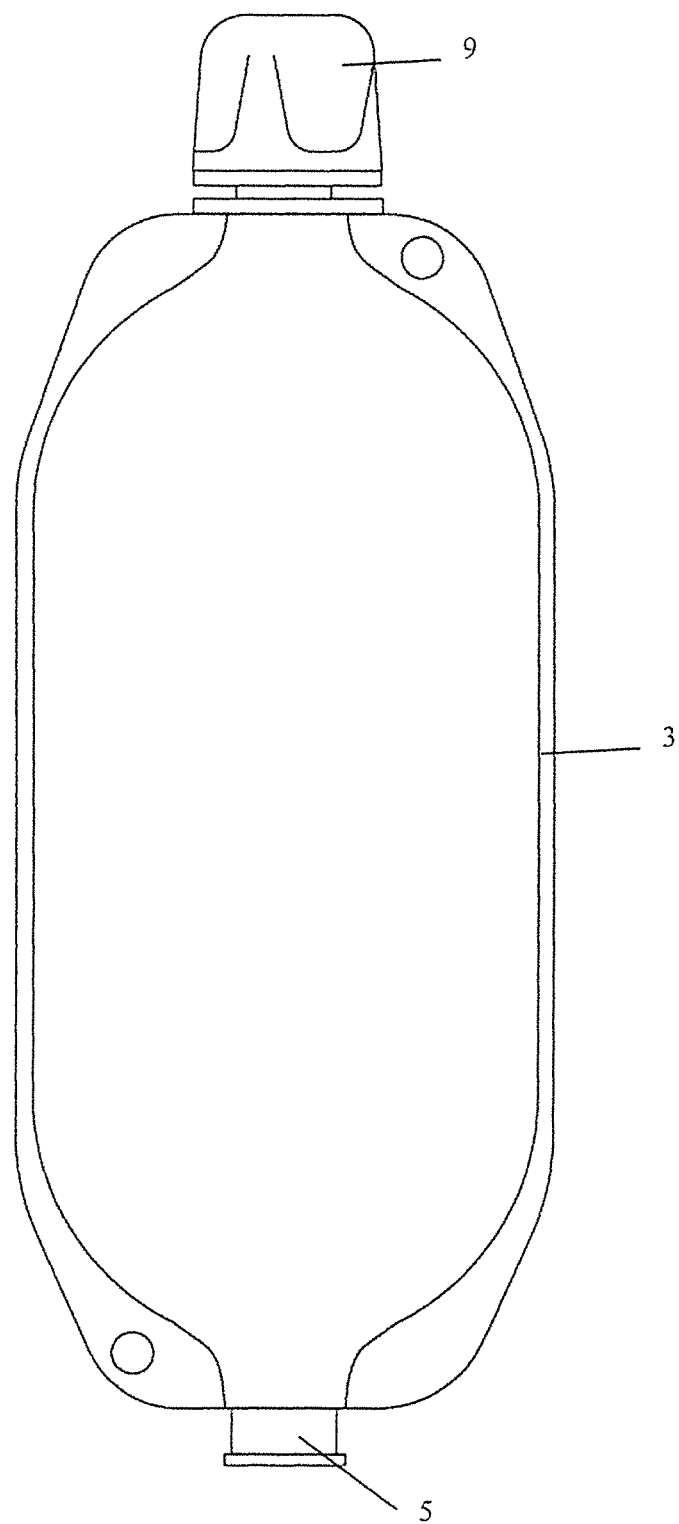
FIG. 53 is a view of an outer barrier of the apparatus.

FIG. 49 is an exploded view which illustrates the inner pouch 2, external barrier 3, inlet port 5 and outlet port 6 including the removable cap 9.

FIGS. 50 to 53 illustrate the assembled apparatus.

Figures 54A, 54B, 54C:
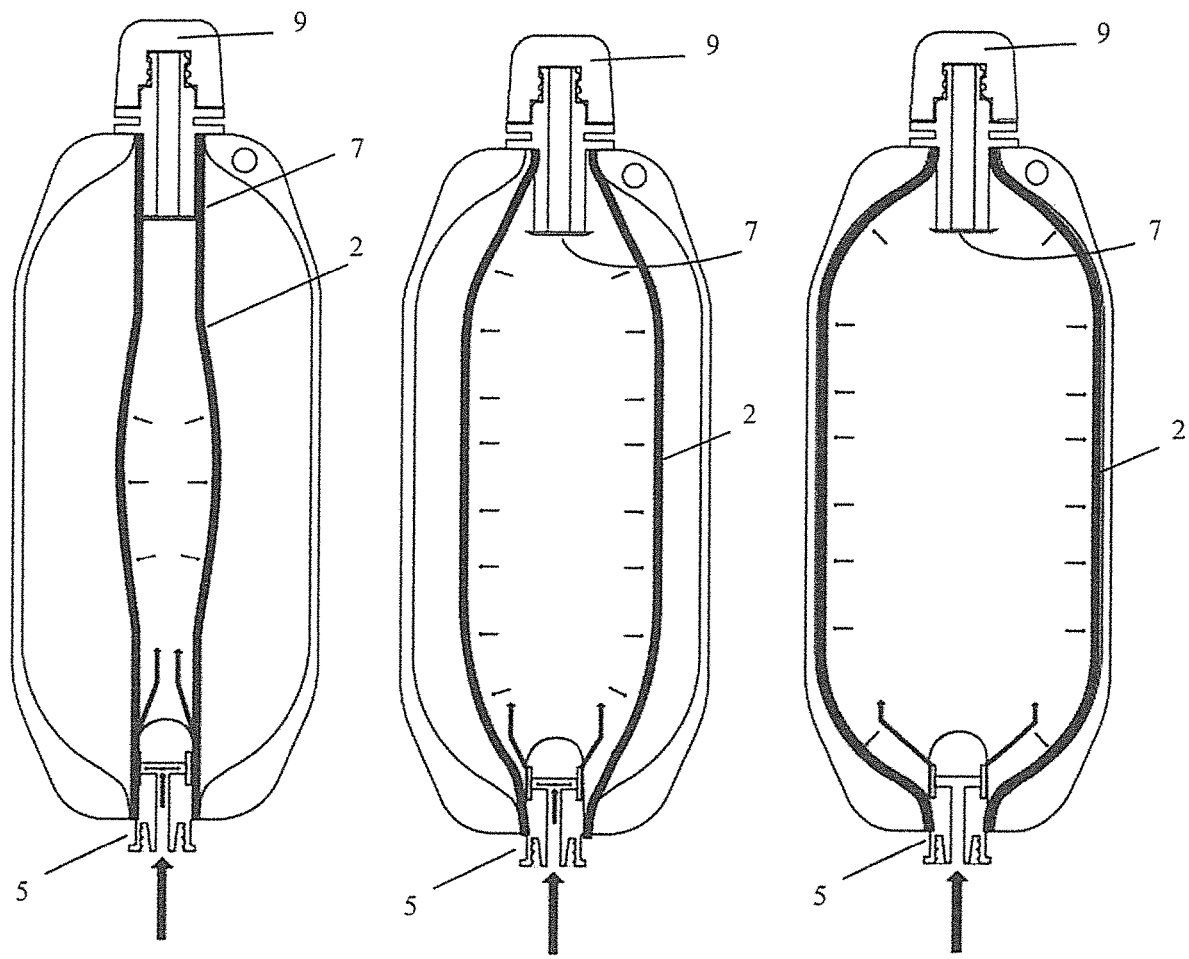
FIGS. 54(*a*) to 54(*c*) illustrate the filling of the pouch.

FIGS. 54(*a*) to 54(*c*) illustrate the filling of the pouch through the inlet port 5.

Figure 55:
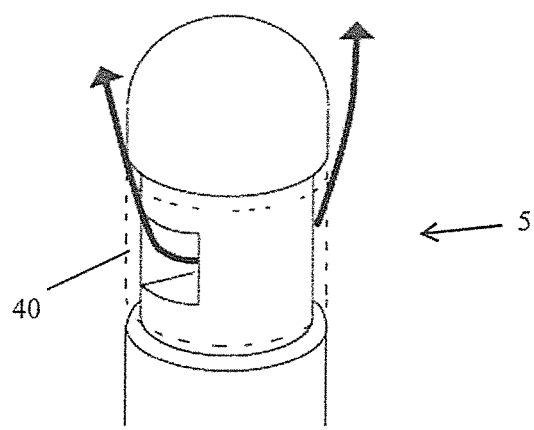
FIG. 55 is an enlarged view of a valve at the inlet port.
Figure 56:
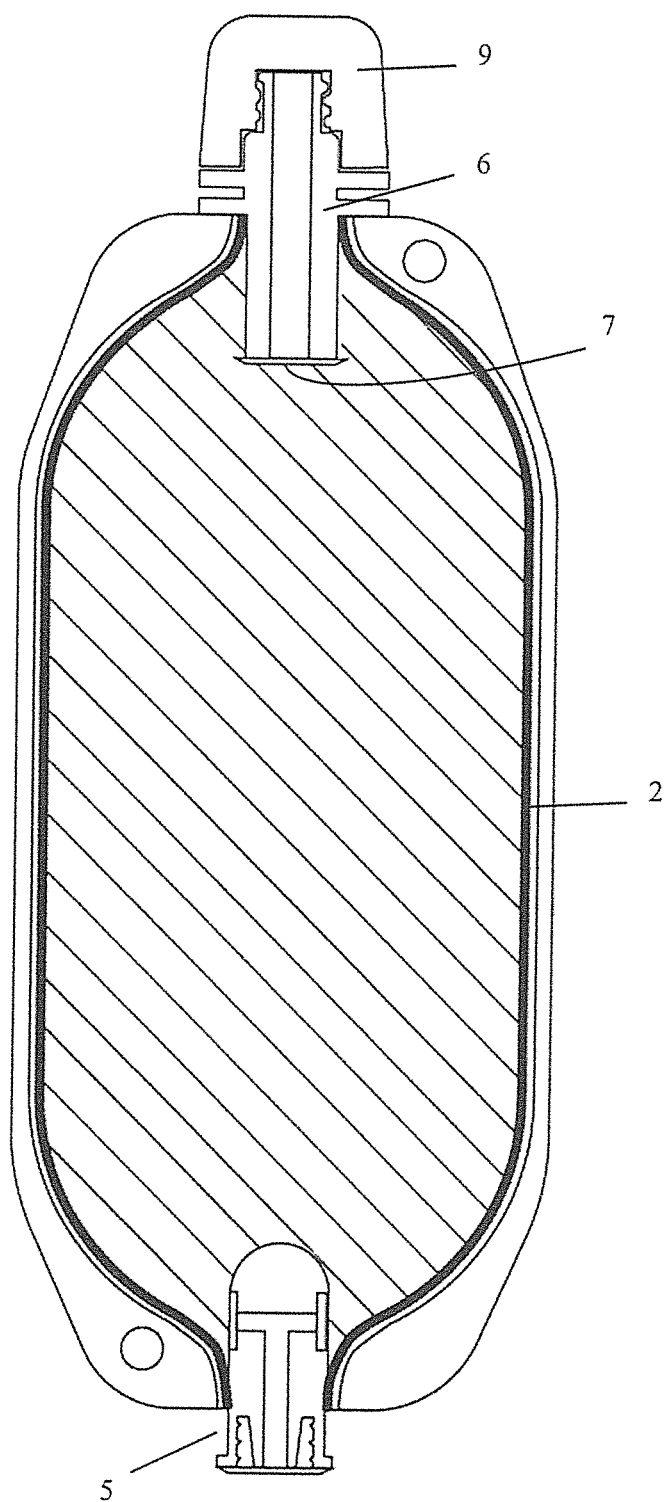
FIG. 56 is a cross sectional view of a filled pouch surrounded by a barrier.
Figure 57:
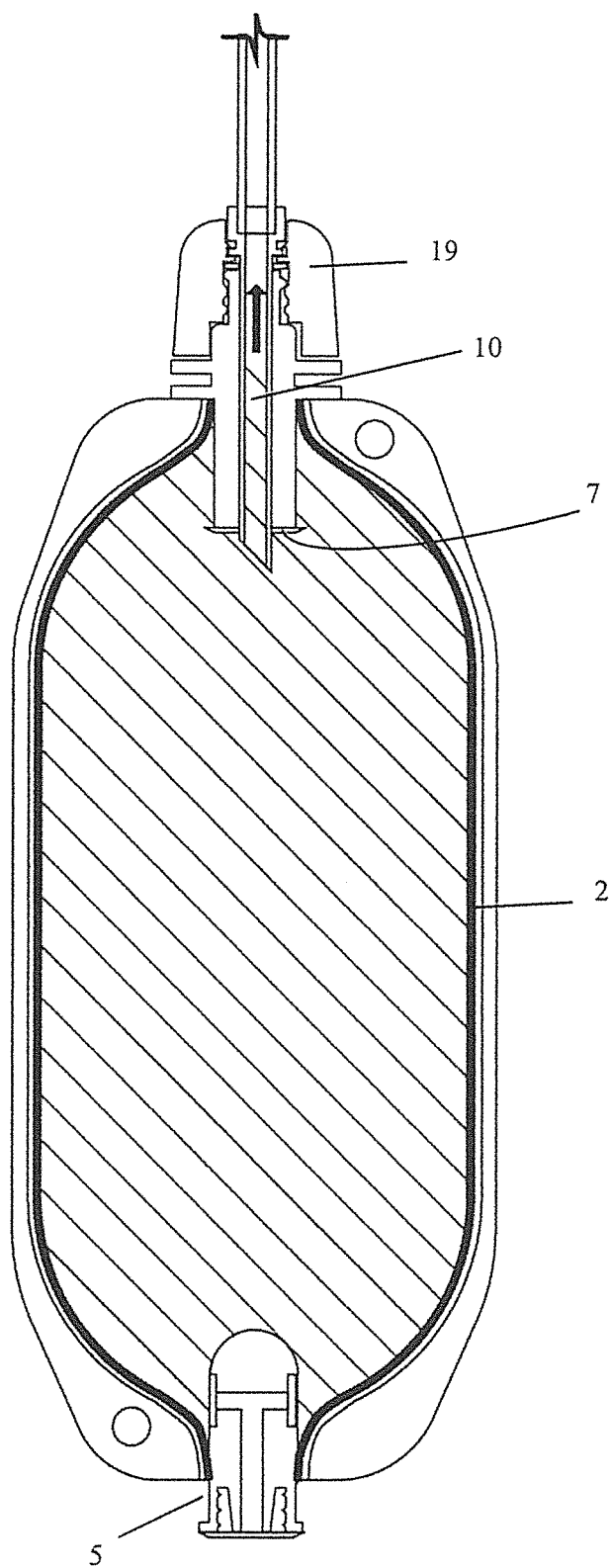
FIG. 57 is a cross sectional view illustrating the puncturing of a seal of the delivery port.
Figure 58:
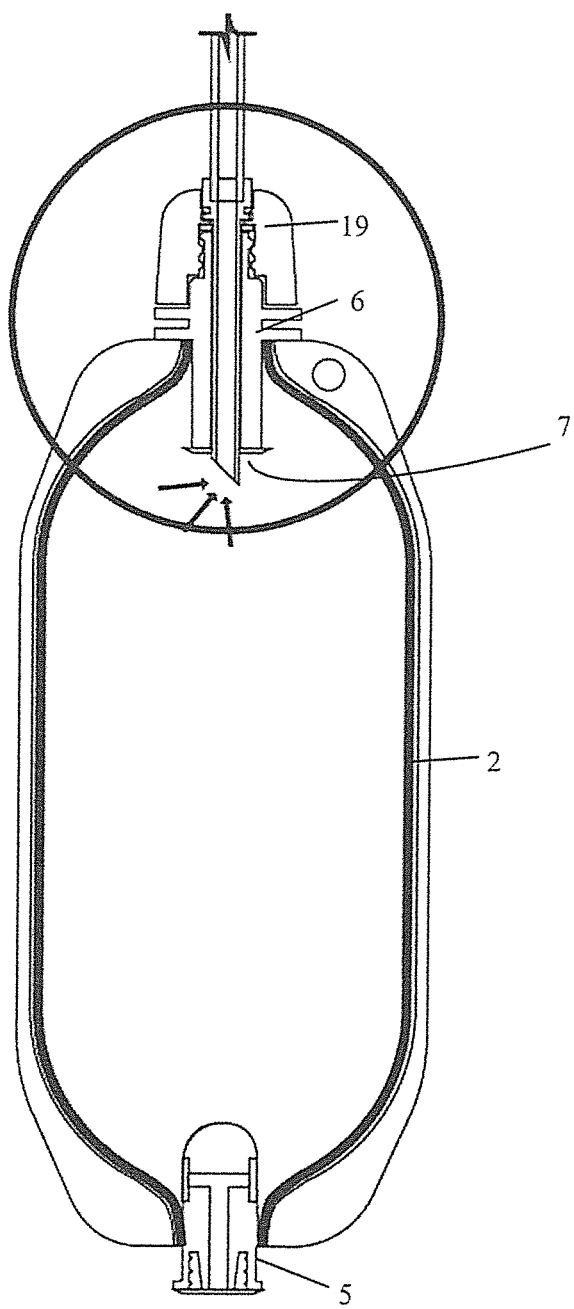
FIGS. 58 and 59(*a*) to 59(*c*) are views illustrating puncturing of the seal.

FIG. 55 shows a non-return valve/seal 40 at the inlet port 5.

Figure 59A:
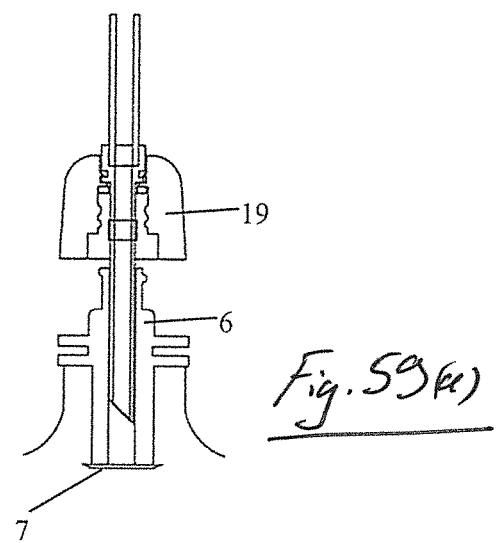
Figure 59B:
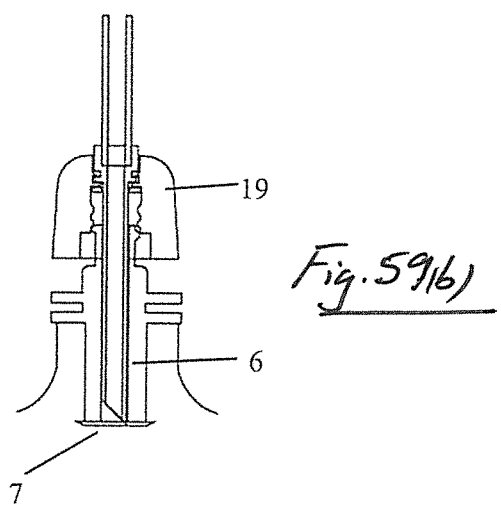
Figure 59C:
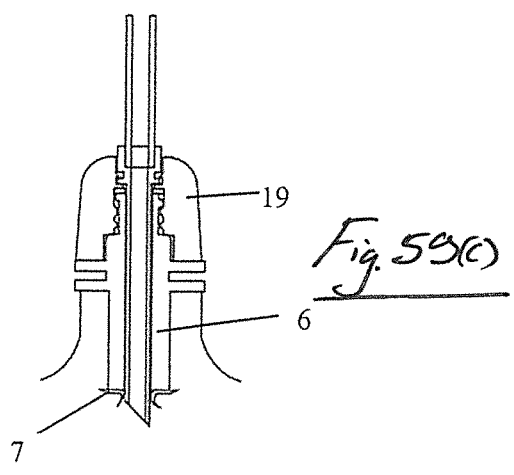

FIGS. 56 to 59 illustrate various steps in inserting a feeding tube through the seal of the outlet port. The point of the piercing cap 19 is engineered to pierce the seal 7 on its last half revolution when the threads are intact as best seen in FIG. 59(*c*). The cap may include a compression seal/washer.

Figure 60A:
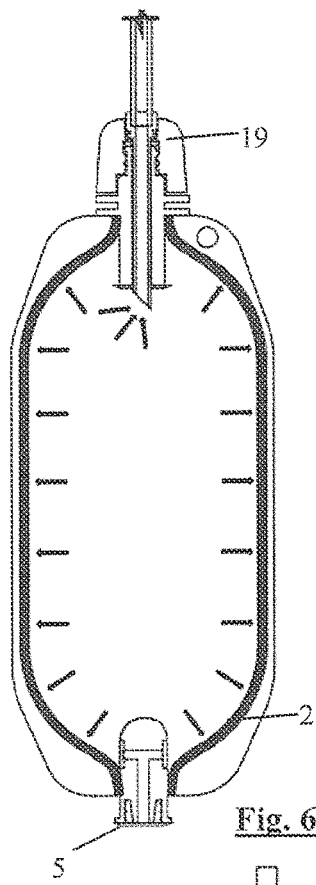
FIGS. 60(*a*) to 62(*b*) illustrate the collapsing of the pouch, in use.
Figure 61A:
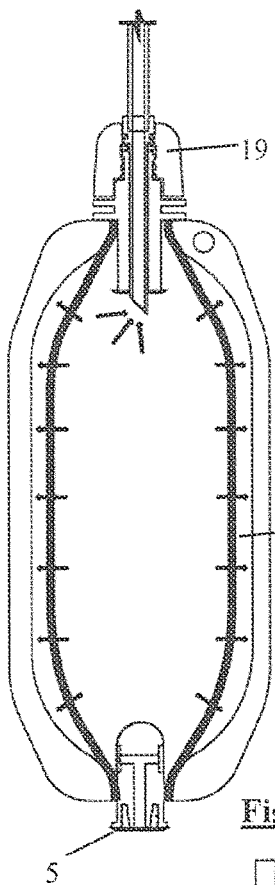
Figure 62A:
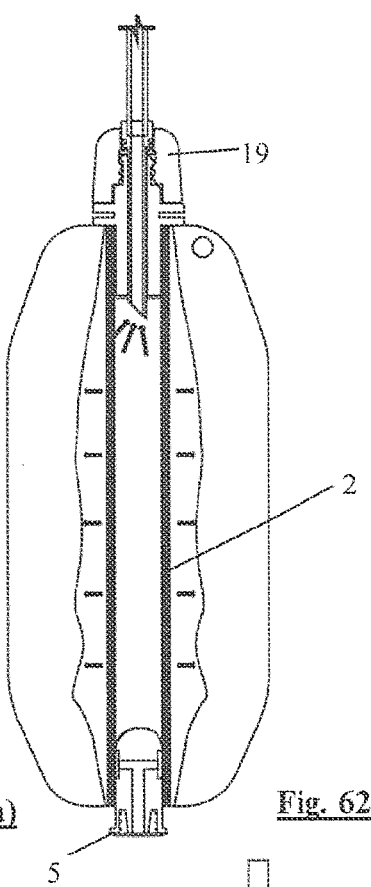
Figure 60B:
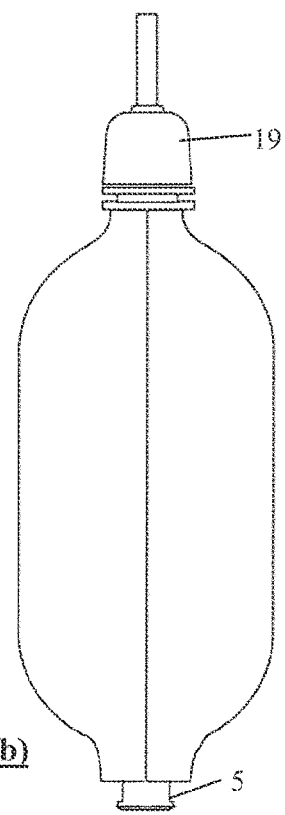
Figure 61B:
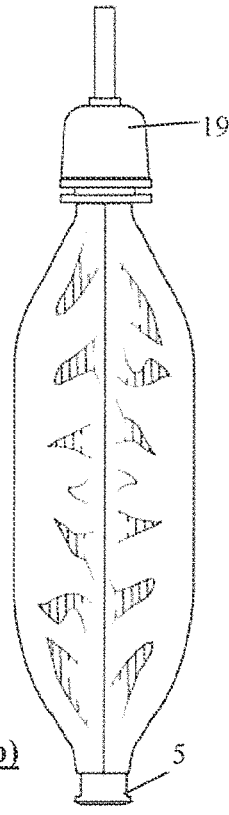
Figure 62B:
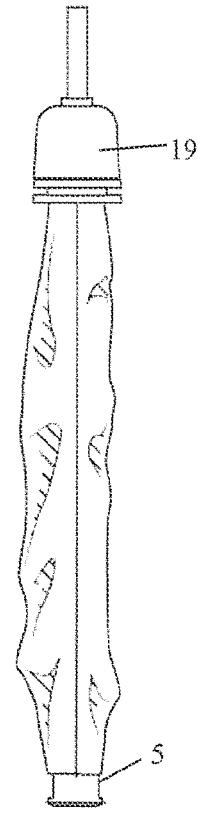

FIGS. 60(*a*) to 62(*b*) illustrate the gradual collapse of the pouch 2 as enteral fluid passes out through the outlet port caused by the expansile force of the pouch. It will be noted that as the pouch 2 collapses, the barrier 3 also collapses but to a much lesser degree than the collapse of the pouch. In this way a space is defined between the outer wall of the collapsing pouch and the inner wall of the partially collapsing barrier.

Figure 63:
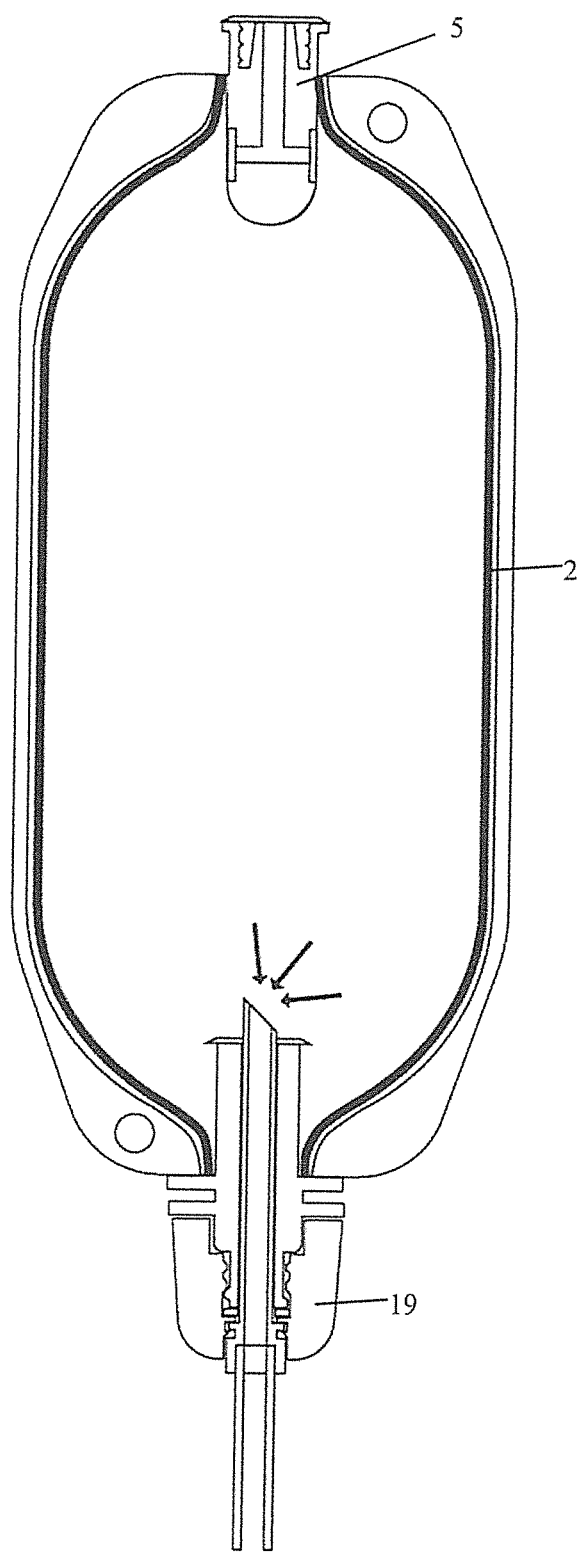
FIG. 63 illustrates the apparatus in a delivery configuration in another orientation.

Enteral fluid is delivered from the pouch by the expansile force of the pouch regardless of the orientation of the pouch. A different orientation of the pouch is illustrated in FIG. 63 by way of example.

Figures 64, 65:
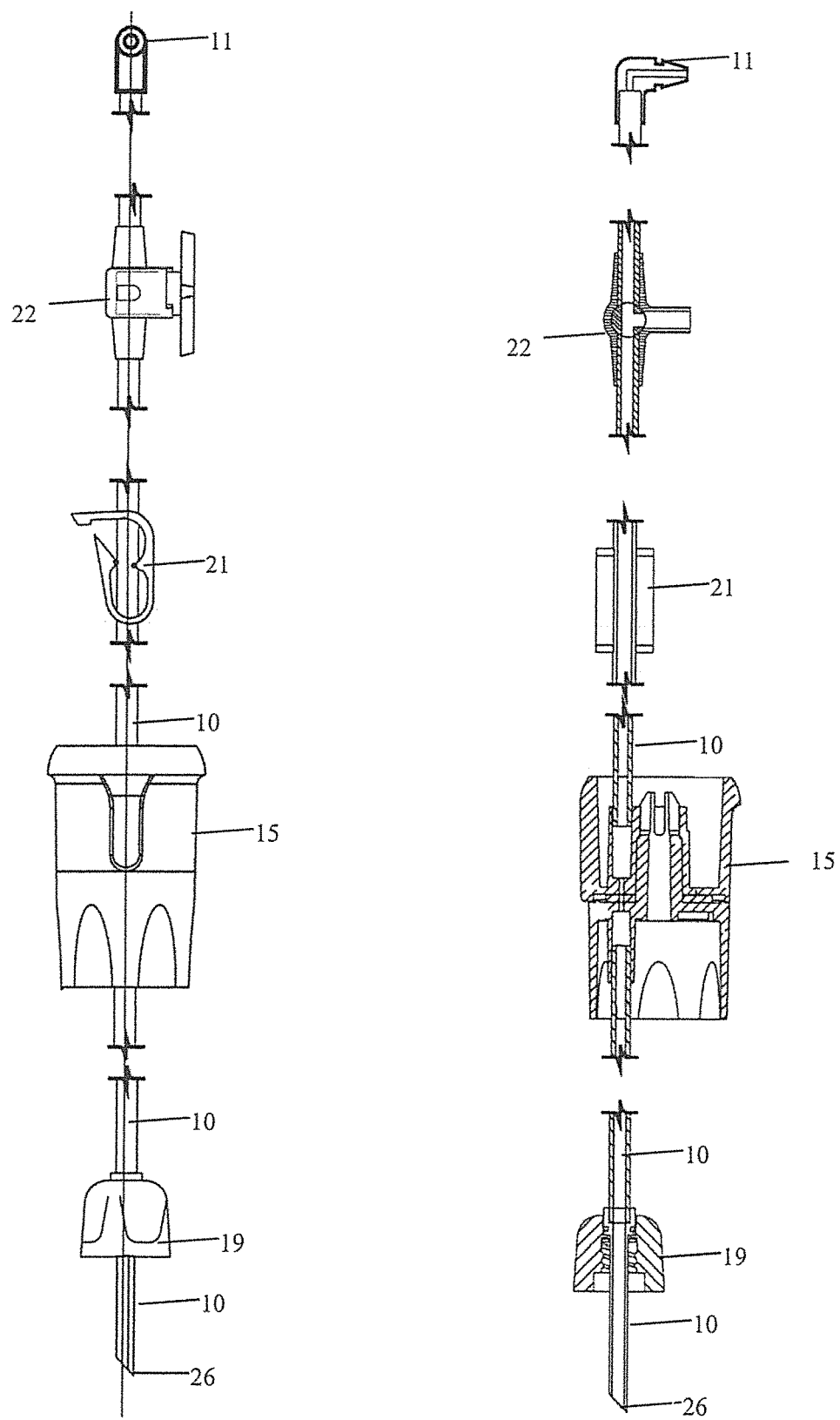
FIGS. 64 and 65 are exploded views illustrating the connection of the apparatus to a PEG feeding set.
Figure 66:
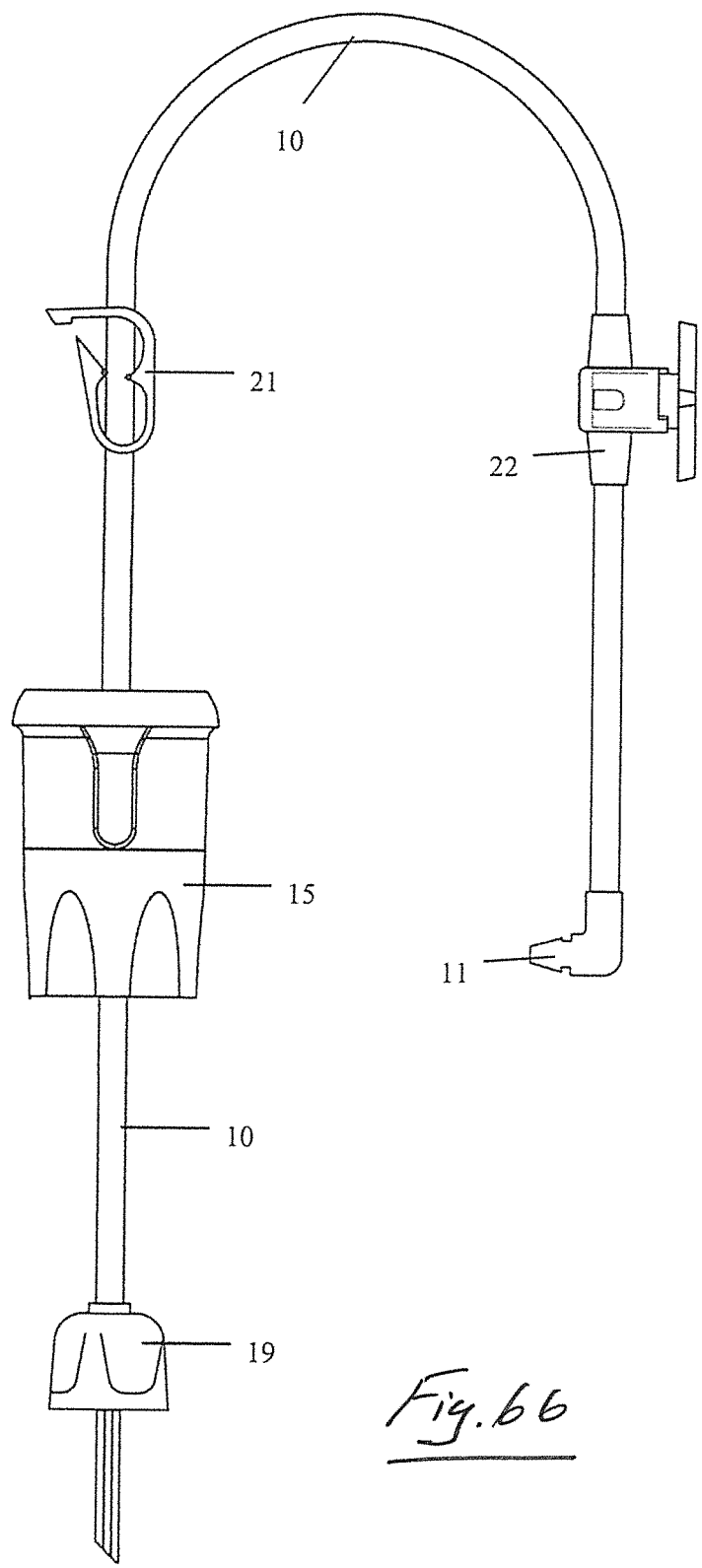
FIG. 66 is a view of the feeding set of FIGS. 64 and 65 assembled.

An enteral feeding set for use with the pouch of the invention is illustrated in FIGS. 64 to 66. The feeding set comprises a tube 10 having a connector 11 at one end for connection to a PEG inlet 12. The tube 10 extends through a cap 19 at the opposite end and terminates in a pointed end 26 which is used to pierce the seal 7 at the pod inlet 6. The flow of enteral feed through the tube 10 may be regulated using an in-line regulator 15. The tube set also includes a control tap 22 and a pinch tube stopper 21.

The enteral feeding apparatus may be used in a sequence which is illustrated in FIGS. 67 to 77.

Figure 67:
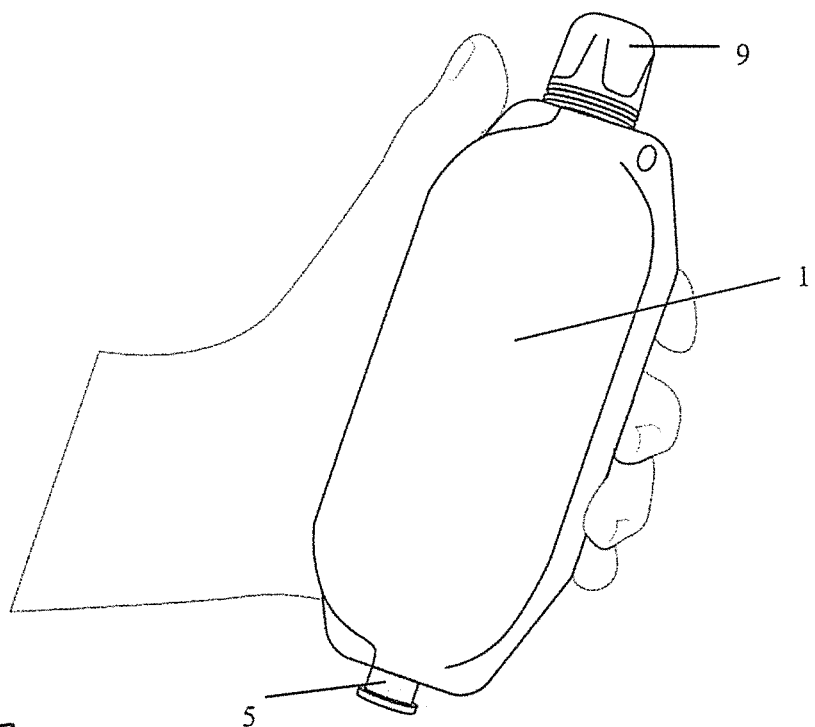
FIGS. 67 to 77 illustrate various steps in use of the enteral feeding apparatus.
Figure 68:
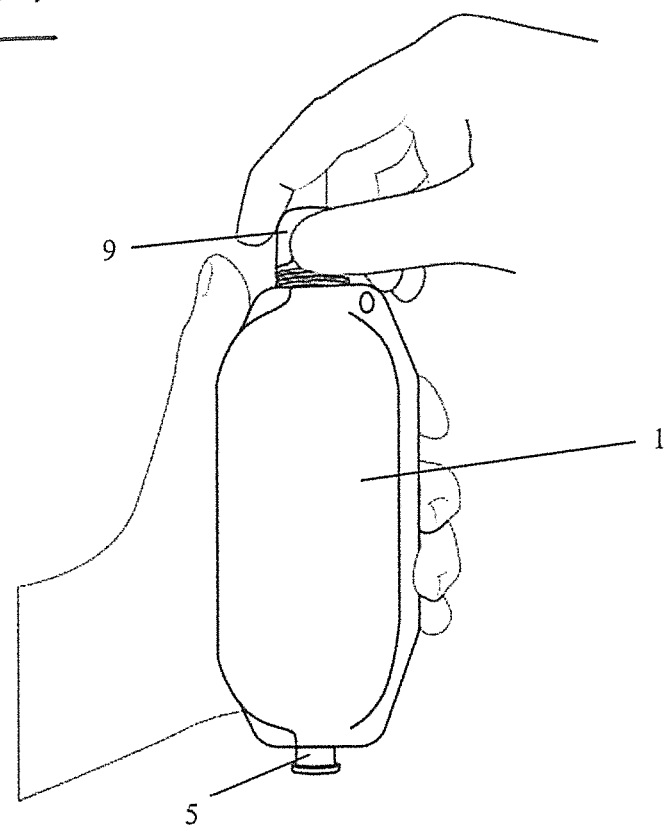
Figures 69, 70:
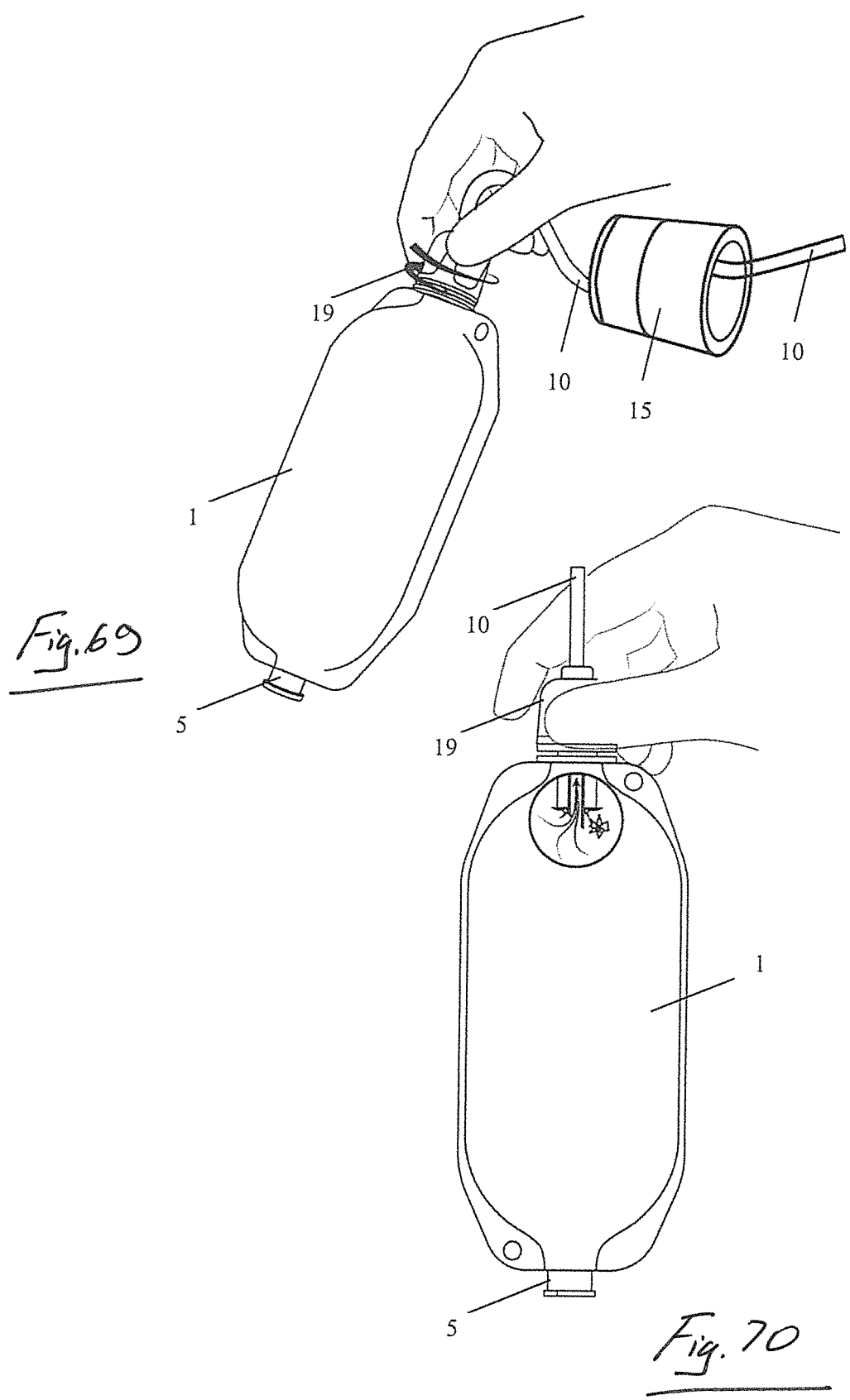

FIG. 67 shows a filled pod 1 ready for use. The user first removes the cap 9 from the outlet port (FIG. 68) and attaches the enteral feeding set (FIG. 69). Final rotation of the tube cap 19 causes seal 17 at the outlet port to be pierced.

FIG. 70 illustrates the start of release of enteral fluid from the pod when the foil seal 7 has been pierced.

Figure 71:
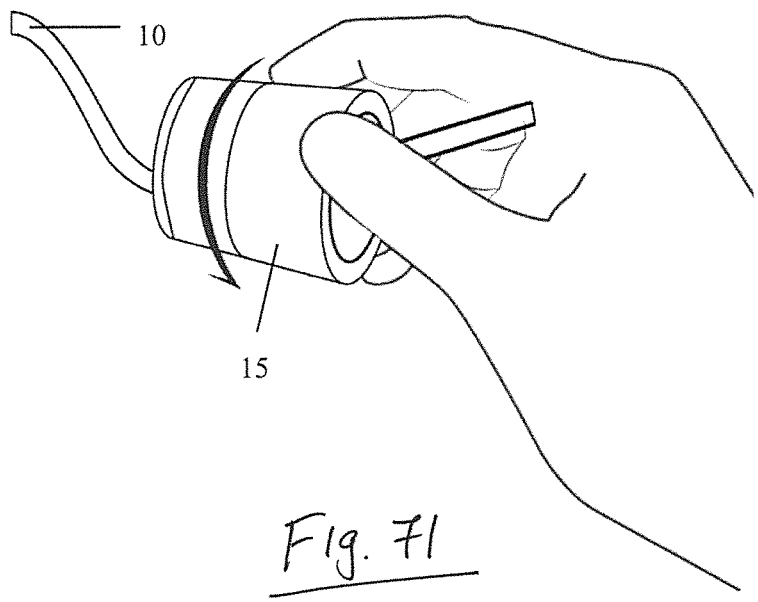

FIG. 71 shows the user twisting the regulator 15 to the prime function after the feeding tube set has been connected to the ENFit connection.

Figure 72:
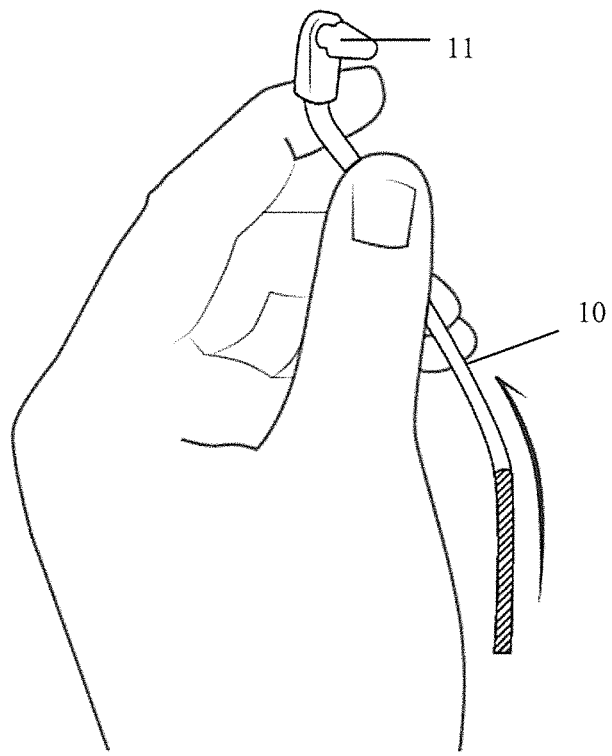

FIG. 72 shows the feed moving at a fast pace through the tubing 10 to the PEG connection 11 at the end of the feeding tube set. The user can visually inspect the movement of feed through the tube 10 and when near the PEG connection 11 the system is primed for feeding.

Figure 73:
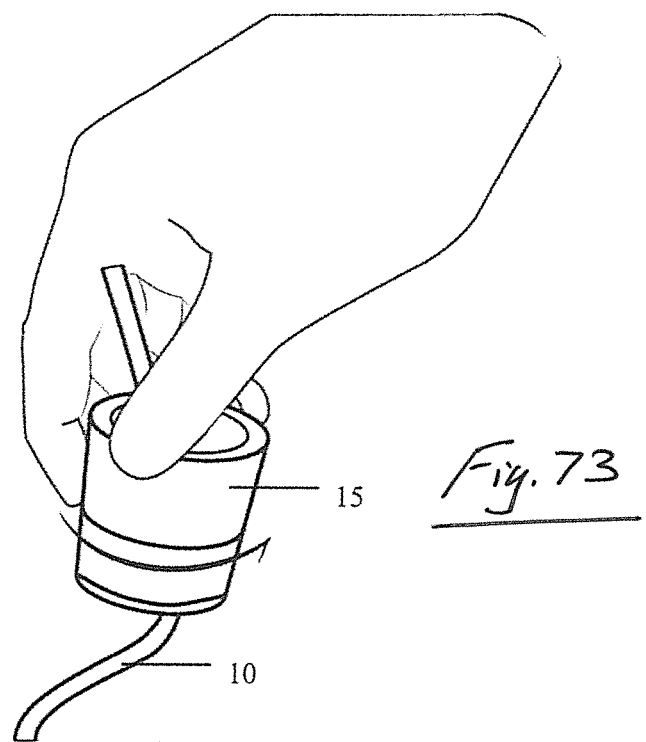

FIG. 73 shows the user turning the regulator 15 to select the desired flow rate, typically, between 50 ml to 150 ml per hour.

Figure 74:
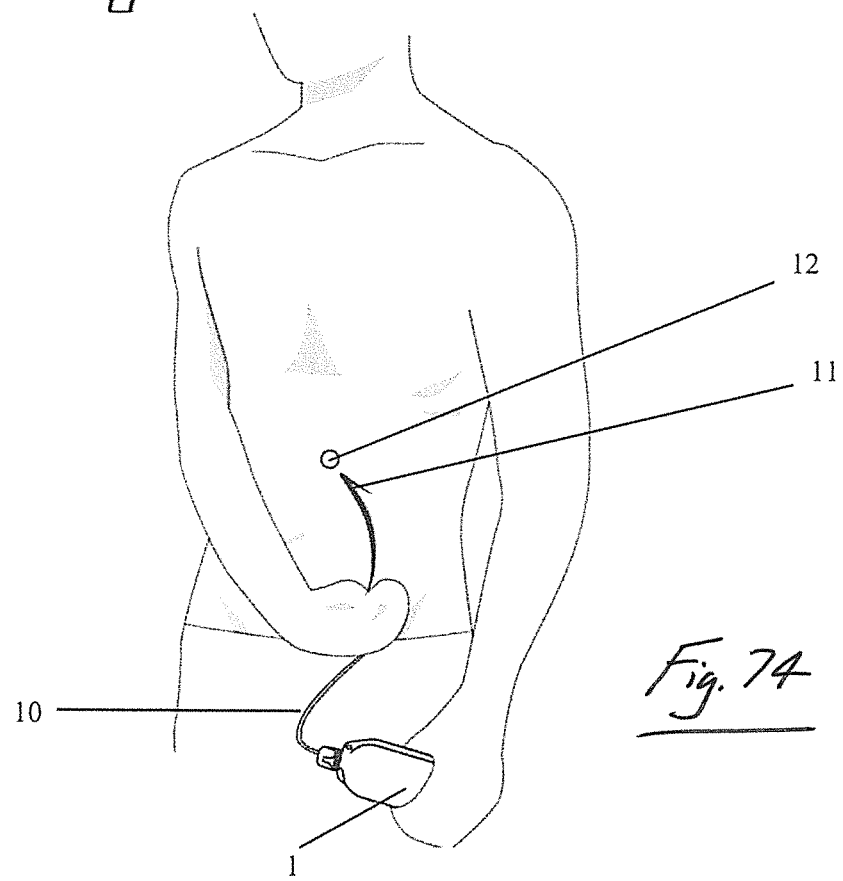

FIG. 74 shows the PEG connection/food pod being connected to the PEG implant. The food pod 1 is pumping feed directly into the stomach and is active. The food pod 1 can then be concealed or placed in a desired location.

Figure 75:
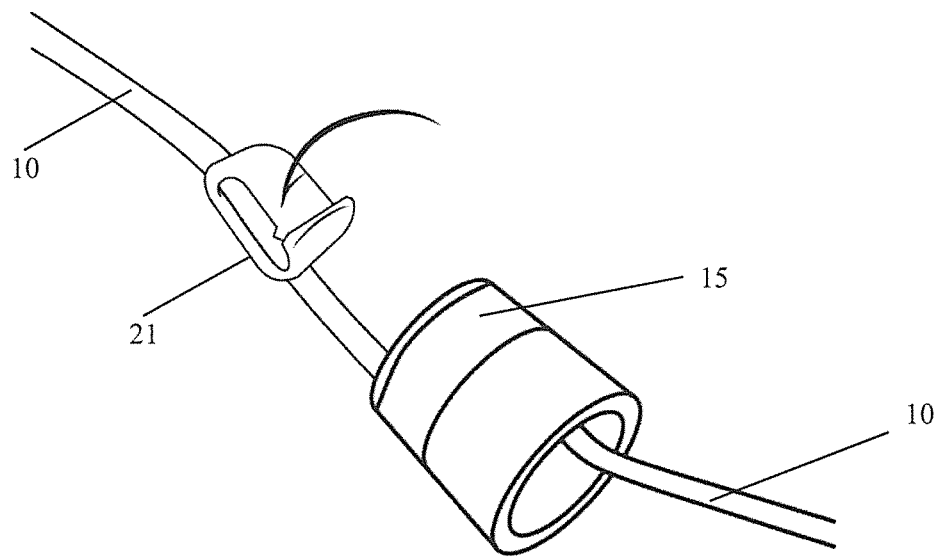

FIG. 75 shows a pinch tube stopper 21 that may be used to stop flow going through the tube 10. When the food pod has finished and is empty the stopper 21 is activated to prevent spillage from the PEG site. The image also shows, when fully primed during the priming stages, the food pod flow can be stopped with a stopper 21 that stops all enteral fluids from passing further through the tubing.

Figure 76:
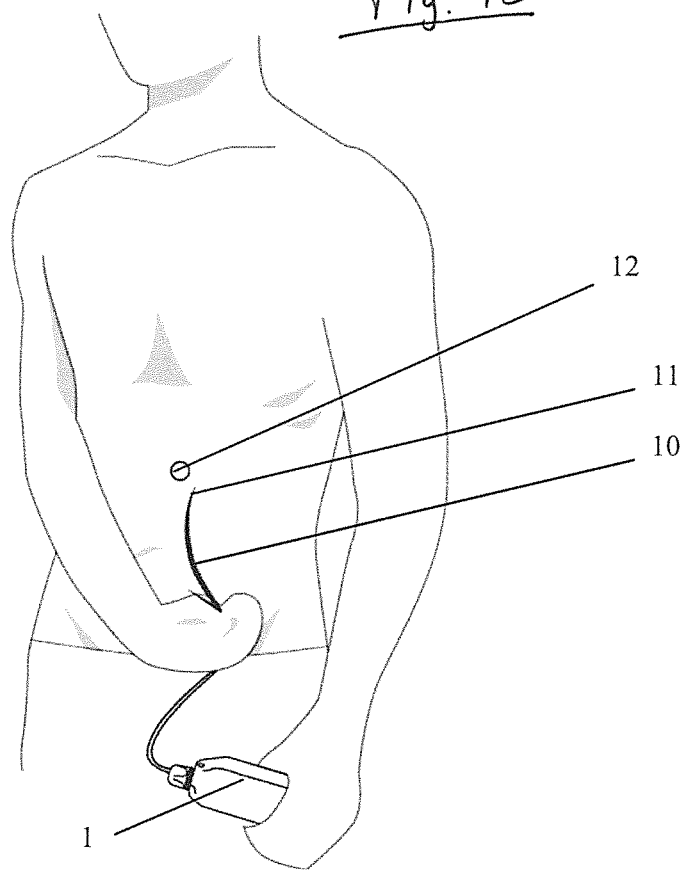

FIG. 76 shows the user disconnecting the food pod 1 from the PEG site. The user can disconnect the feeding tube set as the same feed set can be used for a full day (e.g. if a user uses three 500 ml food pods in a day it can be reused for each one). The feed set may be cleaned and flushed by connecting a syringe to the same ENFit connection that is connected to the food pod.

Figure 77:
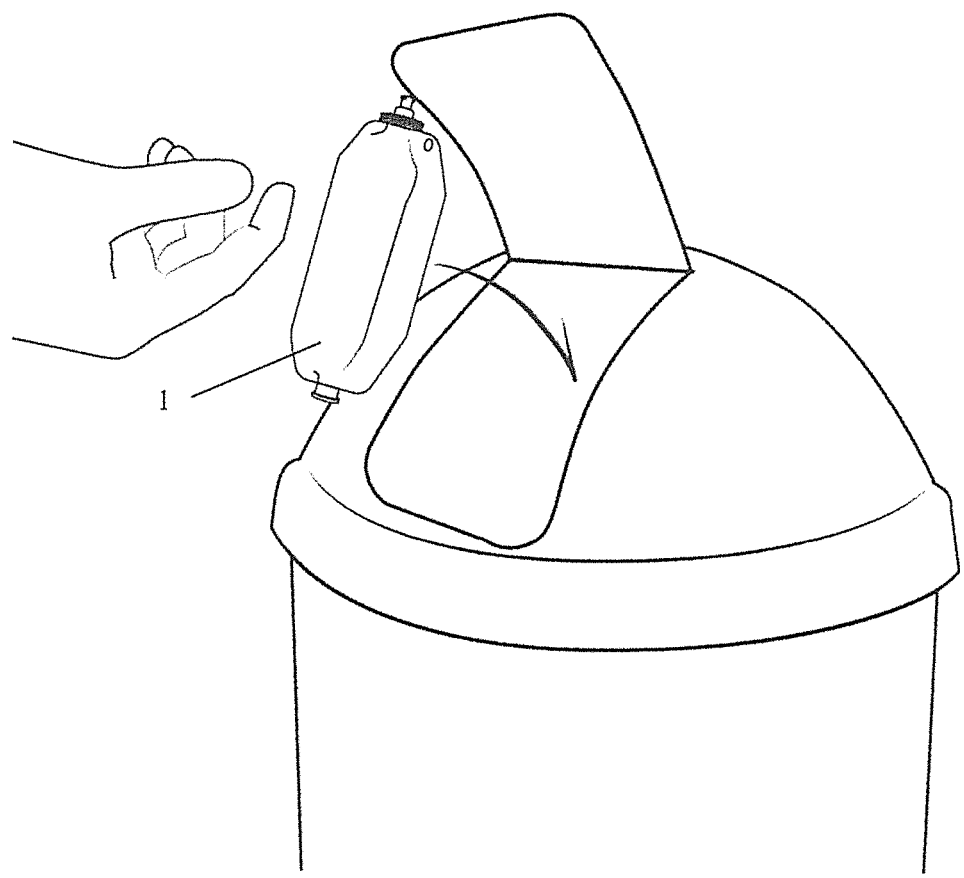

When finished, the food pod 1 may be disposed of as shown in FIG. 77.

The enteral feeding apparatus of the invention is small and tidy and offers the patient a much easier and faster setup, and less restriction when undertaking simple everyday jobs. The apparatus is light in weight and is easy for a user to carry around during the day. At night the apparatus has zero noise or vibrations leading to a better night's sleep.

The pouch is used to store the enteral fluid and apply pressure for delivery of enteral fluid from the device. The material of the pouch can be natural and/or synthetic (e.g. silicon, latex and isoprene rubber). The type of elastomer, number of elastomeric layers and the geometry of the reservoir pouch may be selected to regulate the pressure produced on the fluid in the manner of a stretched balloon.

Figure 78:
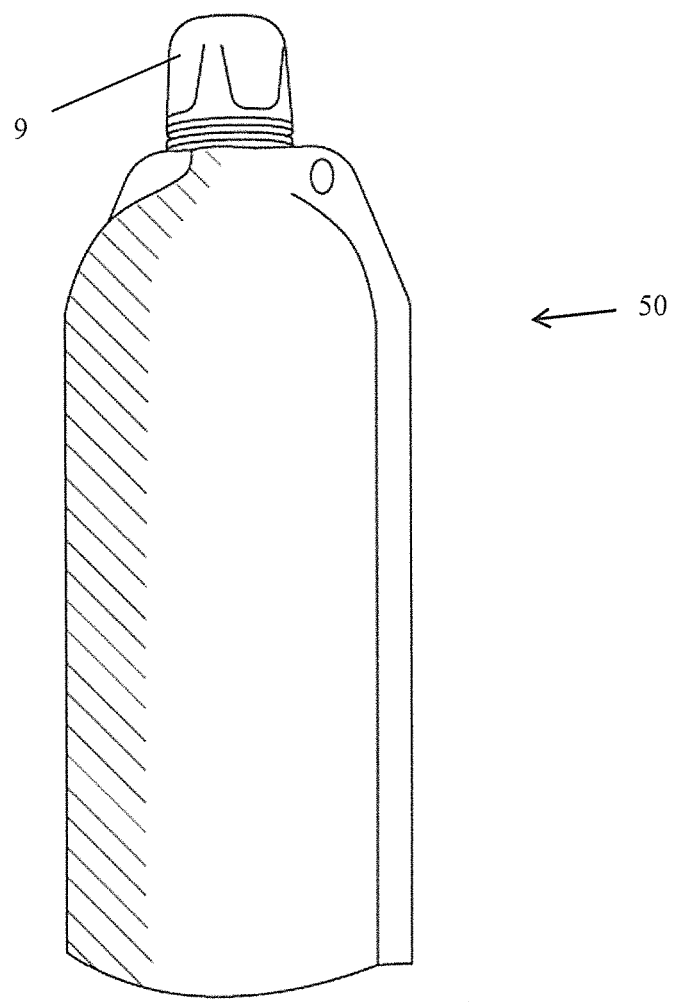
FIGS. 78 to 80 illustrate another enteral feeding apparatus according to the invention.
Figure 79:
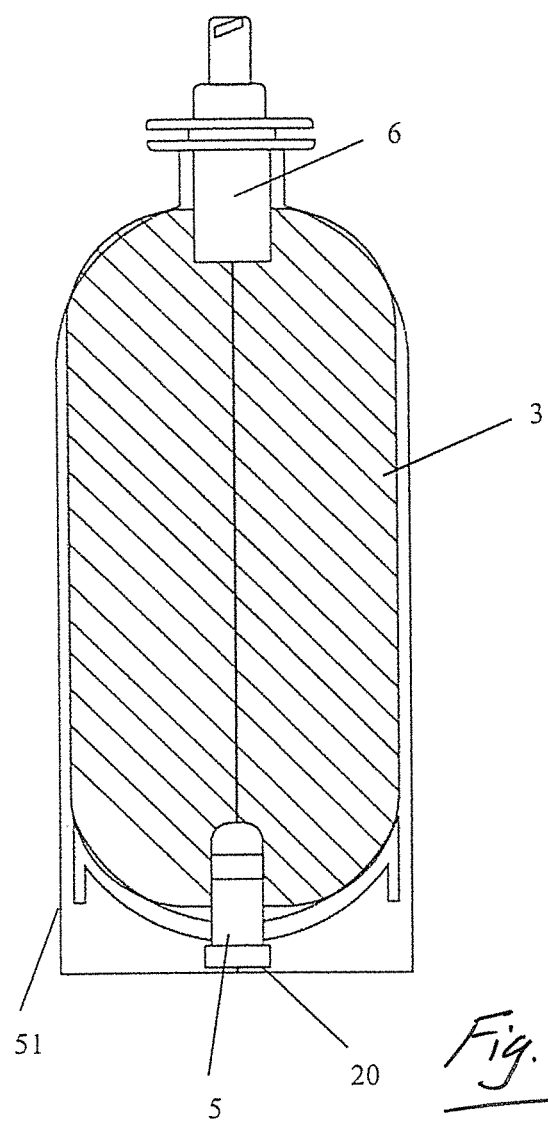
Figure 80:
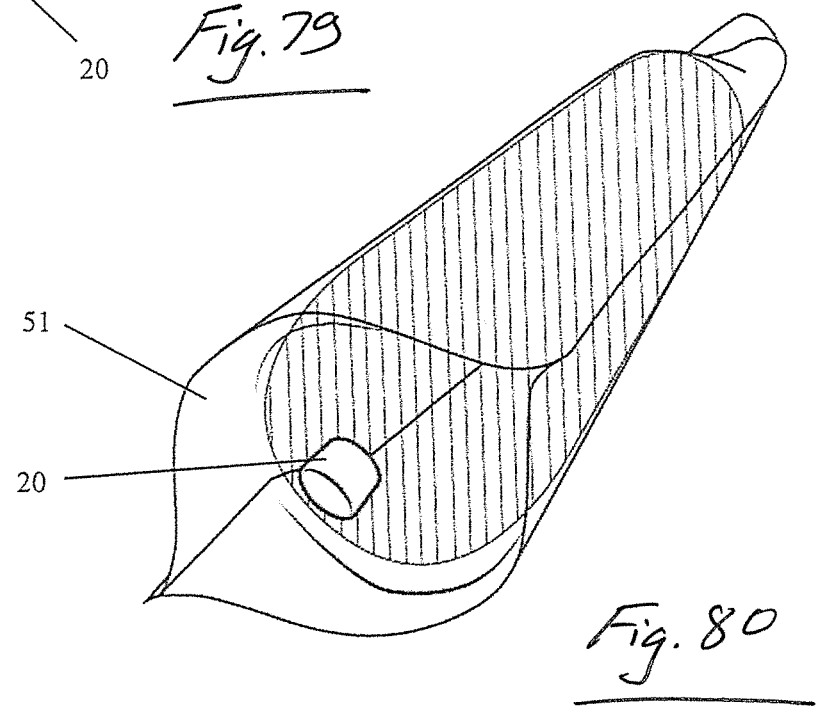

Referring to FIGS. 78 to 80 there is illustrated another enteral feeding pod 50 according to the invention. The pod 50 is similar to that described above and like parts are assigned the same reference numerals. In this case the pod 50 is free-standing. The pod has peripheral walls 51 that extend downwardly from the main body. The walls 51 terminate in a common base plane. The region bonded by the walls 51 in this case also accommodates the inlet port cap 20.

The additional advantage of this arrangement is that the pod can be readily mounted on any flat surface with enhanced flexibility for the user.

Figure 81:
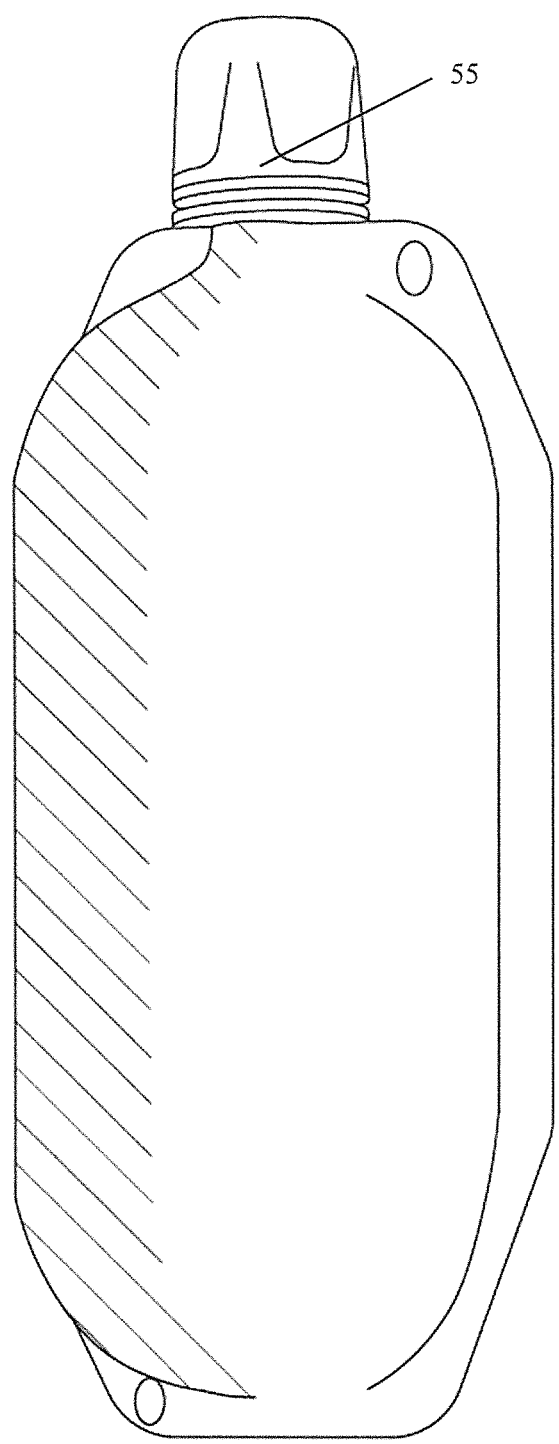
FIG. 81 illustrates another food pod according to the invention.

Referring to FIG. 81 there is illustrated another food pod according to the invention. The pod is similar to that described above except that in this case there is a common inlet/outlet 55 through which feed is introduced into and delivered from the pod.

FIGS. 82 and 83 show another enteral feeding pod 60 which includes a label 61 which include but not limited to a Near Field Communication tag 120 that allows to transmit small amounts of data through a distance of in some cases about 4 cm. Other suitable systems include RFID.

FIG. 15 shows an enteral feeding pod 200 being mounted to a docking station 201. The docking station 201 is used for monitoring feed rates at static locations such as bedside and chairside. The docking station 201 provides feedback and alarms to users and carers via interface, cloud and/or networks.

FIG. 16 shows the food pod interacting with the docking station 201. The food pod is placed into a holder in the docking station 201. The food pod is calibrated by the docking station and information is displayed on the screen of the docking station 119. Examples of the information include type of fluid; quantity such as 140 ml, flow rate such as 52 ml/ph.

In one case the elastomeric pouch is made from a synthetic membrane. When expanded, the membrane applies a pressure on the fluid. The properties of the material ensures return to the original shape when stretched. This occurs when the fluid is inserted into the reservoir causing the material to expand. One such membrane is of a material such as silicone that is compatible with enteral feeding fluid. Enteral fluid feed can contain any one or more of protein, carbohydrate, fat, water, minerals and vitamins from a wide range of sources including dairy and soya ingredients.

The pouch may comprise any suitable elastomeric material. The material preferably has a hardness on the Shore A scale. The selection of the material is based on the following properties:
  protection of the food (puncture proof etc.)
  output pressure (pouch squeeze), The output pressure is preferably about 10 psi
  food safe
  economical The material should also be capable of exhibiting a strain of ≥250% without exceeding the elastic limit of the material.

Suitable materials include the following available from Wacker:
  a) Elastosil M4600A/B Hardness Shore A 20, or
  b) Elastosil M4641 A/B Hardness Shore A 43.
  Alternatives to a) include Sorta Clear® 18
  Silastic® Q7-4720
  Tufel® II-94205
  Alternatives to b) include Dow Corsing® QPI-240
  Square® SSR3918-40
  Sorta Clear® 40

The barrier may be a laminate of two or more layers. One such material which is available from Bemis Packaging is:
  12 µm/20 µm/12 µm/65 µm PET/LLDPE/FOIL (AI)/PE white weld laminate
  PET—Barrier layer to oxygen egress and ingress
  LLDPE—Bond layer and colourant carrier
  Foil—Barrier layer to all ingress and egress typical aluminium
  PE—Weld layer.

The enteral feeding apparatus of the invention reduces the steps required to set up and start operation down to less than ten. This is a valuable advancement for the end-user. The apparatus is a safe, simple, reliable and an economical solution that:
  supports an active patient lifestyle
  has no alarms, meaning less disruption to the patients lifestyle and at night
  reduces the need for the use of complicated infusion pumps
  allows patients to be treated at home, as well as out and about in the community
  is easy to use, reduces training costs
  minimizes multiple nursing visits
  has a selection of volumes and flow rates
  does not require a power source
  reduction in maintenance time and cost In some cases the food pod may incorporate a means to identify how much feed is left within it such as a clear panel window in the packaging. Such as means may include a sensor to allow for the data to be received and then passed to an electronical device. Sensors that may be used include the following.

Graphene is a two-dimensional material made of carbon atoms. It is 200 times stronger than steel at one atom thick and is highly conductive. The large surface area of graphene can enhance the surface loading of desired biomolecules, and excellent conductivity and small band gap can be beneficial for conducting electrons between biomolecules and the electrode surface. A graphene sensor may be provided into/on/through the elastomeric pouch to allow for accurate pressure/quantity readings. This can allow the user to use a form of connectivity to generate data.

A copper sensor can be used as an antenna like RFID to transmit a radio wave through the feed to detect the size of the elastomeric pod and hence they quantity feed. Copper sensors are extremely sensitive and are completely wireless. Copper sensors are used for the measurement of pressure using two strips of copper acting like radio antennas and a specially designed rubber to be sandwiched in between. As pressure is put on the sensor, the material of the pouch changes thickness and a copper sensor may be used to detect this change. The sensor may be used to detect how much pressure is inside the elastomeric pouch by placing it in or on the elastomeric wall itself or placed around the wall.

With the addition on NFC if a sensor can engage the product to detect weight the NFC will be able to transmit the small amount of data to any smart technology or NFC readers which are currently available.

The invention is not limited to the embodiments hereinbefore described, which may be varied in construction and detail.

The invention claimed is:
1. An enteral feeding system comprising:
  a docking station,
  a portable enteral feeding device arranged to fit into the docking station,
  an enteral tube feeding fixture connected to the feeding device by a feeding line, and
  a regulator between the portable enteral feeding device and the enteral tube feeding fixturefor regulating the flow of enteral fluid from the portable enteral feeding device to the enteral tube feeding fixture,
  wherein:
  the docking station comprises:
  a detector comprising a sensor to deteiinine a quantity of feed in the portable enteral feeding device, wherein the sensor comprises a weight sensor,
  a processor to determine usage data according to inputs from the detector, and to identify a fault based on the rate of change of contained quantity in the portable enteral feeding device, and
  an interface to output data from the processor,
  a guide means comprising a tubular member for guiding the portable enteral feeding device to the detector, the portable enteral feeding device being guided upwardly and away from the docking station by the tubular member,
  a flexible sleeve for sealing engagement with the portable enteral feeding device in which the portable enteral feeding device fits in said flexible sleeve, said sleeve comprising a rim for surrounding and sealing against the portable enteral feeding device, and being config- ured to prevent spillages from contacting the detector, the portable enteral feeding device comprises:
- a pre-loaded pouch which defines a reservoir for enteral fluid, the pouch only containing enteral fluid in a pre-loaded condition, and
- an outlet port for delivery of enteral fluid from the pouch, the outlet port comprising features for engagement with a connector for connection to the enteral tube feeding line, in which the pouch includes an expansile element of polymeric material to provide a force by which enteral fluid is delivered from the pouch through the outlet port, towards the enteral tube feeding fixture, the pouch having an expanded filled configuration and a collapsed emptying configuration, the collapsed emptying configuration being caused by the force of the expansile element returning from the expanded filled configuration.

2. The enteral feeding system as claimed in claim 1, wherein the processor is configured to identify a stop in feed supply from the portable enteral feeding device, and to identify when a quantity of feed is below a pre-set level.

3. The enteral feeding system as claimed in claim 1, wherin the docking station comprises a sensor for detecting the portable enteral feeding device.

4. The enteral feeding system as claimed in claim 1, wherein the docking station comprises a tag sensor for detecting the portable enteral feeding device, and wherein the processor is calibrated to determine the nutritional content of feed in the pump by the tag sensor reading data from a tag on the pump, and wherein the sensor communicates with the tag using a wireless communication protocol.

5. The enteral feeding system as claimed in claim 1, wherein the processer is configured to alert the user to a fault in the supply of feed, wherein the alert is provided through a local alarm at the docking station, and wherein the alert can be transmitted to another device either local to or remote from the docking station.

6. The enteral feeding system as claimed in claim 1, further comprising a mounting system for the docking station.

7. The enteral feeding system as claimed in claim 1, further comprising a mounting system for the docking station, and wherein the mounting system comprises a bracket, and wherein the bracket is configured for attachment to a support.

8. The enteral feeding system as claimed in claim 1, wherein the portable enteral feeding device and the docking station comprise interfaces for wireless communication, and the portable enteral feeding device comprises a tag with stored nutritional data and a docking sensor interface is arranged to read said data.

9. The enteral feeding system as claimed in claim 1, further comprising a gas impermeable barrier surrounding the pouch.

10. The enteral feeding system as claimed in claim 1, wherein the portable enteral feeding device further comprises a sensor for detecting properties associated with enteral food.

11. The enteral feeding system as claimed in claim 1, comprising a removable cap for the outlet port.

\* \* \* \* \*